(12) United States Patent
Viricel

(10) Patent No.: US 12,734,244 B2
(45) Date of Patent: Sep. 15, 2026

(54) ANTIBODY-DRUG CONJUGATES AND THEIR USES

(71) Applicant: Mablink Bioscience, Lyons (FR)

(72) Inventor: Warren Viricel, Sainte Consorce (FR)

(73) Assignee: Mablink Bioscience, Lyons (FR)

( * ) Notice: Subject to any disclaimer, the term of this patent is extended or adjusted under 35 U.S.C. 154(b) by 0 days.

(21) Appl. No.: 18/844,818

(22) PCT Filed: Mar. 10, 2023

(86) PCT No.: PCT/EP2023/056097
§ 371 (c)(1),
(2) Date: Sep. 6, 2024

(87) PCT Pub. No.: WO2023/170247
PCT Pub. Date: Sep. 14, 2023

(65) Prior Publication Data
US 2025/0302978 A1 Oct. 2, 2025

(30) Foreign Application Priority Data
Mar. 11, 2022 (EP) .................................... 22305279

(51) Int. Cl.
*A61K 47/68* (2017.01)
*A61P 35/00* (2006.01)
*C07K 16/28* (2006.01)

(52) U.S. Cl.
CPC .... *A61K 47/68037* (2023.08); *A61K 47/6849* (2017.08); *A61K 47/6889* (2017.08); *A61P 35/00* (2018.01); *C07K 16/28* (2013.01)

(58) Field of Classification Search
IPC ................................................ A61K 47/68037
See application file for complete search history.

(56) References Cited

U.S. PATENT DOCUMENTS 5,677,425 A 10/1997 Bodmer et al.
5,714,350 A 2/1998 Co et al.
5,821,337 A 10/1998 Carter et al.
5,834,476 A 11/1998 Terasawa et al.
(Continued)

FOREIGN PATENT DOCUMENTS

EP 0154316 9/1985
WO 2005080431 9/2005
(Continued)

OTHER PUBLICATIONS

Cheng Xin et al., "MORAb-202, an Antibody-Drug Conjugate Utilitzing Humanized Anti-human FRa Farletuzumab and the Microtubule-targeting Agent Eribulin, has Potent Antitumor Activity," Molecular Cancer Therapeutics, 17 (12), Sep. 27, 2018, pp. 2672-2674.
(Continued)

*Primary Examiner* — Karl J Puttlitz
(74) *Attorney, Agent, or Firm* — Janet Martineau

(57) ABSTRACT

The present invention relates to antibody-drug conjugates, wherein the antibody specifically binds to folate receptor a, and wherein the drug is preferably chosen among a cytotoxic drug. Such antibody-drug conjugates are useful in particular in treating proliferative diseases including cancers, such as ovarian, breast and non-small cell lung cancers.

9 Claims, 22 Drawing Sheets

Specification includes a Sequence Listing.

(56) References Cited

U.S. PATENT DOCUMENTS

| | | | | |
|---|---|---|---|---|
| 6,248,516 | B1 | 6/2001 | Winter et al. | |
| 6,350,861 | B1 | 2/2002 | Co et al. | |
| 6,982,321 | B2 | 1/2006 | Winter et al. | |
| 7,087,409 | B2 | 8/2006 | Barbas, III et al. | |
| 2024/0216525 | A1 * | 7/2024 | Viricel | C07D 455/03 |

FOREIGN PATENT DOCUMENTS

| | | | | |
|---|---|---|---|---|
| WO | 2011106528 | | 9/2011 | |
| WO | 2017151979 | | 9/2017 | |
| WO | WO-2017151979 | A1 * | 9/2017 | A61P 35/00 |
| WO | 2019/055909 | A1 | 3/2019 | |
| WO | 2019044946 | | 3/2019 | |
| WO | 2019055909 | | 3/2019 | |
| WO | 2019/081455 | A1 | 5/2019 | |
| WO | 2019081455 | | 5/2019 | |
| WO | 2021007435 | | 1/2021 | |
| WO | 2021052402 | | 3/2021 | |
| WO | 2022207699 | | 10/2022 | |
| WO | 2022217022 | | 10/2022 | |
| WO | WO-2022207699 | A1 * | 10/2022 | A61K 47/549 |
| WO | 2023169896 | | 9/2023 | |
| WO | 2023178452 | | 9/2023 | |

OTHER PUBLICATIONS

Conilh Louise et al., "Exatecan Antibody Drug Conjugates Based on a Hydrophilic Polysarcosine Drug-Linker Platform," Pharmaceuticals, 14(3), Mar. 9, 2021, p. 247.
International Search Report and Written Opinion mailed Jun. 16, 2023, for PCT/EP2023/056097 filed Mar. 10, 2023.
Ray-Coquard, I. et al., Initial Results from a First-in-Human Phase I Study of LY4170156, an ADC Targeting Folate Receptor Alpha (FRα), in Advanced Ovarian Cancer and Other Solid Tumors, American Society of Clinical Oncology (ASCO) 61st Annual Meeting, Chicago USA, May 31-Jun. 3, 2025.
Viricel, W. et al., MBK-103, A Potent Novel Conjugation Platform-Based Antibody-Drug Conjugate, Chaning Therapeutic Options in Folate Receptor Alpha Positive Cancer Patients, American Association for Cancer Research (AACR) Annual Meeting 2023, Apr. 14-19, 2023, Abstract 1544.
Bax HJ, Chauhan J, Stavraka C, et al. Folate receptor alpha in ovarian cancer tissue and patient serum is associated with disease burden and treatment outcomes. Br J Cancer. 2023;128(2):342-353.
Chen YL, Chang MC, Huang CY, et al. Serous ovarian carcinoma patients with high alpha-folate receptor had reducing survival and cytotoxic chemo-response. Mol Oncol. 2012;6(3):360-369.
Cheung A, Bax HJ, Josephs DH, et al. Targeting folate receptor alpha for cancer treatment. Oncotarget. 2016;7 (32):52553-52574.
Despierre E, Lambrechts S, Leunen K, et al. Folate receptor alpha (FRA) expression remains unchanged in epithelial ovarian and endometrial cancer after chemotherapy. Gynecol Oncol. 2013; 130(1):192-199.
Kalli KR, Oberg AL, Keeney GL, et al. Folate receptor alpha as a tumor target in epithelial ovarian cancer. Gynecol Oncol. 2008;108(3):619-626.
Köbel M, Madore J, Ramus SJ, et al. Evidence for a time-dependent association between FOLR1expression and survival from ovarian carcinoma: implications for clinical testing. An Ovarian Tumour Tissue Analysis consortium study. Br J Cancer. 2014;111(12):2297-2307.
Leung F, Dimitromanolakis A, Kobayashi H, Diamandis EP, Kulasingam V. Folate-receptor 1 (FOLR1) protein is elevated in the serum of ovarian cancer patients. Clin Biochem. 2013;46(15):1462-1468.
Mai J, Wu L, Yang L, et al. Therapeutic strategies targeting folate receptor a for ovarian cancer. Front Immunol. 2023;14:1254532.
Matulonis UA, Lorusso D, Oaknin A, et al. Efficacy and Safety of Mirvetuximab Soravtansine in Patients With Platinum-Resistant Ovarian Cancer With High Folate Receptor Alpha Expression: Results From the SORAYA Study. J Clin Oncol. 2023;41(13):2436-2445.
Moore KN, Angelergues A, Konecny GE, et al. Mirvetuximab Soravtansine in FRa-Positive, Platinum-Resistant Ovarian Cancer. N Engl J Med. 2023;389(23):2162-2174.
Scaranti M, Cojocaru E, Banerjee S, Banerji U. Exploiting the folate receptor a in oncology. Nat Rev Clin Oncol. Jun. 2020; 17(6):349-359.
Toffoli G, Cernigoi C, Russo A, Gallo A, Bagnoli M, Boiocchi M. Overexpression of folate binding protein in ovarian cancers. Int J Cancer. 1997;74(2):193-198.
Toffoli G, Russo A, Gallo A, et al. Expression of folate binding protein as a prognostic factor for response to platinum-containing chemotherapy and survival in human ovarian cancer. Int J Cancer. 1998;79(2):121-126.

* cited by examiner

FIGURE 4
A
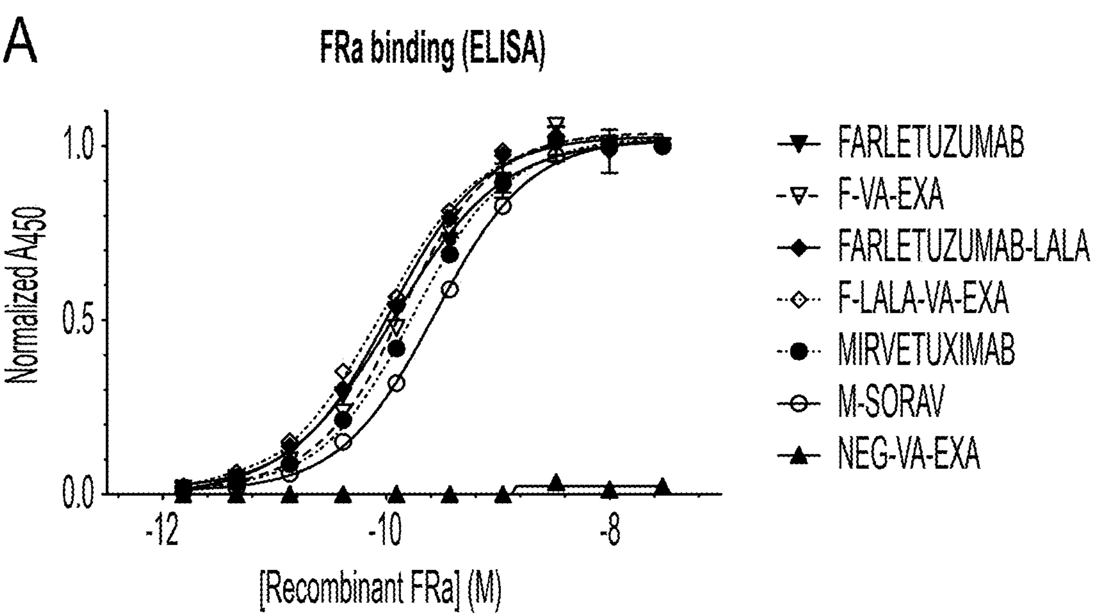
B
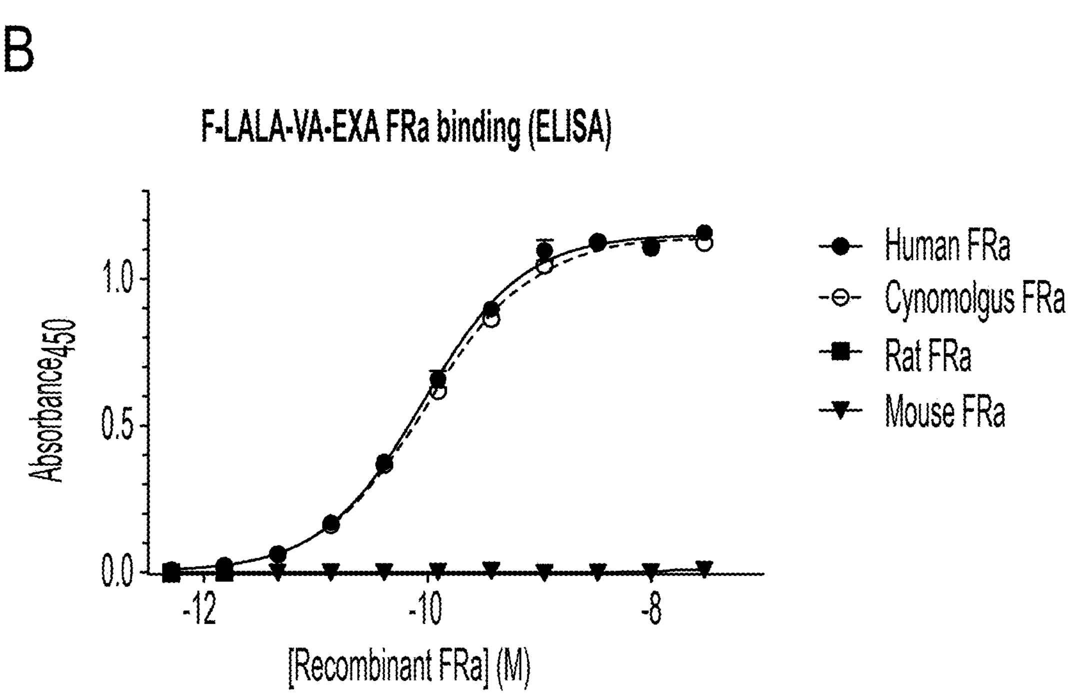

FIGURE 5

| | ka (1/M.s) | s.d. $k_a$ (1/M.s) | $k_d$ (1/s) | s.d. $k_d$ (1/s) | $K_D$ (M) | s.d. $K_D$ (M) |
|---|---|---|---|---|---|---|
| MIRVETUXIMAB | $1.15 \times 10^6$ | $2.12 \times 10^3$ | $2.44 \times 10^{-4}$ | $2.83 \times 10^{-7}$ | $2.11 \times 10^{-10}$ | $7.01 \times 10^{-14}$ |
| M-SORAV | $1.26 \times 10^6$ | $4.24 \times 10^3$ | $3.27 \times 10^{-4}$ | $1.70 \times 10^{-6}$ | $2.60 \times 10^{-10}$ | $4.95 \times 10^{-13}$ |
| FARLETUZUMAB | $1.90 \times 10^6$ | $1.73 \times 10^6$ | $3.61 \times 10^{-2}$ | $1.81 \times 10^{-2}$ | $2.51 \times 10^{-8}$ | $1.33 \times 10^{-8}$ |
| F-VA-EXA | $1.00 \times 10^6$ | $0.06 \times 10^6$ | $3.06 \times 10^{-2}$ | $0.03 \times 10^{-2}$ | $3.09 \times 10^{-8}$ | $0.02 \times 10^{-8}$ |
| FARLETUZUMAB-LALA | $1.34 \times 10^6$ | $0.58 \times 10^6$ | $3.21 \times 10^{-2}$ | $0.48 \times 10^{-2}$ | $2.55 \times 10^{-8}$ | $0.75 \times 10^{-8}$ |
| F-LALA-VA-EXA | $1.33 \times 10^6$ | $0.02 \times 10^6$ | $3.68 \times 10^{-2}$ | $0.13 \times 10^{-2}$ | $2.78 \times 10^{-8}$ | $0.07 \times 10^{-8}$ |
| NEG CTRL SINO BIO LOGICALS CAT#HG1K | n.d. | n.d. | n.d. | n.d. | n.d. | n.d. |
| NEG-VA-EXA | n.d. | n.d. | n.d. | n.d. | n.d. | n.d. |

$k_a$: association rate constant, mean calculated over replicates s.d. $k_a$: standard deviation of association rate constant $k_d$: dissociation rate constant, mean calculated over replicates s.d. $k_d$: standard deviation of dissociation rate constant $K_D$: affinity constant, calculated as $k_d/k_a$ s.d. $K_D$: standard deviation of affinity constant n.d.: not determined FIGURE 6
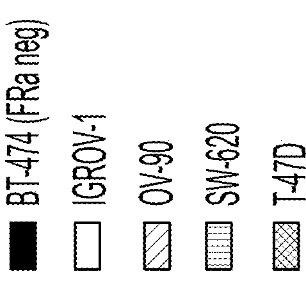
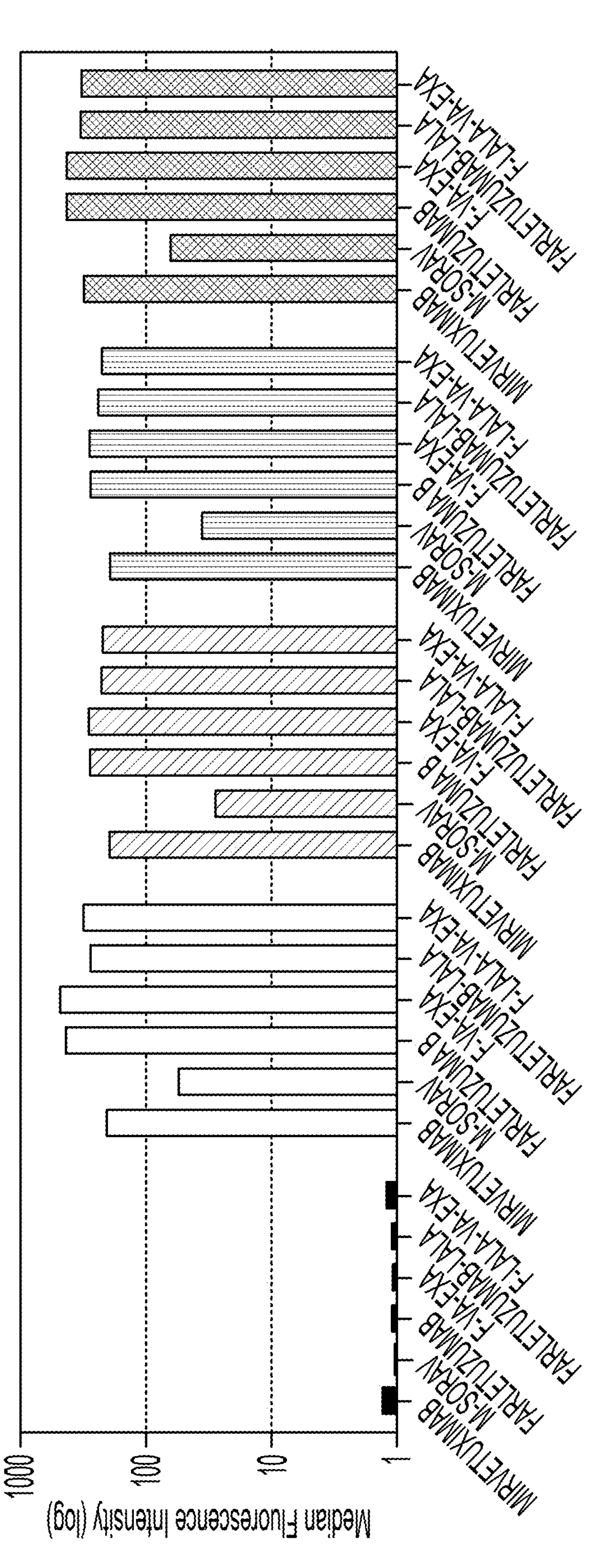

KB tumor xenograft experiment (n=7 mice/group)

Control
F-VA-EXA (3 mg/kg IV once)
F-VA-EXA (6 mg/kg IV once)
F-VA-EXA (12 mg/kg IV once)
F-LALA-VA-EXA (3 mg/kg IV once)
F-LALA-VA-EXA (6 mg/kg IV once)
F-LALA-VA-EXA (12 mg/kg IV once)
M-SORAV (3 mg/kg)
M-SORAV (6 mg/kg)
M-SORAV (12 mg/kg)
NEG-VA-EXA (12 mg/kg IV once)

IGROV-1 tumor xenograft experiment (n=7 mice/group)

Control (PBS)
F-LALA-VA-EXA (3 mg/kg IV once)
F-LALA-VA-EXA (6 mg/kg IV once)
F-LALA-VA-EXA (12 mg/kg IV once)
M-SORAV (3 mg/kg IV once)
M-SORAV (6 mg/kg IV once)
M-SORAV (12 mg/kg IV once)
NEG-VA-EXA (12 mg/kg IV once)
Regrowth challenge (new animals)
Regrowth challenge on animals from F-LALA-VA-EXA (12mg/kg IV once) group

| | Control (PBS) | F-VA-EXA (200 mg/kg) | F-LALA-VA-EXA (200 mg/kg) | M-SORAV (100 mg/kg) |
|---|---|---|---|---|
| **Deaths** | None | None | None | 5/5 deaths (at day 2 and 3) |
| **Lethal dose (mg/kg)** | N/A | >200 mg/kg | >200 mg/kg | <100 mg/kg |
| **Observed toxicities** | None | None | None except 1 animal with minor diarrhea | Diarrhea, prostration, unkempt appearance with fuzzy fur, subdued behavior, closed eyes |

| Total ADC | F-VA-EXA | F-LALA-VA-EXA |
|---|---|---|
| Clearance rate (mL/day/kg) | 5.0 | 5.5 |
| $AUC_{0\text{-}inf}$ (μM/day) | 3501 | 3143 |
| Vss (steady-state Vd) (mL/kg) | 110 | 130 |
| Half-life (days) | 13.5 | 15.2 |

FIGURE 22

| Doses | 30mg/kg | 40mg/kg | 50mg/kg | 60mg/kg |
| --- | --- | --- | --- | --- |
| Regimens | Intravenous, every 3 weeks<br>Days 1, 22, 43 (3 times in total) | | | |
| Lethal dose | Tolerated | Tolerated | Tolerated | Not tolerated, animal #1 euthanasia at day 9 and animal #2 scheduled euthanasia at day 21 |
| Body weight and food consumption | Normal | Normal | Normal | Weight loss and decreased food consumption |
| Hematology | Normal RBC<br>Normal WBC | Normal RBC<br>Normal WBC | Normal RBC<br>Decreased WBC, reversible | Normal RBC<br>Decreased WBC |
| Clinical chemistry | Normal | Normal | Normal | Increased creatinine, urea and perturbated electrolytes.<br>Increased reversible alanine transaminase, aspartate transaminase and total bilirubin |
| Target organs and tissues, histopathology | Reversible liquid feces. Few dark skin spots in some animals. Minor (non-adverse) kidney tubular regeneration and/or tubular casts | | | Liquid feces. Few dark skin spots in one animal<br>Acute renal failure leading to death of one animal (second animal recovered). Mild tubular degeneration, moderate tubular regeneration, and mild tubular casts (proteinaceous and cellular) in the kidneys, consistent with acute to subchronic renal failure<br>Mild dilatation of lacteals in the duodenum and minimal hepatocellular atrophy in the liver |
| HNSTD | 50 mg/kg (3 times in total, every 3 weeks) | | | |

RBC= red blood cells ; WBC = white blood cells ; HNSTD = highest non-severely toxic dose

ANTIBODY-DRUG CONJUGATES AND THEIR USES

SEQUENCE LISTING FILE

The present application is being filed along with a Sequence Listing in ST.26 XML format. The Sequence Listing is provided as a file titled "30954 US" created 1 May 2025 and is 20 kilobytes in size. The Sequence Listing information in the ST.26 XML format is incorporated herein by reference in its entirety.

TECHNICAL FIELD

It is hereafter disclosed antibody-drug conjugates, wherein the antibody specifically binds to folate receptor alpha (FRα), and wherein the drug is preferably chosen among inhibitors of topoisomerase I, for example camptothecine analogues such as exatecan. Such antibody-drug conjugates are useful in particular in treating proliferative diseases including cancers, such as ovarian cancer, breast cancer or lung cancer.

BACKGROUND

Antibody-drug conjugates (hereafter referred as "ADCs") are a new class of therapeutics, notably cancer therapeutics. Such ADCs comprise at least an antibody and a payload (e.g. a cytotoxic drug), both covalently bonded by a linker. ADCs are therefore designed to combine the specificity of antibody target with the efficiency of the payload (e.g. the cytotoxic activity of a chemotherapeutic agent). Efficient ADCs should exhibit high specificity and low systemic toxicity.

Within the context of toxicity, antibody used in ADCs needs to bind accurately and efficiency to its antigen, meaning that the suitable target antigen is preferentially or exclusively expressed on targeted cells.

When designing an ADC, there is a need to covalently attach the final active drug to the ligand targeting unit, while allowing the final release of the active drug unit by a selective enzymatic mechanism after cellular internalization, or in the diseased tissue microenvironment. In this regard, several peptidase- and glycosidase-sensitive cleavable linker chemical strategies (associated with self-immolative chemistries) were developed. These cleavable linkers and their corresponding cleavage mechanisms are well known and have been described in several publications (e.g. Bargh J G et al., Chem. Soc. Rev., 2019, 48, 4361, Toki et al. *J. Org. Chem.* 2002, 67, 6, 1866-1872, Scott et al. *Bioconjugate Chem.* 2006, 17, 3, 831-840). The choice of this enzyme-sensitive cleavable entity is a critical design attribute of the ADC, impacting efficacy and tolerability of the conjugate.

Examples of linker types that have been used to conjugate a cytotoxin or a drug to an antibody include, but are not limited to, hydrazones, thioethers, esters, disulfides and peptide-containing linkers. Linkers are for example chosen among those susceptible to cleavage by low pH within the lysosomal compartment or susceptible to cleavage by proteases, such as proteases preferentially expressed in tumor tissue, for example cathepsins (e.g. cathepsins B, C, D). Efficient linker can ensure an accurate and timely release of the payload. Within the context of toxicity, it also appears that the stability of the linker can impact the toxicity exerted by the payload, even if the linker itself does not appear to drive toxicity. Indeed, a stable linker can release the payload in a target-specific manner whereas a not-stable linker is more likely to undergo a non-accurate release of the payload (for example due to a non-specific cleavage), leading to a non-specific systemic toxicity.

Payloads used in ADCs are highly potent, often cytotoxic drugs having in vitro inhibitory concentrations in the picomolar range. Common payloads are for example microtubule inhibitors (such as maytansine derivatives (DM1/DM4), auristatins (MMAE/MMAF), eribulin) and DNA alkylators (such as calicheamicin, pyrrolobenzodiazepines, indolinobenzodiazepines, or duocarmycins).

Although ADCs appear to be promising therapeutics, some ADC can be too toxic, which limit the therapeutic window of these compounds or prevent further clinical development. Furthermore, most of the ADCs that are currently approved or under clinical investigation are based on microtubule- and DNA-targeting agents as cited above. As such, there is a need for new differentiated ADCs based on payloads having other mechanism of action, in order to efficiently treat tumors that are or become resistant to microtubule- and DNA-targeting agents.

Efficient ADCs exhibiting high specificity, maximum efficiency and low toxicity require therefore an appropriate combination of each of its components. For a review of possible strategies, see for example Khongorzul et al 2019 (Molecular cancer research, DOI: 10.1158/1541-7786.MCR-19-0582). WO2019081455 and Conilh et al (2021, Pharmaceuticals, 14 (3), 247) further report HER2-targeting antibody-drug conjugate, in particular based on the topoisomerase I inhibitor payload Exatecan, and using a hydrophilic monodisperse polysarcosine (PSAR) drug-linker platform.

Cheng et al (2018, DOI: 10/1158/1535-7163.MCT-17-1215) and WO2017151979 reports ADCs with farletuzumab conjugated to typically 3 to 4 molecules of eribulin (MORAb-202) and its use in treating tumors. The mechanism of action of the eribulin payload of this ADC is microtubule inhibition.

Moore et al (2018, Future Oncol. 14 (17) 1669-1678) report the results of a phase III study with the ADC mirvetuximab soravtansine, comprising mirvetuximab, a humanized anti-FRα antibody, conjugated with an average of 3 to 4 maytansinoid molecules as the payload, for the treatment of ovarian cancer. The mechanism of action of the maytansin payload of this ADC is microtubule inhibition.

Hence, there is still a need for an antibody-drug conjugate comprising an anti-FRα antibody which is efficient, has high specificity, low toxicity (improved therapeutic index) and differentiated mechanism of action of the payload.

As shown in the Examples, the present disclosure provides topoisomerase I inhibitor-based anti-FRα antibody-drug conjugates with excellent in vivo efficacy in solid tumor cancer models and low toxicity, in particular when compared with reference prior art ADCs targeting FRα-expressing antibody with other payload and drug linkers, such as mirvetuximab soravtansine.

SUMMARY

Accordingly, a first object of the disclosure relates to an antibody-drug conjugate (ADC) of the formula (I):

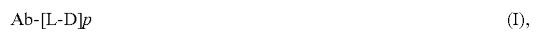

$$Ab\text{-}[L\text{-}D]p \quad (I),$$

wherein:

Ab is an anti-folate receptor alpha (FRα) antibody which binds specifically to SEQ ID NO: 12,

- L is a cleavable linker moiety bonded to said anti-folate receptor alpha (FRα) antibody preferably via a thiol residue,
- D is a cytotoxic drug moiety bonded to L,
- p is from 1 to 8, preferably from 6 to 8, and more preferably p is 8.

In specific embodiments, Ab is an antibody comprising a human IgG1 isotype constant region.

In a preferred embodiment, Ab is an antibody comprising a mutant or chemically modified constant region of human IgG1 isotype, wherein said mutant or chemically modified constant region confers no or decreased ADCC activity to said antibody when compared to a corresponding antibody with wild type human IgG1 isotype constant region.

In other specific embodiments, Ab is an antibody which comprises a human IgG4 isotype constant region, or a mutant or chemically modified IgG4 constant region, wherein said mutant or chemically modified constant region confers no or decreased ADCC activity to said antibody when compared to a corresponding antibody with wild type IgG4 isotype constant region.

In preferred embodiments, Ab is an anti-FRα antibody comprising either:

- (a) a variable heavy chain polypeptide comprising HCDR1 of SEQ ID NO:1, HCDR2 of SEQ ID NO:2, HCDR3 of SEQ ID NO:3 and a variable light chain polypeptide comprising LCDR1 of SEQ ID NO:4, LCDR2 of SEQ ID NO:5 and LCDR3 of SEQ ID NO:6; or,
- (b) a variable heavy chain polypeptide comprising VH of SEQ ID NO:7 and a variable light chain polypeptide comprising VL of SEQ ID NO:8.

In specific embodiments, said Ab comprises or essentially consists of a heavy chain of SEQ ID NO:9 and a light chain of SEQ ID NO:10; In specific embodiments, said Ab comprises or essentially consists of a heavy chain of SEQ ID NO:11 and a light chain of SEQ ID NO:10.

In specific embodiments, D is an inhibitor of topoisomerase I, preferably selected from the group consisting of camptothecine analogues, and more preferably D is the drug moiety of Exatecan of formula (II) below (II)

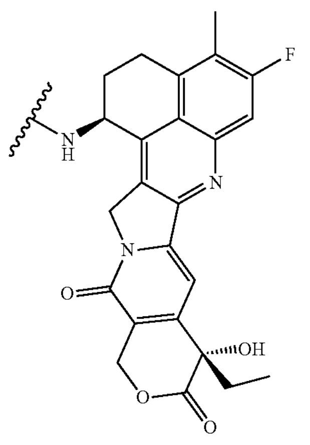

In specific embodiments, L is a cleavable linker moiety of formula -A-W—, wherein A is an optional stretcher unit linked to Ab, and W is a cleavable moiety linked to D. In a more specific embodiment, L is a lysosomal protease-sensitive linker, and W comprises a cleavable peptide moiety, for example selected from the group consisting of valine-citrulline (Val-Cit), alanine-alanine-asparagine (Ala-Ala-Asn), valine-alanine (Val-Ala) and phenylalanine-lysine (Phe-Lys). In another specific embodiment, L is a protease sensitive cleavable linker and W comprises a sugar cleavable unit, preferably selected from a β-glucuronide or a β-galactoside moiety. In another specific embodiment, L is a glutathione-sensitive linker and W comprises a disulfide moiety. In a specific embodiment, W is of the following formula (III)

(III)

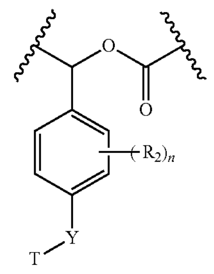

wherein

- each $R_2$ is independently selected from the group consisting of electron-withdrawing groups and $C_1$-$C_4$ alkyl;
- n is 0, 1 or 2;
- T is a sugar cleavable unit or a polypeptide cleavable unit;
- Y is O when T is a sugar cleavable unit, or $NR_3$ when T is a polypeptide cleavable unit; and
- $R_3$ is selected from the group consisting of H, $C_1$-$C_{24}$ alkyl, $C_2$-$C_6$ alkenyl; optionally substituted polyether, aryl having 6 to 10 ring atoms, $C_3$-$C_8$ cycloalkyl, heterocycloalkyl having 3 to 10 ring atoms, heteroaryl having 5 to 10 ring atoms, and any combination thereof,
- said alkyl and alkenyl being optionally interrupted by one or more heteroatom or chemical groups selected from —O—, —S—, —C(O)—, —NR"—, —C(O)NR"—, —NR"—C(O)—, —NR"—C(O)—NR"—, —NR"—C(O)—O—, —O—C(O)NR"— and triazole,
- R" and R" being independently selected from H and $C_1$-$C_6$ alkyl, and pharmaceutically acceptable salts thereof.

In a preferred embodiment, L corresponds to a linker -A-W— of formula (IV)

(IV)

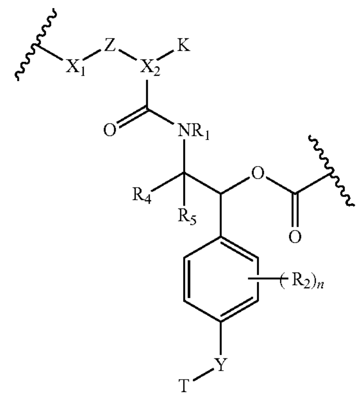

wherein

- $X_1$ is a connector unit;
- Z is an optional spacer;
- $X_2$ is a connector unit;
- K is an optional hydrophobicity masking entity, preferably selected from polysarcosine and polyethylene glycol;

$R_1$ is selected from the group consisting of H, $C_1$-$C_{24}$ alkyl, $C_2$-$C_6$ alkenyl; optionally substituted polyether, aryl having 6 to 10 ring atoms, $C_3$-$C_8$ cycloalkyl, heterocycloalkyl having 3 to 10 ring atoms, heteroaryl having 5 to 10 ring atoms, and any combination thereof, said alkyl and alkenyl being optionally interrupted by one or more heteroatom or chemical groups selected from —O—, —S—, —C(O)—, —NR"—, —C(O)NR"—, —NR"—C(O)—, —NR"—C(O)—NR'"—, —NR"—C(O)—O—, —O—C(O)NR"— and triazole;

$R_4$ is selected from the group consisting of H, $C_1$-$C_6$ alkyl and $C_2$-$C_6$ alkenyl, said alkyl and alkenyl being optionally interrupted by one or more heteroatom or chemical groups selected from —O—, —S—, —C(O)—, and —NR"—;

$R_5$ is selected from the group consisting of H, $C_1$-$C_6$ alkyl and $C_2$-$C_6$ alkenyl, said alkyl and alkenyl being optionally interrupted by one or more heteroatom or chemical groups selected from —O—, —S—, —C(O)—, and —NR"—.

In a more specific embodiment, $X_1$ and $X_2$ are independently selected from the group consisting of one or more amino acid(s), one or more N-substituted amino acid, optionally substituted polyether, $C_1$-$C_{12}$ alkylene, arylene having 6 to 10 ring atoms, $C_3$-$C_8$ cycloalkylene, heterocycloalkylene having 5 to 10 ring atoms, heteroarylene having 5 to 10 ring atoms, $C_2$-$C_{10}$ alkenylene, and any combination thereof, said alkylene and alkenylene being optionally interrupted by one or more heteroatom or chemical groups selected from —O—, —S—, —C(O)—, —NR"—, —C(O)NR"—, —NR"—C(O)—, —NR"—C(O)—NR'"—, —NR"—C(O)—O—, —O—C(O)NR"— and triazole, and said alkylene, arylene, cycloalkylene, heterocycloalkylene, heteroarylene, and alkenylene being optionally substituted with one or more of the substituents selected from: halogen, oxo, —OH, —$NO_2$, —CN, $C_1$-$C_6$ alkyl, $C_3$-$C_6$ cycloalkyl, heterocyclyl having 5 to 10 ring atoms, aryl having 6 to 10 ring atoms, heteroaryl having 5 to 10 ring atoms, $C_1$-$C_6$ alkoxy, $C_1$-$C_6$ haloalkyl, $C_1$-$C_6$ haloalkoxy, —(CO)—R', —O—(CO)—R', —(CO)—O—R', —(CO)—NR"R", —NR"—(CO)—R', and —NR"R";

R', R" and R" being independently selected from H and $C_1$-$C_6$ alkyl.

In a more specific embodiment, Z is independently selected from the group consisting of one or more amino acid(s), one or more N-substituted amino acid, optionally substituted polyether, $C_1$-$C_{12}$ alkylene, arylene having 6 to 10 ring atoms, $C_3$-$C_8$ cycloalkylene, heterocycloalkylene having 5 to 10 ring atoms, heteroarylene having 5 to 10 ring atoms, $C_2$-$C_{10}$ alkenylene, and any combination thereof, said alkylene and alkenylene being optionally interrupted by one or more heteroatom or chemical groups selected from —O—, —S—, —C(O)—, —NR"—, —C(O)NR"—, —NR"—C(O)—, —NR"—C(O)—NR'"—, —NR"—C(O)—O—, —O—C(O)NR"— and triazole, and said alkylene, arylene, cycloalkylene, heterocycloalkylene, heteroarylene, and alkenylene being optionally substituted with one or more of the substituents selected from: halogen, oxo, —OH, —$NO_2$, —CN, $C_1$-$C_6$ alkyl, $C_3$-$C_6$ cycloalkyl, heterocyclyl having 5 to 10 ring atoms, aryl having 6 to 10 ring atoms, heteroaryl having 5 to 10 ring atoms, $C_1$-$C_6$ alkoxy, $C_1$-$C_6$ haloalkyl, $C_1$-$C_6$ haloalkoxy, —(CO)—R', —O—(CO)—R', —(CO)—O—R', —(CO)—NR"R", —NR"—(CO)—R', and —NR"R";

R', R" and R" being independently selected from H and $C_1$-$C_6$ alkyl.

In specific embodiments, K is a polysarcosine, preferably of the following formula (V)

(V)

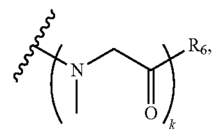

wherein k is an integer between 2 and 50, preferably between 4 and 30, and $R_6$ corresponds to OH or $NH_2$.

In specific embodiments, T is a sugar cleavable unit which is a glucuronide or a galactoside.

In other specific embodiments, T is a dipeptide, preferably selected from Val-Cit, Val-Ala and Phe-Lys.

In specific embodiments, L is covalently bonded to one or more thiol residues of said antibody, preferably, said L corresponding to a linker of formula (VI):

(VI)

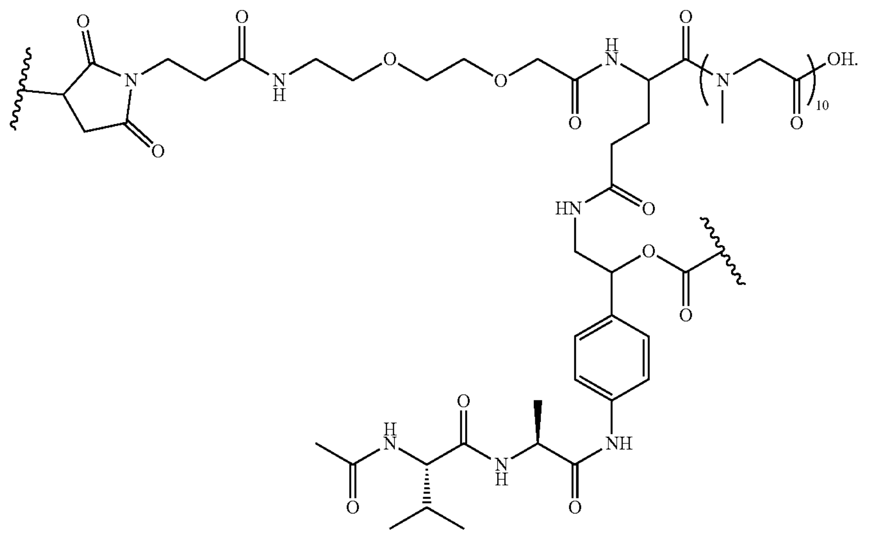

In specific embodiments, Ab includes full-length antibodies or antibodies fragments containing antigen binding portions.

In specific embodiments, the antibody drug conjugate corresponds to the following formula (VII)

(VII)

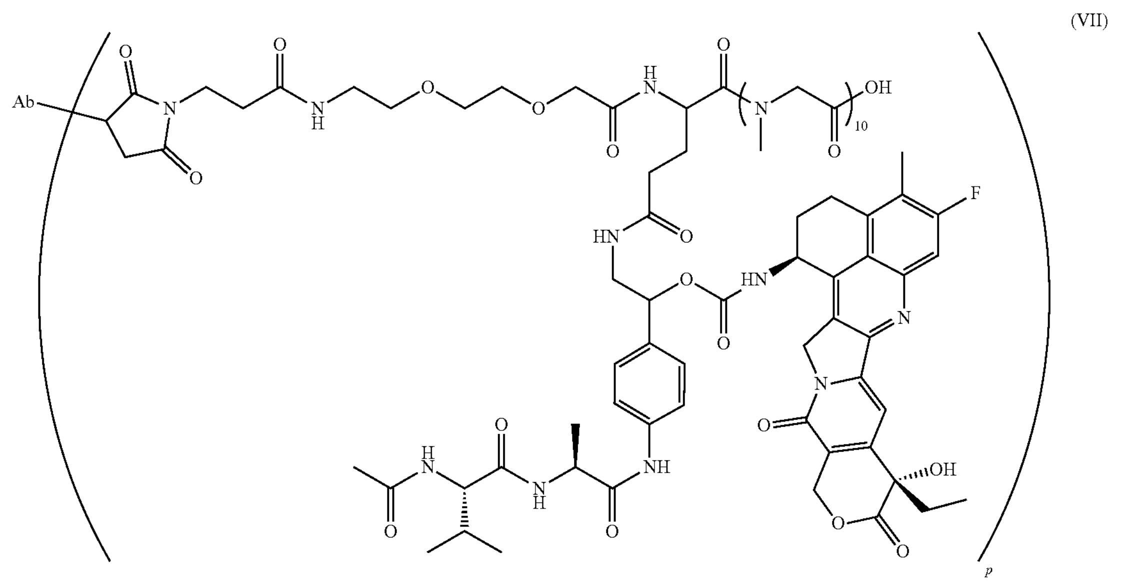

wherein Ab is an anti-FRα antibody, such as farletuzumab, or its silent IgG1 variants, typically comprising alanine substitutions in Leucine 234 and Leucine 235 of IgG1 Fc constant region, and p is from 4 to 8.

In a preferred embodiment, the antibody drug conjugate corresponds to the following formula (VII)

(VII)

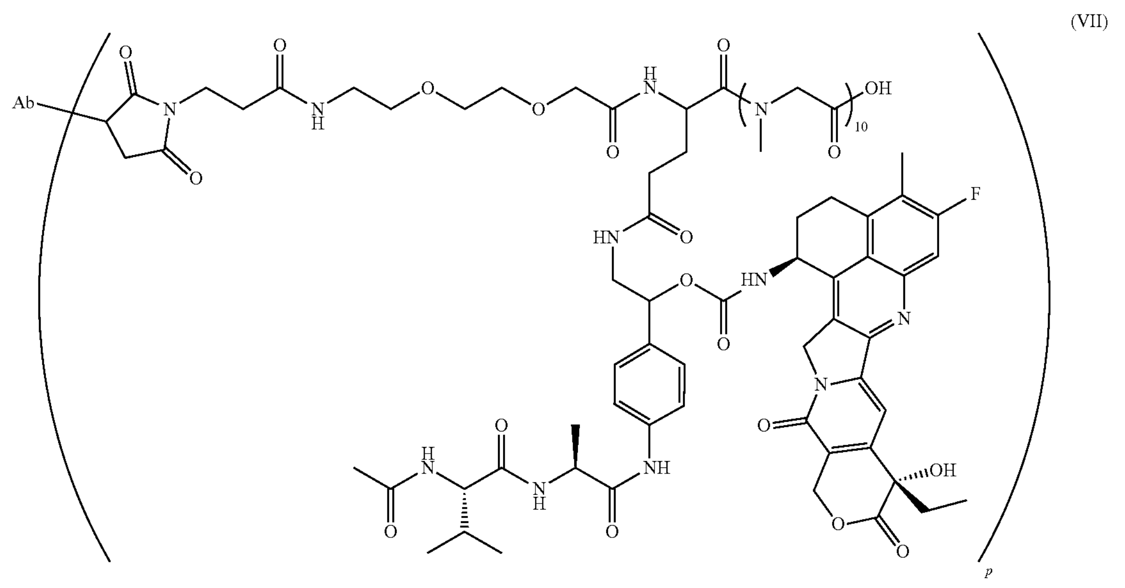

(VII)

wherein Ab is an anti-FRα antibody, such as farletuzumab, or its silent IgG1 variants, typically a mutant variant of human IgG1 comprising alanine substitutions in Leucine 234 and Leucine 235 of IgG1 Fc constant region, also commonly called as LALA mutations, and p is 8.

In a more preferred embodiment of the ADC of formula (I),

Ab is an anti-folate receptor alpha antibody or an antigen-binding fragment thereof, comprising
 (i) a variable heavy chain polypeptide comprising HCDR1 of SEQ ID NO:1, HCDR2 of SEQ ID NO:2, HCDR3 of SEQ ID NO:3 and
 (ii) a variable light chain polypeptide comprising LCDR1 of SEQ ID NO:4, LCDR2 of SEQ ID NO:5 and LCDR3 of SEQ ID NO:6;

The disclosure further relates to a pharmaceutical composition comprising an antibody-drug conjugate as disclosed herein, in combination with one or more pharmaceutical acceptable excipient, diluent or carrier, optionally comprising other active ingredients, for example anti-cancer drugs or immunotherapeutic drugs such as immune checkpoint inhibitors.

The disclosure also relates to the process for obtaining an ADC of the disclosure, wherein the method comprises:

(a) culturing a host cell under conditions suitable for production of the anti-FRα antibody as defined herein, (b) isolating said anti-FRα antibody, (c) synthesis of exatecan bonded to the linker L of formula (VIII):

(VIII)

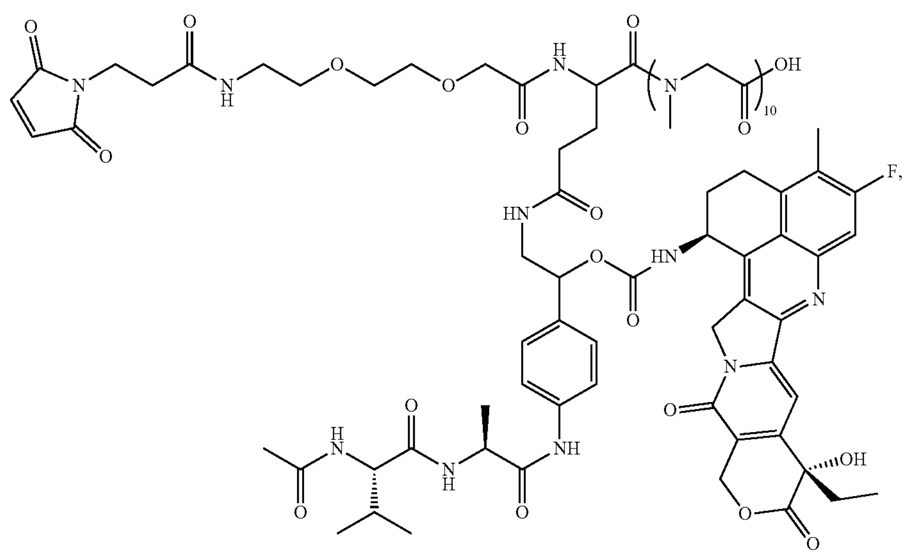

(d) conjugating said anti-FRα antibody to the compound of formula (VIII);

thereby obtaining an ADC of the disclosure.

L is a cleavable linker of formula -A-W—, wherein A is an optional stretcher unit linked to the Ab, and W is a cleavable moiety linked to D D is exatecan;

p is from 1 to 8, for example between 4 and 8, preferably between 6 and 8, and for example p is between 7 and 8.

Another object of the disclosure relates to the above ADCs, for use as a medicament, preferably for use in the treatment of a tumor, for example a solid tumor, more specifically selected from the group consisting of ovarian cancer, breast cancer, lung cancer, or mesothelioma.

Another object of the disclosure relates to the use of above ADCs, in the preparation of a medicament or pharmaceutical composition for the treatment of a tumor, for example a solid tumor, more specifically selected from the group consisting of ovarian cancer, breast cancer, lung cancer, or mesothelioma.

In specific embodiments, the ADCs may be preferably used in the treatment of a cancer selected from the group consisting of ovarian cancer, triple negative breast cancer, and non-small cell lung cancer.

LEGENDS OF THE FIGURES

FIG. 4 represents in vitro ELISA binding experiments of conjugates against recombinant human folate receptor alpha protein, according to example 7.

FIG. 5 represents in vitro surface plasmon resonance (SPR) binding experiments of conjugates against recombinant human folate receptor alpha protein, according to example 8.

FIG. 6 represents in vitro folate receptor alpha positive cancer cells binding affinity of conjugates, according to example 9.

FIG. 22 represents in vivo cynomolgus monkey dose-range-finding toxicology study, according to example 16.

DETAILED DESCRIPTION

Definitions

Figure 1:
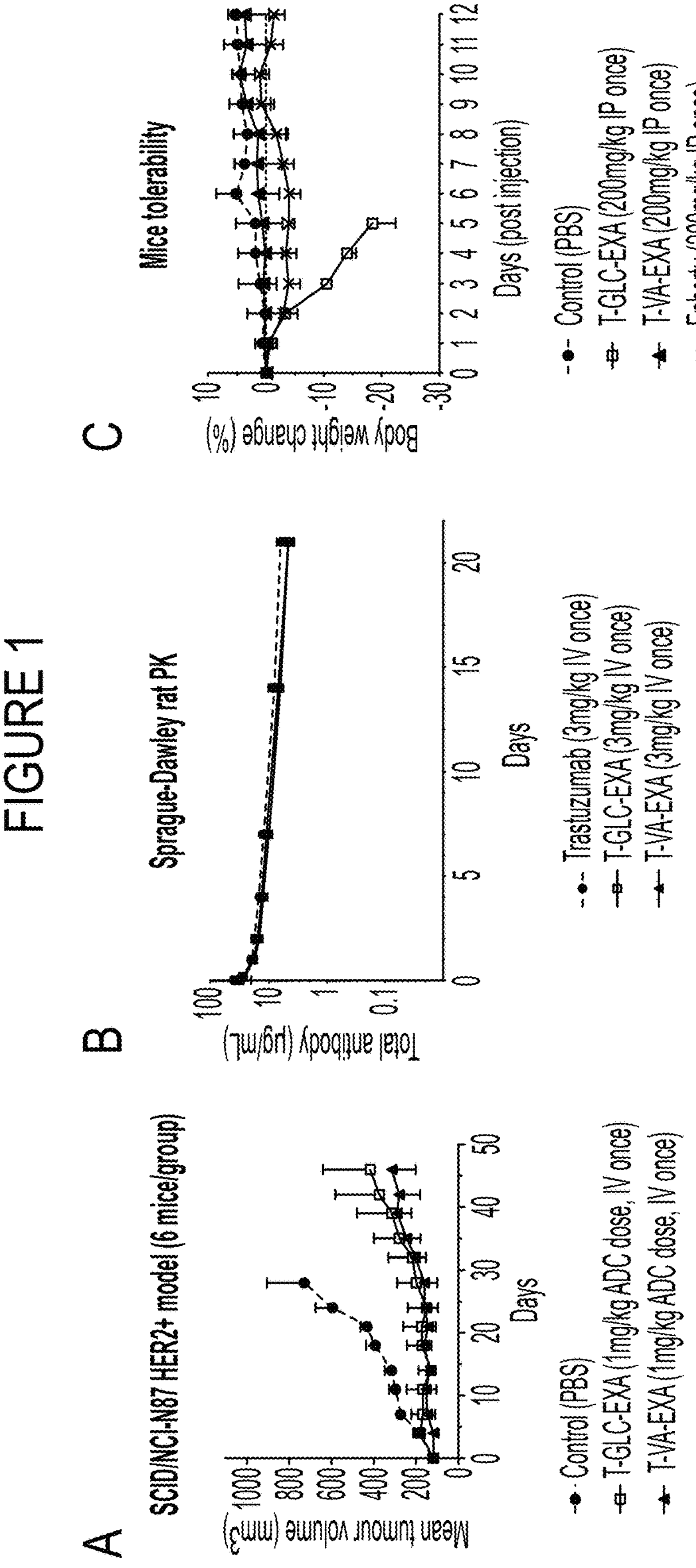
FIG. 1 represents preclinical rodent efficacy, pharmacokinetic and tolerability data of conjugates, according to example 4.

In order that the present disclosure may be more readily understood, certain terms are first defined. Additional definitions are set forth throughout the detailed description.

The term "FRα" or "folate receptor alpha" refers to the human folate receptor alpha as defined in SEQ ID NO: 12, unless otherwise described. This sequence corresponds to the amino acid sequence of Folate receptor alpha as encoded by FOLR1 gene (*Homo sapiens*) also available in UniprotKB under entry P15328 (FOLR1_HUMAN).

The term "antibody" as referred to herein includes whole antibodies and any antigen binding fragments (i.e. "antigen-binding portion") or single chains thereof. A naturally occurring "antibody" is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g. effector cells) and the first component (Clq) of the classical complement system. The term "antigen-binding portion" of an antibody (or simply "antigen portion"), as used herein, refers to full length or one or more fragments of an antibody that retain the ability to specifically bind to an antigen (e.g. a portion of FRα). It has been shown that the antigen-binding function of an antibody can be performed by fragments of a full-length antibody. Examples of binding fragments encompassed within the term "antigen-binding portion" of an antibody include a Fab fragment, a monovalent fragment consisting of the VL, VH, CL and CH1 domains; a $F(ab)_2$ fragment; a bivalent fragment comprising two Fab fragments linked by a disulfide bridge at the hinge region; a Fd fragment consisting of the VH and CH1 domains; a Fv fragment consisting of the VL and VH domains of a single arm of an antibody; a UniBody consisting of a single arm with a modified IgG heavy chain, for example IgG4, at the hinge region, a domain antibody fragment (Ward et al., 1989 Nature 341:544-546), or a nanobody fragment which consists of a VH domain; and an isolated complementarity determining region (CDR); or any fusion proteins comprising such antigen-binding portion. Furthermore, although the two domains of the Fv fragment, VL and VH, are coded for by separate genes, they can be joined, using recombinant methods, by a synthetic linker that enables them to be made as a single chain protein in which the VL and VH regions pair to form monovalent molecules (known as single chain Fv (scFv); see e.g., Bird et al., 1988 Science 242:423-426; and Huston et al., 1988 Proc. Natl. Acad. Sci. 85:5879-5883). Such single chain antibodies are also intended to be encompassed within the term "antigen binding portion" of an antibody. These antibody fragments are obtained using conventional techniques known to those of skill in the art, and the fragments are screened for utility in the same manner as are intact antibodies.

An "isolated antibody", as used herein, refers to an antibody that is substantially free of other antibodies having different antigenic specificities (e.g. an isolated antibody that specifically binds to FRα is substantially free of antibodies that specifically bind to other antigens than FRα). An isolated antibody that specifically binds to FRα may, however, have cross-reactivity to other antigens, such as FRα molecules from other species. Moreover, an isolated antibody may be substantially free of other cellular material and/or chemicals.

The phrases "an antibody recognizing an antigen" and "an antibody specific for an antigen" are used interchangeably herein with the term "an antibody which binds specifically to an antigen".

The terms "monoclonal antibody" or "monoclonal antibody composition" as used herein refers to a preparation of antibody molecules of single molecular composition. A monoclonal antibody composition displays a single binding specificity and affinity for a particular epitope.

As used herein, "isotype" refers to the antibody class (e.g. IgM, IgE, IgG such as IgG1 or IgG4) that is provided by the heavy chain constant region genes.

The term "$K_D$", as used herein, is intended to refer to the equilibrium dissociation constant, which is obtained from the ratio of $k_{off}$ to $k_{on}$ (i.e. $k_{off}/k_{on}$) and is expressed as a molar concentration (M). The $K_D$ value relates to the concentration of antibody (the amount of antibody needed for a particular experiment) and so the lower the $K_D$ value (lower concentration) and thus the higher the affinity of the antibody. $K_D$ values for antibodies can be determined using methods well established in the art. Preferred methods for determining the $K_D$ values of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., 1992, 1993, and Muller, Meth Enzymol 1983, which references are entirely incorporated herein by reference. A method for determining the $K_D$ of an antibody is by using surface plasmon resonance, or by using a biosensor system such as a Biacore® (see also for detailed information regarding affinity assessment Rich R L, Day Y S, Morton T A, Myszka D G. High-resolution and high-throughput protocols for measuring drug/human serum albumin interactions using BIACORE®. Anal Biochem. 2001).

The term "$k_{assoc}$" or "$k_a$", or "$k_{on}$" as used herein, is intended to refer to the association rate of a particular antibody-antigen interaction, whereas the term "$k_{dis}$" or "$k_d$,", or $k_{off}$ as used herein, is intended to refer to the dissociation rate of a particular antibody-antigen interaction.

As used herein, the term "affinity" refers to the strength of interaction between antibody and antigen at single antigenic sites. Within each antigenic site, the variable region of the antibody "arm" interacts through weak non-covalent forces with the antigen at numerous sites; the more interactions, the stronger the affinity.

As used herein, an antibody or a protein that "specifically binds to an antigen", for example that "specifically binds to FRα" is intended to refer to an antibody which detectably bind an epitope presented on an antigen, such as a FRα in the present disclosure. It is typically intended to refer to an antibody, or ADC, that binds to human FRα with a $K_D$ of 200 nM or less, 100 nM or less, 50 nM, 40 nM or less, or about 30 nM. Typically, the $K_D$ is comprised between 103 PM and 200 nM, notably between 0.1 pM and 100 nM, notably between 0.1 pM and 50 nM, or between 1 PM and 50 nM notably between 1 PM and 30 nM, between 10 PM and 50 nM, between 0.1 nM and 200 nM or between 0.1 nM and 100 nM, or between 1 nM and 50 nM, notably between 1 nM and 30 nM. Typically, an ADC of the present disclosure is specific for FRα and has a $K_D$ as above defined.

As used herein, the term "host cell" refers to prokaryotic or eukaryotic cells. Eukaryotic cells, for example mammalian host cells, yeast or filamentous fungi, are preferred, and in particular mammalian cells, because they are more likely than prokaryotic cells to assemble and secrete a properly folded and immunologically active antibody.

As used herein, the term "ADCC" or "antibody dependent cell cytotoxicity" activity refers to cell depleting activity. ADCC activity can be measured by ADCC assays commercially available, for example, ADCC Reporter Bioassay as commercialized by Promega under Ref #G7015.

As used herein, the term "subject" includes any human or nonhuman animal. The term "nonhuman animal" includes all vertebrates, e.g. mammals and non-mammals, such as nonhuman primates, sheep, dogs, cats, horses, cows, chickens, amphibians, reptiles, . . . . The term "subjects" also encompasses the term "patient".

As used herein, the term "drug" or D in the formula (I) of the ADC also refers to "a payload", i.e. a moiety that is conjugated to an antibody (or a fragment). The drug D is not to be construed as limited to classical chemical therapeutic agent. For example, D can encompass a protein, a peptide or a polypeptide possessing a desired biological activity. Preferably, it refers to a therapeutic moiety, such as a cytotoxin. A "cytotoxin" or "cytotoxic agent" includes any agent that is detrimental to (e.g. kills) cells.

Unless specified otherwise, the present disclosure encompasses the compounds or drug or cytotoxin as described herein and, their tautomers, enantiomers, diastereomers, racemates or mixtures thereof, and their hydrates, esters, solvates or pharmaceutically acceptable salts.

Any formula given herein is also intended to represent unlabeled as well as isotopically labeled forms of the compounds, like deuterium labeled compounds or $^{14}C$-labeled compounds.

The terms "pharmaceutically acceptable salts" refer to salts that retain the biological effectiveness and properties of the compounds of this disclosure and, which typically are not biologically or otherwise undesirable. In many cases, the compounds of the disclosure are capable of forming acid and/or base salts by virtue of the presence of amino and/or carboxyl groups or groups similar thereto. Pharmaceutically acceptable acid addition salts can be formed with organic acids and/or inorganic acids.

Pharmaceutically acceptable base addition salts can be formed with organic bases and/or inorganic bases. Such salts are well-known from those skilled in the art.

The term connector unit refers to a component that connects different parts of the compound together, for example, the connector can connect Ab to a spacer, or a spacer to the amide function —CO—NR1-. The connector is a scaffold bearing attachment sites for components of the antibody-drug-conjugate, namely Ab, the spacer, the hydrophobicity masking entity, and/or the amide function —CO—NR1-.

From his knowledge, the one skilled in the art is capable to select a connector which is appropriate. Non-exhaustive listing of connectors includes: aminoacids, for example lysine, glutamic acid, aspartic acid, serine, tyrosine, cysteine, selenocysteine, glycine, homoalanine; amino alcohols; amino aldehydes; polyamines or any combination thereof. Advantageously, the connector unit $X_1$ and/or $X_2$ is one or more natural or non-natural aminoacids. In one embodiment, the connector unit $X_1$ and/or $X_2$ is selected from glutamic acid, lysine and glycine. The connector units $X_1$ and $X_2$ can be independently selected from the group consisting of one or more amino acid(s), one or more N-substituted amino acid, optionally substituted polyether, $C_1$-$C_{12}$ alkylene, arylene having 6 to 10 ring atoms, $C_3$-$C_8$ cycloalkylene, heterocycloalkylene having 5 to 10 ring atoms, heteroarylene having 5 to 10 ring atoms, $C_2$-$C_{10}$ alkenylene, and any combination thereof, said alkylene and alkenylene being optionally interrupted by one or more heteroatoms or chemical groups selected from —O—, —S—, —C(O)—, —NR"—, —C(O)NR"—, —NR"—C(O)—, —NR"—C(O)—NR"—, —NR"—C(O)—O—, —O—C(O)NR"— and triazole, and said alkylene, arylene, cycloalkylene, heterocycloalkylene, heteroarylene, and alkenylene being optionally substituted with one or more of the substituents selected from: halogen, oxo, —OH, $—NO_2$, —CN, $C_1$-$C_6$ alkyl, $C_3$-$C_6$ cycloalkyl, heterocyclyl having 5 to 10 ring atoms, aryl having 6 to 10 ring atoms, heteroaryl having 5 to 10 ring atoms, $C_1$-$C_6$ alkoxy, $C_1$-$C_6$ haloalkyl, $C_1$-$C_6$ haloalkoxy, —(CO)—R', —O—(CO)—R', —(CO)—O—R', —(CO)—NR"R", —NR"—(CO)—R', and —NR"R"; R', R" and R" being independently selected from H and $C_1$-$C_6$ alkyl.

Examples of connector units include optionally substituted polyether, aminoacids, benzyl groups, amines, ketones,

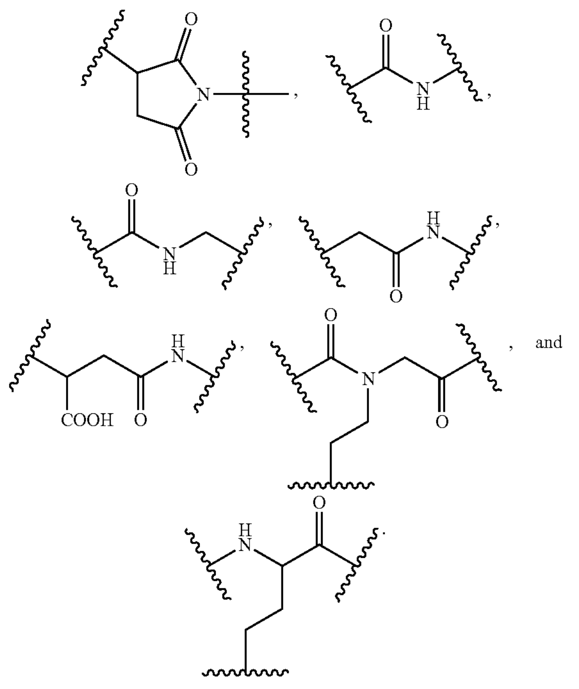

In particular, the connector unit can be divalent or trivalent. For example, $X_2$ can be a trivalent connector unit when the hydrophobicity masking entity K is present.

The term "aminoacids" refers to natural or non-natural aminoacids. The CO moiety of the —CONR1- or —CONR1'- group can be considered as part of the $X_2$ connector unit when $X_2$ consists of one or more aminoacids. Non-exhaustive listing of aminoacids includes lysine, glutamic acid, aspartic acid, serine, tyrosine, cysteine, selenocysteine, glycine, and homoalanine.

A spacer is a divalent arm that covalently binds two components of the antibody-drug-conjugate, such as the 2 connector units.

Non-exhaustive listing of spacer units includes: alkylene, heteroalkylene (so an alkylene interrupted by at least one heteroatom selected from Si, N, O and S); alkoxy; polyether such as polyalkylene glycol and typically polyethylene glycol; one or more natural or non-natural aminoacids such as glycine, alanine, proline, valine, N-methylglycine; $C_3$-$C_8$ heterocyclo; $C_3$-$C_8$ carbocyclo; arylene, and any combination thereof. For example, a spacer is a divalent linear alkylene group, preferably $(CH_2)_4$.

For example, the spacer can be selected from the group consisting of —$C_1$-$C_{10}$ alkylene-, —$C_1$-$C_{10}$ heteroalkylene-, —$C_3$-$C_8$ carbocyclo-, —O—($C_1$ $C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$ alkylene-, —$C_1$-$C_{10}$ alkylene-C(═O)—, —$C_1$-$C_{10}$ heteroalkylene-C(═O)—, —$C_3$-$C_8$ carbocyclo-C(═O)—, —O—($C_1$-$C_8$ alkyl)-C(═O)—, -arylene-C(═O)—, —$C_1$-$C_{10}$ alkylene-arylene-C(═O)—, -arylene-$C_1$-$C_{10}$ alkylene-C(═O)—, —$C_1$-$C_{10}$ alkylene-($C_3$-$C_8$carbocyclo)-C(═O)—, —($C_3$-$C_8$ carbocyclo)-$C_1$-$C_{10}$ alkylene-C(═O)—, —$C_3$-$C_8$ heterocyclo-C(═O)—, —$C_1$-$C_{10}$ alkylene-($C_3$-$C_8$heterocyclo)-C(═O)—, —($C_3$-$C_8$ heterocyclo)-$C_1$-$C_{10}$ alkylene-C(═O)—, —$C_1$-$C_{10}$ alkylene-NH—, —$C_1$-$C_{10}$ heteroalkylene-NH—, —$C_3$-$C_8$ carbocyclo-NH—, —O—($C_1$-$C_8$ alkyl)-NH—, -arylene-NH—, —$C_1$-$C_{10}$ alkylene-arylene-NH—, -arylene-$C_1$-$C_{10}$ alkylene-NH—, —$C_1$-$C_{10}$ alkylene-($C_3$-$C_8$ carbocyclo)-NH—, —($C_3$-$C_8$ carbocyclo)-$C_1$-$C_{10}$ alkylene-NH—, —$C_3$-$C_8$heterocyclo-NH—, —$C_1$-$C_{10}$ alkylene-($C_3$-$C_8$ heterocyclo)-NH—, —($C_3$-$C_8$ heterocyclo)-$C_1$-$C_{10}$ alkylene-NH—, —$C_1$-$C_{10}$ alkylene-S—, —$C_1$-$C_{10}$ heteroalkylene-S—, —$C_3$-$C_8$carbocyclo-S—, —O—($C_1$-$C_8$ alkyl)-)—S—, -arylene-S—, —$C_1$-$C_{10}$ alkylene-arylene-S—, -arylene-$C_1$-$C_{10}$ alkylene-S—, —$C_1$-$C_{10}$ alkylene-($C_3$-$C_8$ carbocyclo)-S—, —($C_3$-$C_8$ carbocyclo)-$C_1$-$C_{10}$ alkylene-S—, —$C_3$-$C_8$ heterocyclo-S—, —$C_1$-$C_{10}$ alkylene-($C_3$-$C_8$ heterocyclo)-S—, —($C_3$-$C_8$ heterocyclo)-$C_1$-$C_{10}$ alkylene-S—, —$C_1$-$C_{10}$ alkylene-O—C(═O)—, —$C_3$-$C_8$ carbocyclo-O—C(═O)—, —O—($C_1$-$C_8$ alkyl)-O—C(═O)—, -arylene-O—C(═O)—, —$C_1$-$C_{10}$ alkylene-arylene-O—C(═O)—, -arylene-$C_1$-$C_{10}$ alkylene-O—C(═O)—, —$C_1$-$C_{10}$ alkylene-($C_3$-$C_8$carbocyclo)-O—C(═O)—, —($C_3$-$C_8$ carbocyclo)-$C_1$-$C_{10}$ alkylene-O—C(═O)—, —$C_3$-$C_8$ heterocyclo-O—C(═O)—, —$C_1$-$C_{10}$ alkylene-($C_3$-$C_8$heterocyclo)-O—C(═O)—, and —($C_3$-$C_8$ heterocyclo)-$C_1$-$C_{10}$ alkylene-O—C(═O)—.

Any of the groups mentioned above is optionally substituted with one or more of the substituents selected from: —X, —R', —O, —OR', ═O, —SR', —S, —NR'$_2$, —NR'$_3^+$, ═NR', —$CX_3$, —CN, —OCN, —SCN, —N═C═O, —NCS, —NO, —$NO_2$, ═$N_2$, —$N_3$, —NR'C(═O) R', —C(═O) R', —C(═O)NR'$_2$, —$SO_3$, —$SO_3H$, —S(═O)$_2$ R', —OS(═O)$_2$OR', —S(═O)$_2$NR', —S(═O) R', —OP(═O)(OR')$_2$, —P(═O)(OR')$_2$, —$PO_3$, —$PO_3H_2$, —C(═O) X, —C(═S) R', —$CO_2$R', —$CO_2$, —C(═S)OR', C(═O) SR', C(═S)SR', C(═O)NR'$_2$, C(═S)NR'$_2$, and C(═NR') NR'$_2$, where each X is independently a halogen: —F, —Cl, —Br, or —I; and each R' is independently —H, —$C_1$-$C_{20}$ alkyl, —$C_6$-$C_{10}$ aryl, or —$C_3$-$C_{10}$ heterocycle.

As used herein, the term "alkyl" refers to a monovalent saturated hydrocarbon chain (having straight or branched chain). For example, alkyl refers to $C_1$-$C_{20}$ alkyl. Preferably, the alkyl is a "lower alkyl", i.e. an alkyl group having 1, 2, 3, 4, 5 or 6 carbons (straight or branched chain $C_1$-$C_6$ alkyl group). For example, this includes methyl, ethyl, n-propyl, i-propyl, n-butyl, i-butyl, sec-butyl, tert-butyl, n-pentyl, n-hexyl, and the like.

Alkylene, used alone or as part of alkylene glycol for example, refers to a divalent saturated, straight-chained or branched alkyl group as defined herein.

Alkenyl and alkynyl refer to at least partially unsaturated, straight-chained or branched hydrocarbon group having 2-20 carbon atoms, preferably 2-12, more preferably 2-6, especially 2-4. An alkenyl group comprises at least one C═C double bond; an alkynyl group comprises at least one C≡C triple bond.

As used herein, the terms "$C_3$-$C_8$ cycloalkyl" or "carbocycle" refer to a saturated or unsaturated cyclic group having 3 to 8 carbon atoms, preferably 3 to 6. The cycloalkyl can have a single ring or multiple rings fused together. The cycloalkyl can also include spirocyclic rings. Suitable cycloalkyl groups include cyclopropyl, cyclobutyl, cyclopentyl and cyclohexyl.

As used herein, the terms "$C_3$-$C_8$ cycloalkylene" or "carbocyclo" refer to a divalent cycloalkyl as defined herein.

As used herein, the term "halogen" refers to a fluoro (—F), chloro (—Cl), bromo (—Br), or iodo (—I) group.

As used herein, the terms "$C_1$-$C_6$ haloalkyl" refer to a $C_1$-$C_6$ alkyl as defined herein that is substituted by one or more halogen group as defined herein. Suitable $C_1$-$C_6$ haloalkyl groups include trifluoromethyl and dichloromethyl.

As used herein, the term "heteroalkyl", refers to a straight or branched hydrocarbon chain consisting of 1 to 12 carbon atoms, preferably 1 to 10, more preferably 1 to 6 carbon atoms, and from one to three heteroatoms selected from the group consisting of O, N, Si and S, and wherein the nitrogen and sulfur atoms may optionally be oxidized (for example: a sulfoxide or a sulfone) and the nitrogen heteroatom may optionally be quaternized. The heteroatom(s) O, N and S may be placed at any interior position of the heteroalkyl group or at the position at which the alkyl group is attached to the remainder of the molecule.

Heteroalkylene refers to a divalent heteroalkyl as defined above. For heteroalkylene groups, heteroatoms can also occupy either or both of the chain termini.

As used herein, the terms "$C_1$-$C_6$ alkoxy" refer to a —O-alkyl group, wherein the alkyl group is a $C_1$-$C_6$ alkyl as defined herein. Suitable $C_1$-$C_6$ alkoxy groups include methoxy, ethoxy, propoxy.

As used herein, the terms "$C_1$-$C_6$ haloalkoxy" refer to a $C_1$-$C_6$ alkoxy group as defined herein, that is substituted by one or more halogen group as defined herein. Suitable haloalkoxy include trifluoromethoxy.

As used herein, the terms "aryl having 6 to 10 ring atoms" refer to a polyunsaturated, aromatic hydrocarbyl group having a single ring or multiple aromatic rings fused together, containing 6 to 10 ring atoms, wherein at least one ring is aromatic. The aromatic ring may optionally include one to two additional rings (cycloalkyl, heterocyclyl or heteroaryl as defined herein) fused thereto. Suitable aryl groups include phenyl, naphthyl and phenyl ring fused to a heterocyclyl, like benzopyranyl, benzodioxolyl, benzodioxanyl and the like.

Arylene refers to a divalent aryl group as defined above.

As used herein, the terms "heteroaryl having 5 to 10 ring atoms" refer to a polyunsaturated, aromatic ring system having a single ring or multiple aromatic rings fused together or linked covalently, containing 5 to 10 atoms, wherein at least one ring is aromatic and at least one ring atom is a heteroatom selected from N, O and S. The nitrogen and sulfur heteroatoms may optionally be oxidized and the nitrogen heteroatoms may optionally be quaternized. Such rings may be fused to an aryl, cycloalkyl or heterocyclyl ring. Non-limiting examples of such heteroaryl, include: furanyl, thiophenyl, pyrrolyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, indolyl, isoindolyl, benzofuranyl, isobenzofuranyl, benzothiophenyl, isobenzothiophenyl, indazolyl, benzimidazolyl, benzoxazolyl, purinyl, benzothiadiazolyl, quinolinyl, isoquinolinyl, cinnolinyl, quinazolinyl and quinoxalinyl.

As used herein, the terms "heterocyclyl having 3 to 10 ring atoms", "heterocycloalkyl having 3 to 10 ring atoms" or "heterocyclyl" refer to a saturated or unsaturated cyclic group having 3 to 10 ring atoms, preferably 3 to 8 ring atoms, wherein at least one ring atom is a heteroatom selected from N, O and S. The nitrogen and sulfur heteroatoms may optionally be oxidized and the nitrogen heteroatoms may optionally be quaternized.

The heterocycle can include fused or bridged rings as well as spirocyclic rings. Examples of heterocycle include, but are not limited to, tetrahydropyridyl, piperidinyl, morpholinyl, tetrahydrofuranyl, tetrahydrothienyl, piperazinyl, 1-azepanyl, imidazolinyl, 1,4-dioxanyl and the like.

As used herein, the terms "heterocyclo" or "heterocycloalkylene" refer to a divalent heterocycle as defined herein.

Furthermore, the terms alkyl, alkenyl, alkynyl, aryl, alkylene, arylene, heteroalkyl, heteroalkylene, $C_3$-$C_8$ carbocycle, $C_3$-$C_8$ carbocyclo, $C_3$-$C_8$ heterocycle, $C_3$-$C_8$ heterocyclo, polyether refer to optionally substituted groups with one or more of the substituents selected from: —X, —R', —O, —OR', =O, —SR', —S, —NR'$_2$, —NR'3, =NR', —$CX_3$, —CN, —OCN, —SCN, —N=C=O, —NCS, —NO, —$NO_2$, =$N_2$, —$N_3$, —NRC(=O) R', —C(=O) R', —C(=O)NR'$_2$, —$SO_3$, —$SO_3H$, —S(=O)$_2$R', —OS(=O)$_2$ OR', —S(=O)$_2$NR', —S(=O) R', —OP(=O)(OR')$_2$, —P(=O)(OR')$_2$, —$PO_3$, —$PO_3H_2$, —C(=O) R', —C(=O) X, —C(=S) R', —$CO_2$R', —$CO_2$, —C(=S)OR', C(=O) SR', C(=S) SR', C(=O)NR'$_2$, C(=S)NR'$_2$, and C(=NR')NR'$_2$, where each X is independently a halogen: —F, —Cl, —Br, or —I; and each R' is independently-H, —$C_1$-$C_{20}$ alkyl, —$C_6$-$C_{10}$ aryl, or —$C_3$-$C_{10}$ heterocycle.

As used herein, the term "polyether" refers to a polymer containing ether linkage. The number of ether moieties in the polyether may be comprised between 2 and 100, preferably between 2 and 25, in particular between 2 and 10. Examples of polyether include polyethylene glycol.

An electron withdrawing group refers to an atom or group that draws electron density from neighboring atoms towards itself, usually by resonance or inductive effect. Electron withdrawing groups include halogens, haloalkyl (like —$CF_3$), —CN, —$SO_3H$, —$NO_2$, and —C(O) R groups, with R=H, OH, or alkoxy. Advantageously, the electron withdrawing group is —$NO_2$. In an embodiment, the electron-withdrawing group is in ortho position with regard to the Y-T substituent of the phenyl ring.

As used herein, the terms "protecting group" refer to a chemical substituent which can be selectively removed by readily available reagents which do not attack the regenerated functional group or other functional groups in the molecule. Suitable protecting groups are known in the art and continue to be developed. Suitable protecting groups may be found, for example in Wutz et al. ("Greene's Protective Groups in Organic Synthesis, Fourth Edition," Wiley-Interscience, 2007). Protecting group for protection of the amino group as described by Wutz et al. (pages 696-927), are used in certain embodiments. Representative examples of amino protecting groups include, but are not limited to, t-butyloxycarbonyl (Boc), 9-fluorenyl methoxycarbonyl (Fmoc), Acetyl (Ac), carboxybenzyl group (Cbz), benzyl group (Bn), allyl, trifluoroacetyl, allyloxy carbonyl (Alloc) group and 2,2,2-trichloroethoxycarbonyl (Troc).

A hydrophobicity masking entity refers to a group that can reduce the apparent hydrophobicity of the compound. The hydrophobicity masking entity can be selected from polysarcosine and polyethylene glycol. The number of ethylene glycol or sarcosine moieties may vary in a wide range. For instance, the number of ethylene glycol or sarcosine moieties in the hydrophobicity masking entity may be comprised between 2 and 500, preferably between 5 and 100, in particular between 5 and 25. In an embodiment, the hydrophobicity masking entity is a polysarcosine comprising from 6 to 24 sarcosine moieties, preferably comprising from 10 to 12 sarcosine moieties.

As used herein, the term "bonded" refers to a linkage. This linkage is also represented by the dash "-" in formula (I). Linkage may be a covalent bond, or a non-covalent interaction such as through electrostatic forces. Preferably, bonds are covalent bonds. As used herein, the "wavy lines" on formulas represent the attachment sites between each part (Ab, L, Z, X and D) of the ADC of the disclosure.

As used herein, the term "treat" "treating" or "treatment" refers to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease or reducing or alleviating one or more symptoms of the disease. In particular, with reference to the treatment of a tumor, the term "treatment" may refer to the inhibition of the growth of the tumor, or the reduction of the size of the tumor.

As used herein, a "therapeutically efficient amount" or "effective amount" of an ADC is an amount sufficient to perform a specifically stated purpose, for example to product a therapeutic effect after administration, such as inhibition or reduction in tumor growth rate or tumor volume, a reduction in a symptom of cancer or some indicia of treatment efficacy. In the case of cancer, a therapeutically effective amount of ADC can reduce the number of cancer cells, reduce the tumor size, inhibit (e.g. slow or stop) tumor metastasis, inhibit (e.g. slow or stop) tumor growth, and/or relieve one or more symptoms.

As used herein, the percent identity between the two sequences is a function of the number of identical positions shared by the sequences (i. e., % identity=number of identical positions/total number of positions×100), taking into account the number of gaps, and the length of each gap, which need to be introduced for optimal alignment of the two sequences. The comparison of sequences and determination of percent identity between two sequences can be accomplished using a mathematical algorithm, as described below.

The percent identity between two amino acid sequences can be determined using the Needleman and Wunsch algorithm (NEEDLEMAN, and Wunsch).

The percent identity between two nucleotide or amino acid sequences may also be determined using for example algorithms such as EMBOSS Needle (pair wise alignment; available at www.ebi.ac.uk). For example, EMBOSS Needle may be used with a BLOSUM62 matrix, a "gap open penalty" of 10, a "gap extend penalty" of 0.5, a false "end gap penalty", an "end gap open penalty" of 10 and an "end gap extend penalty" of 0.5. In general, the "percent identity" is a function of the number of matching positions divided by the number of positions compared and multiplied by 100. For instance, if 6 out of 10 sequence positions are identical between the two compared sequences after alignment, then the identity is 60%. The % identity is typically determined over the whole length of the query sequence on which the analysis is performed. Two molecules having the same primary amino acid sequence or nucleic acid sequence are identical irrespective of any chemical and/or biological modification.

The Antibody Ab for Use in Making the ADCs of the Disclosure

The antibody Ab for use in making the ADCs of the disclosure are anti-folate receptor alpha (FRα) antibodies which binds specifically to SEQ ID NO:12.

Preferably, such antibodies include the following antibodies, isolated and structurally characterized by their variable heavy and light chain amino acid sequences and human constant isotype as described in the Table 1 below:

TABLE 1

Variable heavy and light chain amino acid sequences

| Antibody | VH Amino acid sequence | VL Amino acid sequence | Isotype constant region |
|---|---|---|---|
| mAb1 farletuzumab-LALA | SEQ ID NO: 7 | SEQ ID NO: 8 | IgG1 LALA |
| mAb2 farletuzumab | SEQ ID NO: 7 | SEQ ID NO: 8 | IgG1 |

IgG1 LALA corresponds to the mutant IgG1 Fc region including the amino acid substitutions from Leucine to Alanine at residues 234 and 235 also disclosed in J. Virol 2001 December; 75 (24): 12161-8 by Hezareh et al.

Full length light and heavy chains and corresponding coding sequences of mAb1 is shown in the Table 2 below.

TABLE 2

Full length heavy and light chain Amino acid and DNA coding sequences

| Antibody | Amino acid sequence | DNA coding sequence |
|---|---|---|
| mAb1 farletuzumab-LALA | Heavy Chain: SEQ ID NO: 9<br>Light Chain: SEQ ID NO: 10 | Heavy Chain: SEQ ID NO: 13<br>Light Chain: SEQ ID NO: 14 |

Examples of the amino acid sequences of the VH CDR1s (also called HCDR1), VH CDR2s (also called HCDR2), VH CDR3s (also called HCDR1), VL CDR1s (also called LCDR1), VL CDR2s (also called LCDR2), VL CDR3s (also called HCDR3) of mAb1 antibody are shown in Table 3.

In Table 3, the CDR regions of some antibodies of the present disclosure are delineated using the Kabat system. For the ease of reading, the CDR regions are called hereafter HCDR1, HCDR2, HCDR3, LCDR1, LCDR2, LCDR3 respectively.

TABLE 3

CDR regions of mAb1 according to Kabat (also disclosed in WO2017151979)

| Original antibody | HCDR1 | HCDR2 | HCDR3 | LCDR1 | LCDR2 | LCDR3 |
|---|---|---|---|---|---|---|
| mAb1 farletuzumab-LALA | SEQ ID NO: 1 | SEQ ID NO: 2 | SEQ ID NO: 3 | SEQ ID NO: 4 | SEQ ID NO: 7 | SEQ ID NO: 6 |

Tables 4 and 5 below provide useful amino acid and nucleotides sequences relative to antibodies of ADC.

TABLE 4

| Brief description of useful amino acid and nucleotide sequences for practicing the invention | | |
|---|---|---|
| SEQ ID NO: | Type* | Description |
| 1 | aa | HCDR1 mAb1 (farletuzumab) |
| 2 | aa | HCDR2 mAb1 (farletuzumab) |
| 3 | aa | HCDR3 mAb1 (farletuzumab) |
| 4 | aa | LCDR1 mAb1 (farletuzumab) |
| 5 | aa | LCDR2 mAb1 (farletuzumab) |
| 6 | aa | LCDR3 mAb1 (farletuzumab) |
| 7 | aa | VH mAb1 (farletuzumab) |
| 8 | aa | VL mAb1 (farletuzumab) |
| 9 | aa | Heavy Chain (full length) of Fc-silent farletuzumab-LALA) |
| 10 | aa | Light Chain (full length) of farletuzumab |
| 11 | aa | Heavy Chain (full length) of farletuzumab |
| 12 | aa | Human folate receptor alpha (FRa) |
| 13 | nt | Heavy Chain (full length) of mAb1 (Fc-silent farletuzumab-LALA) |
| 14 | nt | Light Chain (full length) of farletuzumab |
| 15 | nt | Heavy Chain (full length) of farletuzumab) |
| 16 | aa | Heavy chain (full length) of Mirvetuximab |
| 17 | aa | Light Chain (full length) of Mirvetuximab |

*aa is amino acid sequence
nt is nucleotide sequence

TABLE 5

| Useful amino acid and nucleotide sequences for practicing the invention | |
|---|---|
| SEQ ID | Detailed sequences |
| 1 | GYGLS |
| 2 | MISSGGSYTYYADSVKG |
| 3 | HGDDPAWFAY |
| 4 | SVSSSISSNNLH |
| 5 | GTSNLAS |
| 6 | QQWSSYPYMYT |
| 7 | EVQLVESGGGVVQPGRSLRLSCSASGFTFSGYGLSWVRQAPGKGLEW VAMISSGGSYTYYADSVKGRFAISRDNAKNTLFLQMDSLRPEDTGVYFC ARHGDDPAWFAYWGQGTPVTVSS |
| 8 | DIQLTQSPSSLSASVGDRVTITCSVSSSISSNNLHWYQQKPGKAPKPWIY GTSNLASGVPSRFSGSGSGTDYTFTISSLQPEDIATYYCQQWSSYPYMY TFGQGTKVEIK |
| 9 | EVQLVESGGGVVQPGRSLRLSCSASGFTFSGYGLSWVRQAPGKGLEW VAMISSGGSYTYYADSVKGRFAISRDNAKNTLFLQMDSLRPEDTGVYFC ARHGDDPAWFAYWGQGTPVTVSSASTKGPSVFPLAPSSKSTSGGTAAL GCLVKDYFPEPVTVSWNSGALTSGVHTFPAVLQSSGLYSLSSVVTVPSS SLGTQTYICNVNHKPSNTKVDKKVEPKSCDKTHTCPPCPAPEAAGGPSV FLFPPKPKDTLMISRTPEVTCVVVDVSHEDPEVKFNWYVDGVEVHNAKT KPREEQYNSTYRVVSVLTVLHQDWLNGKEYKCKVSNKALPAPIEKTISKA KGQPREPQVYTLPPSRDELTKNQVSLTCLVKGFYPSDIAVEWESNGQPE NNYKTTPPVLDSDGSFFLYSKLTVDKSRWQQGNVFSCSVMHEALHNHY TQKSLSLSPGK |
| 10 | DIQLTQSPSSLSASVGDRVTITCSVSSSISSNNLHWYQQKPGKAPKPWIY GTSNLASGVPSRFSGSGSGTDYTFTISSLQPEDIATYYCQQWSSYPYMY TFGQGTKVEIKRTVAAPSVFIFPPSDEQLKSGTASVVCLLNNFYPREAKV QWKVDNALQSGNSQESVTEQDSKDSTYSLSSTLTLSKADYEKHKVYAC EVTHQGLSSPVTKSFNRGEC |
| 11 | EVQLVESGGGVVQPGRSLRLSCSASGFTFSGYGLSWVRQAPGKGLEW VAMISSGGSYTYYADSVKGRFAISRDNAKNTLFLQMDSLRPEDTGVYFC ARHGDDPAWFAYWGQGTPVTVSSASTKGPSVFPLAPSSKSTSGGTAAL GCLVKDYFPEPVTVSWNSGALTSGVHTFPAVLQSSGLYSLSSVVTVPSS SLGTQTYICNVNHKPSNTKVDKKVEPKSCDKTHTCPPCPAPELLGGPSV FLFPPKPKDTLMISRTPEVTCVVVDVSHEDPEVKFNWYVDGVEVHNAKT KPREEQYNSTYRVVSVLTVLHQDWLNGKEYKCKVSNKALPAPIEKTISKA KGQPREPQVYTLPPSRDELTKNQVSLTCLVKGFYPSDIAVEWESNGQPE NNYKTTPPVLDSDGSFFLYSKLTVDKSRWQQGNVFSCSVMHEALHNHY TQKSLSLSPGK |
| 12 | MAQRMTTQLLLLLVWVAVVGEAQTRIAWARTELLNVCMNAKHHKEKPG PEDKLHEQCRPWRKNACCSTNTSQEAHKDVSYLYRFNWNHCGEMAPA CKRHFIQDTCLYECSPNLGPWIQQVDQSWRKERVLNVPLCKEDCEQW WEDCRTSYTCKSNWHKGWNWTSGFNKCAVGAACQPFHFYFPTPTVLC NEIWTHSYKVSNYSRGSGRCIQMWFDPAQGNPNEEVARFYAAAMSGA GPWAAWPFLLSLALMLLWLLS |

TABLE 5-continued

Useful amino acid and nucleotide sequences for practicing the invention

| SEQ ID | Detailed sequences |
| --- | --- |
| 13 | GCGGCCGCCATGAATTTTGGACTGAGGCTGATTTTCCTGGTGCTGAC<br>CCTGAAAGGCGTCCAGTGTGAAGTCCAATTAGTCGAGAGTGGGGGG<br>GGGGTCGTCCAACCCGGCCGTTCATTACGGCTCTCCTGCTCCGCCT<br>CTGGGTTCACCTTCTCGGGGTACGGCCTATCATGGGTCCGTCAAGCT<br>CCTGGCAAAGGCCTGGAATGGGTCGCCATGATTAGTAGCGGGGGA<br>GCTATACCTATTACGCCGACAGTGTGAAGGGGCGATTCGCCATTAGT<br>AGGGACAATGCAAAGAACACGCTGTTTCTGCAAATGGACTCGTTGAG<br>ACCCGAGGACACGGGTGTCTACTTTTGCGCACGTCACGGTGACGAT<br>CCAGCCTGGTTCGCATATTGGGGGCAGGGTACCCCCGTTACGGTCT<br>CGAGCGCTAGCACAAAGGGCCCTAGTGTGTTTCCTCTGGCTCCCTCT<br>TCCAAATCCACTTCTGGTGGCACTGCTGCTCTGGGATGCCTGGTGAA<br>GGATTACTTTCCTGAACCTGTGACTGTCTCATGGAACTCTGGTGCTCT<br>GACTTCTGGTGTCCACACTTTCCCTGCTGTGCTGCAGTCTAGTGGAC<br>TGTACTCTCTGTCATCTGTGGTCACTGTGCCCTCTTCATCTCTGGGAA<br>CCCAGACCTACATTTGTAATGTGAACCACAAACCATCCAACACTAAAG<br>TGGACAAAAAAGTGGAACCCAAATCCTGTGACAAAACCCACACCTGC<br>CCACCTTGTCCTGCCCCTGAAGCCGCCGGAGGACCTTCTGTGTTTCT<br>GTTCCCCCCCAAACCAAAGGATACCCTGATGATCTCTAGAACCCCTG<br>AGGTGACATGTGTGGTGGTGGATGTGTCTCATGAGGACCCTGAGGT<br>CAAATTCAACTGGTACGTGGATGGAGTGGAAGTCCACAATGCCAAAA<br>CCAAGCCTAGAGAGGAACAGTACAATTCAACCTACAGAGTGGTCAGT<br>GTGCTGACTGTGCTGCATCAGGATTGGCTGAATGGCAAGGAATACAA<br>GTGTAAAGTCTCAAACAAGGCCCTGCCTGCTCCAATTGAGAAAACAA<br>TCTCAAAGGCCAAGGGACAGCCTAGGGAACCCCAGGTCTACACCCT<br>GCCACCTTCAAGAGACGAACTGACCAAAAACCAGGTGTCCCTGACAT<br>GCCTGGTCAAAGGCTTCTACCCTTCTGACATTGCTGTGGAGTGGGAG<br>TCAAATGGACAGCCTGAGAACAACTACAAAACAACCCCCCCTGTGCT<br>GGATTCTGATGGCTCTTTCTTTCTGTACTCCAAACTGACTGTGGACAA<br>GTCTAGATGGCAGCAGGGGAATGTCTTTTCTTGCTCTGTCATGCATG<br>AGGCTCTGCATAACCACTACACTCAGAAATCCCTGTCTCTGTCTCCC<br>GGGAAATGATAGTAAAAGCTT |
| 14 | GCGGCCGCCATGAATTTTGGACTGAGGCTGATTTTCCTGGTGCTGAC<br>CCTGAAAGGCGTCCAGTGTGACATCCAGCTGACACAGAGCCCAAGTT<br>CCCTGTCTGCATCCGTGGGGGATAGGGTTACAATCACTTGTAGTGTA<br>AGCAGCTCGATCAGCAGCAATAACCTGCACTGGTATCAACAGAAACC<br>GGGTAAGGCACCAAAGCCTTGGATTTACGGCACCAGTAATCTGGCCT<br>CCGGGGTGCCGTCTCGCTTTTCTGGGTCCGGCAGCGGTACTGACTA<br>CACATTTACAATCAGCAGCCTACAGCCTGAGGACATTGCGACCTATTA<br>CTGCCAGCAGTGGTCCAGCTACCCATATATGTATACGTTCGGGCAGG<br>GTACCAAGGTCGAGATCAAGCGTACGGTCGCGGCGCCTTCTGTGTT<br>CATTTTCCCCCCATCTGATGAACAGCTGAAATCTGGCACTGCTTCTGT<br>GGTCTGTCTGCTGAACAACTTCTACCCTAGAGAGGCCAAAGTCCAGT<br>GGAAAGTGGACAATGCTCTGCAGAGTGGGAATTCCCAGGAATCTGTC<br>ACTGAGCAGGACTCTAAGGATAGCACATACTCCCTGTCCTCTACTCT<br>GACACTGAGCAAGGCTGATTACGAGAAACACAAAGTGTACGCCTGTG<br>AAGTCACACATCAGGGGCTGTCTAGTCCTGTGACCAAATCCTTCAATA<br>GGGGAGAGTGCTGATAGTAAAAGCTT |
| 15 | GCGGCCGCCATGAATTTTGGACTGAGGCTGATTTTCCTGGTGCTGAC<br>CCTGAAAGGCGTCCAGTGTGAAGTCCAATTAGTCGAGAGTGGCGGG<br>GGGGTCGTCCAACCCGGCCGTTCATTACGGCTCTCCTGCTCCGCCT<br>CTGGGTTCACCTTCTCGGGGTACGGCCTATCATGGGTCCGTCAAGCT<br>CCTGGCAAAGGCCTGGAATGGGTCGCCATGATTAGTAGGGGGGGGA<br>GCTATACCTATTACGCCGACAGTGTGAAGGGGCGATTCGCCATTAGT<br>AGGGACAATGCAAAGAACACGCTGTTTCTGCAAATGGACTCGTTGAG<br>ACCCGAGGACACGGGTGTCTACTTTTGCGCACGTCACGGTGACGAT<br>CCAGCCTGGTTCGCATATTGGGGGCAGGGTACCCCCGTTACGGTCT<br>CGAGCGCTAGCACAAAGGGCCCTAGTGTGTTTCCTCTGGCTCCCTCT<br>TCCAAATCCACTTCTGGTGGCACTGCTGCTCTGGGATGCCTGGTGAA<br>GGATTACTTTCCTGAACCTGTGACTGTCTCATGGAACTCTGGTGCTCT<br>GACTTCTGGTGTCCACACTTTCCCTGCTGTGCTGCAGTCTAGTGGAC<br>TGTACTCTCTGTCATCTGTGGTCACTGTGCCCTCTTCATCTCTGGGAA<br>CCCAGACCTACATTTGTAATGTGAACCACAAACCATCCAACACTAAAG<br>TGGACAAAAAAGTGGAACCCAAATCCTGTGACAAAACCCACACCTGC<br>CCACCTTGTCCTGCCCCTGAACTGCTGGGAGGACCTTCTGTGTTTCT<br>GTTCCCCCCCAAACCAAAGGATACCCTGATGATCTCTAGAACCCCTG<br>AGGTGACATGTGTGGTGGTGGATGTGTCTCATGAGGACCCTGAGGT<br>CAAATTCAACTGGTACGTGGATGGAGTGGAAGTCCACAATGCCAAAA<br>CCAAGCCTAGAGAGGAACAGTACAATTCAACCTACAGAGTGGTCAGT<br>GTGCTGACTGTGCTGCATCAGGATTGGCTGAATGGCAAGGAATACAA<br>GTGTAAAGTCTCAAACAAGGCCCTGCCTGCTCCAATTGAGAAAACAA<br>TCTCAAAGGCCAAGGGACAGCCTAGGGAACCCCAGGTCTACACCCT<br>GCCACCTTCAAGAGACGAACTGACCAAAAACCAGGTGTCCCTGACAT<br>GCCTGGTCAAAGGCTTCTACCCTTCTGACATTGCTGTGGAGTGGGAG |

TABLE 5-continued

Useful amino acid and nucleotide sequences for practicing the invention

| SEQ ID | Detailed sequences |
|---|---|
| | TCAAATGGACAGCCTGAGAACAACTACAAAACAACCCCCCCTGTGCT<br>GGATTCTGATGGCTCTTTCTTTCTGTACTCCAAACTGACTGTGGACAA<br>GTCTAGATGGCAGCAGGGGAATGTCTTTTCTTGCTCTGTCATGCATG<br>AGGCTCTGCATAACCACTACACTCAGAAATCCCTGTCTCTGTCTCCC<br>GGGAAATGATAGTAAAAGCTT |
| 16 | QVQLVQSGAEVVKPGASVKISCKASGYTFTGYFMNWVKQSPGQSLEWI<br>GRIHPYDGDTFYNQKFQGKATLTVDKSSNTAHMELLSLTSEDFAVYYCT<br>RYDGSRAMDYWGQGTTVTVSSASTKGPSVFPLAPSSKSTSGGTAALGC<br>LVKDYFPEPVTVSWNSGALTSGVHTFPAVLQSSGLYSLSSVVTVPSSSL<br>GTQTYICNVNHKPSNTKVDKKVEPKSCDKTHTCPPCPAPELLGGPSVFL<br>FPPKPKDTLMISRTPEVTCVVVDVSHEDPEVKFNWYVDGVEVHNAKTKP<br>REEQYNSTYRVVSVLTVLHQDWLNGKEYKCKVSNKALPAPIEKTISKAK<br>GQPREPQVYTLPPSRDELTKNQVSLTCLVKGFYPSDIAVEWESNGQPE<br>NNYKTTPPVLDSDGSFFLYSKLTVDKSRWQQGNVFSCSVMHEALHNHY<br>TQKSLSLSPG |
| 17 | DIVLTQSPLSLAVSLGQPAIISCKASQSVSFAGTSLMHWYHQKPGQQPRL<br>LIYRASNLEAGVPDRFSGSGSKTDFTLTISPVEAEDAATYYCQQSREYPY<br>TFGGGTKLEIKRTVAAPSVFIFPPSDEQLKSGTASVVCLLNNFYPREAKV<br>QWKVDNALQSGNSQESVTEQDSKDSTYSLSSTLTLSKADYEKHKVYAC<br>EVTHQGLSSPVTKSFNRGEC |

In one embodiment, Ab is an isolated recombinant antibody which has:

(i) a heavy chain variable region comprising HCDR1 of SEQ ID NO: 1, HCDR2 of SEQ ID NO: 2, HCDR3 of SEQ ID NO: 3; and, (ii) a light chain variable region comprising LCDR1 of SEQ ID NO: 4; LCDR2 of SEQ ID NOs: 5 or 8; and LCDR3 of SEQ ID NOs: 6;

wherein said antibody specifically binds to the folate receptor alpha of SEQ ID NO:12.

In specific embodiments, Ab is a recombinant antibody which comprises either:

(a) a variable heavy chain polypeptide comprising HCDR1 of SEQ ID NO:1, HCDR2 of SEQ ID NO:2, HCDR3 of SEQ ID NO:3 and a variable light chain polypeptide comprising LCDR1 of SEQ ID NO:4, LCDR2 of SEQ ID NO:5 and LCDR3 of SEQ ID NO:6; or;

(b) a variable heavy chain polypeptide comprising VH of SEQ ID NO:7 and a variable light chain polypeptide VL of SEQ ID NO:8.

In specific embodiments, Ab is a recombinant antibody which comprises or essentially consists of a heavy chain of SEQ ID NO:9 and a light chain of SEQ ID NO:10.

In specific embodiments, Ab is a recombinant antibody which comprises or essentially consists of a heavy chain of SEQ ID NO:11 and a light chain of SEQ ID NO:10.

In specific embodiments, Ab is a recombinant antibody which comprises or essentially consists of a heavy chain of SEQ ID NO:16 and a light chain of SEQ ID NO:17.

In a specific embodiment, Ab is an anti-FRα antibody which has one or more of the following properties:

(i) it binds to the folate receptor α (FRα) with a $K_D$ of 100 nM or less, preferably with a $K_D$ of 50 nM or less, as measured by surface plasmon resonance, such as Biacore® assay;

(ii) it is an internalizing antibody, in particular, it internalizes in FRα expressing tumor cells;

(iii) it allows the conjugation of 4 to 8 payloads per antibody, in particular without stability issues or aggregation.

In certain embodiments that may be combined with the previous embodiments, Ab is an internalizing antibody fragment of the above-defined recombinant antibodies.

"Internalizing" as used herein in reference to an antibody refers to an antibody that is capable of being taken through the cell's lipid bilayer external membrane to an internal compartment (i.e. "internalized") upon specific binding to the cell, preferably into a degradative compartment in the cell.

Antibody fragments include, but are not limited to, Fab, Fab', Fab'-SH, $F(ab')_2$, Fv, UniBody, and scFv fragments, diabodies, single domain or nanobodies and other fragments. The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see, e.g., U.S. Pat. No. 6,248,516 B1). Antibody fragments can be made by various techniques, including but not limited to proteolytic digestion of an intact antibody as well as production by recombinant host cells as described herein.

In certain embodiments, Ab is a humanized antibody. Typically, a non-human antibody is humanized to reduce immunogenicity to humans, while having at least the same affinity (or superior affinity) of the parental non-human antibody. In preferred embodiments, the antibodies of the present disclosure are humanized antibodies. Generally, a humanized antibody comprises one or more variable domains in which, CDRs, (or portions thereof) are derived from a non-human antibody, e.g. a murine anti-FRα internalizing antibody, and framework regions (or portions thereof) are derived from human antibody sequences. A humanized antibody optionally will also comprise at least a portion of a human constant region. In some embodiments, some framework residues in a humanized antibody are substituted with corresponding residues from a non-human antibody (e.g. the anti-FRα murine antibody from which the CDR residues are derived), e.g., to restore or improve antibody specificity or affinity. In some specific embodiments, some CDR residues in a humanized antibody are also substituted, e.g. to restore or improve antibody specificity or affinity. Humanized antibodies and methods of making them are reviewed, e.g. in Almagro and Fransson, Front. Biosci. 13:1619-1633 (2008), and are further described, e.g., in Riechmann et al., Nature 332:323-329 (1988); Queen et al., Proc. Natl Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing specificity determining region (SDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Preferably Ab is a humanized or human silent antibody, preferably a humanized silent IgG1 antibody.

As used herein, the term "silent" antibody refers to an antibody that exhibits no or low ADCC activity as measured in an ADCC activity assay.

In one embodiment, the term "no or low ADCC activity" means that the silent antibody exhibits an ADCC activity that is at least below 10%, for example below 50% of the ADCC activity that is observed with the corresponding antibody with wild type corresponding IgG isotype.

Silenced effector functions can be obtained by mutation in the Fc constant part of the antibodies and have been described in the Art: Strohl 2009 (AA & N297A); Baudino 2008, D265A (Baudino et al., J. Immunol. 181 (2008): 6664-69, Strohl, CO Biotechnology 20 (2009): 685-91) or also reviewed in Saunders 2019 (Front. Immunol., 7 Jun. 2019, doi: 10.3389/fimmu.2019.01296). Examples of silent IgG1 antibodies comprise the so-called LALA mutations comprising L234A and L235A mutations in the IgG1 Fc amino acid sequence, or Ser228Pro paired with Leu235Glu. Pro331Ser may also be used, optionally in combination with Ledu234Glu and Leu235Phe (LALA-PG) to generate silent IgG1 antibody. Another example of a silent IgG1 antibody comprises the N297A mutation, which results in aglycosylated or non-glycosylated antibodies. Examples of silent IgG4 antibodies comprise Ser228Pro.

In specific embodiments, Ab is farletuzumab, or other anti-FRα antibodies as disclosed in WO2005080431 or WO2017151979.

In other specific embodiments, Ab is mirvetuximab or a silent LALA mutant version of mirevutximab.

In preferred embodiments, Ab is a silent LALA mutant version of farletuzumab, or other anti-FRα antibodies as disclosed in WO2005080431 or WO2017151979.

Antibodies with mutant amino acid sequences can be obtained by mutagenesis (e.g. site-directed or PCR-mediated mutagenesis) of the coding nucleic acid molecules, followed by testing of the encoded altered antibody for retained function (i.e. the functions set forth above) using the functional assays described herein.

Antibodies with Conservative Modifications

In certain embodiments, Ab has a heavy chain variable region comprising HCDR1, HCDR2, and HCDR3 sequences and a light chain variable region comprising LCDR1, LCDR2, and LCDR3 sequences, wherein one or all of these CDR sequences have specified amino acid sequences based on mAb1 (silent LALA mutant version of farletuzumab) antibody described herein, or a functional variant of said antibody with similar CDR sequences differing from the CDR sequences of farletuzumab by 1, 2 or 3 amino acid conservative modifications, and wherein the antibody or protein retains the desired functional properties of mAb1 antibody, in particular when used as an ADC.

In certain embodiments, Ab has a heavy chain variable region comprising HCDR1, HCDR2, and HCDR3 sequences and a light chain variable region comprising LCDR1, LCDR2, and LCDR3 sequences, wherein one or more of these CDR sequences have specified amino acid sequences based on mirevtuximab (or silent LALA mutant version of mirvetuximab) antibody described herein or a functional variant of said antibody with similar CDR sequences differing from the CDR sequences of farletuzumab by 1, 2 or 3 amino acid conservative modifications, and wherein the antibody or protein retains the desired functional properties of mAb1 antibody, in particular when used as an ADC.

Desired functional properties of the anti-FRα antibodies includes without limitation:

(i) it binds to the folate receptor α (FRα) as determined by Elisa assay (as described in the Examples) with an EC50 below 5 nM, for example about 0.5 nM.

(ii) it binds to the folate receptor α (FRα) with a $K_D$ of 100 nM or less, preferably with a $K_D$ of 50 nM or less, as measured by surface plasmon resonance, such as Biacore® assay; for example as determined using the SPR Biacore affinity assay described in the Examples, (iii) it is an internalizing antibody, in particular, it internalizes in FRα expressing tumor cells;

(iv) it allows the conjugation of 4 to 8 payloads per antibody, in particular without stability issues or aggregation, wherein the Drug-Antibody-Ratio is determined for example by RPLC-MS as described in the Examples;

(v) an ADC with such variant anti-FRα antibody provides similar or lower in vitro efficacy in FRα negative cell line (such as BT-474 breast cancer cell lines) as the corresponding control ADC with mAb1 as the anti-FRα antibody, for example using an in vitro efficacy assay in FRα negative cell line as used in the Examples; and/or, (vi) an ADC with such variant anti-FRα antibody provides similar or higher in vivo efficacy in tumor-bearing mouse xenograft models as the corresponding control ADC with mAb1 as the anti-FRa antibody, for example using one of the xenograft models as used in the Examples.

As used herein, the term "conservative sequence modifications" is intended to refer to amino acid substitutions in which the amino acid residue is replaced with an amino acid residue having a similar side chain. Families of amino acid residues having similar side chains have been defined in the art. These families include amino acids with basic side chains (e.g. lysine, arginine, histidine), acidic side chains (e.g. aspartic acid, glutamic acid), uncharged polar side chains (e.g. glycine, asparagine, glutamine, serine, threonine, tyrosine, cysteine, tryptophan), nonpolar side chains (e.g. alanine, valine, leucine, isoleucine, proline, phenylalanine, methionine), beta-branched side chains (e.g. threonine, valine, isoleucine) and aromatic side chains (e.g. tyrosine, phenylalanine, tryptophan, histidine). Thus, one or more amino acid residues within the CDR regions of an antibody of the disclosure can be replaced with other amino acid residues from the same side chain family, and the altered antibody can be tested for retained function using the functional assays described herein.

Modifications can be introduced into an antibody of the disclosure by standard techniques known in the art, such as site-directed mutagenesis and PCR-mediated mutagenesis.

In specific embodiments, Ab is an anti-FRα antibodies which comprises the 6 CDRs which are 100% identical to corresponding CDRs of SEQ ID NO:1-6, and the framework amino acid regions which are at least 90%, 91%, 92%, 93%, 94%, 95%, 96%, 97%, 98%, 99% identical to the corresponding framework amino acid regions as specified in SEQ ID NO: 7 and 8 respectively, wherein said anti-FRα antibody has the following properties:

(i) it binds to the folate receptor α (FRα) as determined by Elisa assay (as described in the Examples) with an EC50 below 5 nM, for example about 0.5 nM.
(ii) it binds to the folate receptor α (FRa) with a $K_D$ of 100 nM or less, preferably with a $K_D$ of 50 nM or less, as measured by surface plasmon resonance, such as Biacore® assay;
(iii) it is an internalizing antibody, in particular, it internalizes in FRα expressing tumor cells;
(iv) it allows the conjugation of 4 to 8 payloads per antibody, in particular without stability issues or aggregation, wherein the Drug-Antibody-Ratio is determined for example by RPLC-MS as described in the Examples;
(v) an ADC with such variant anti-FRα antibody provides similar or lower in vitro efficacy in FRa negative cell line (such as BT-474 breast cancer cell lines) as the corresponding control ADC with mAb1 as the anti-FRα antibody, for example using an in vitro efficacy assay in FRα negative cell line as used in the Examples; and/or,
(vi) an ADC with such variant anti-FRα antibody provides similar or higher in vivo efficacy in tumor-bearing mouse xenograft models as the corresponding control ADC with mAb1 as the anti-FRα antibody, for example using one of the xenograft models as used in the Examples.

In specific embodiments, Ab is an anti-FRα antibodies which comprises the 6 CDRs which are 100% identical to corresponding CDRs of mirevtuximab, and the framework amino acid regions which are at least 90%, 91%, 92%, 93%, 94%, 95%, 96%, 97%, 98%, 99% identical to the corresponding framework amino acid regions of mirvetuximab, wherein said anti-FRα antibody has the following properties:

(i) it binds to the folate receptor α (FRα) as determined by Elisa assay (as described in the Examples) with an EC50 below 5 nM, for example about 0.5 nM.
(ii) it binds to the folate receptor α (FRa) with a $K_D$ of 100 nM or less, preferably with a $K_D$ of 50 nM or less, as measured by surface plasmon resonance, such as Biacore® assay;
(iii) it is an internalizing antibody, in particular, it internalizes in FR& expressing tumor cells;
(iv) it allows the conjugation of 4 to 8 payloads per antibody, in particular without stability issues or aggregation, wherein the Drug-Antibody-Ratio is determined for example by RPLC-MS as described in the Examples;
(v) an ADC with such variant anti-FRα antibody provides similar or lower in vitro efficacy in FRα negative cell line (such as BT-474 breast cancer cell lines) as the corresponding control ADC with mAb1 as the anti-FRα antibody, for example using an in vitro efficacy assay in FRα negative cell line as used in the Examples; and/or,
(vi) an ADC with such variant anti-FRα antibody provides similar or higher in vivo efficacy in tumor-bearing mouse xenograft models as the corresponding control ADC with mAb1 as the anti-FRα antibody, for example using one of the xenograft models as used in the Examples.

Framework or Fc Engineering

For use in the ADC of the present disclosure, Ab may also comprise engineered versions of the antibodies disclosed in the previous section, and which include those in which modifications have been made to framework residues within VH and/or VL, e.g. to improve the properties of the antibody. Typically, such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed by the invention.

Another type of framework modification involves mutating one or more residues within the framework region, or even within one or more CDR regions, to remove T cell-epitopes to thereby reduce the potential immunogenicity of the antibody.

In addition or alternative to modifications made within the framework or CDR regions, antibodies may be engineered to include modifications within the Fc region, typically to alter one or more functional properties of the antibody, such as serum half-life, complement fixation, Fc receptor binding, and/or antigen-dependent cellular cytotoxicity.

Furthermore, Ab is an antibody which may be chemically modified (e.g. one or more chemical moieties can be attached to the antibody) or be modified to alter its glycosylation, again to alter one or more functional properties of the antibody. Each of these embodiments is described in further detail below.

As used herein, the term "isotype constant region" or "Fc region" is used interchangeably to define the C-terminal region of an immunoglobulin heavy chain, including native sequence Fc region and variant Fc regions. The human IgG heavy chain Fc region is generally defined as comprising the amino acid residue from position C226 or from P230 to the carboxyl-terminus of the IgG antibody. The numbering of residues in the Fc region is that of the EU index of Kabat. The C-terminal lysine (residue K447) of the Fc region may be removed, for example, during production or purification of the antibody. Accordingly, a composition of antibodies of the disclosure may comprise antibody populations with all K447 residues removed, antibody populations with no K447 residues removed, and antibody populations having a mixture of antibodies with and without the K447 residue.

In one specific embodiment, the hinge region of $CH_1$ is modified such that the number of cysteine residues in the hinge region is altered, e.g. increased or decreased. This approach is described further in U.S. Pat. No. 5,677,425 by Bodmer et al. The number of cysteine residues in the hinge region of $CH_1$ is altered to, for example, facilitate assembly of the light and heavy chains or to increase or decrease the stability of the antibody.

In other embodiments, the Fc region is modified to decrease the ability of the antibody to mediate antibody dependent cellular cytotoxicity (ADCC) and/or to decrease the affinity of the antibody for an Fcγ receptor by modifying one or more amino acids. Such antibodies with decreased effector functions, and in particular decreased ADCC include silent antibodies.

In certain embodiments, the Fc domain of the IgG1 isotype is used. In some specific embodiments, a mutant variant of the IgG1 Fc fragment is used, e.g. a silent IgG1 Fc which reduces or eliminates the ability of the ADC to mediate antibody dependent cellular cytotoxicity (ADCC) and/or to bind to an Fcγ receptor. A preferred example of an IgG1 isotype silent mutant is IgG1 wherein Leucine is replaced by Alanine at amino acid positions 234 and 235 (so-called LALA mutations) as described in J. Virol 2001 December; 75 (24): 12161-8 by Hezareh et al. Another example is an IgG1 isotype silent mutant having the LALA-PG triple mutations, wherein in addition to the LALA mutations, Proline at position 329 is replaced by Glycine.

In certain embodiments, the Fc domain is a silent Fc mutant preventing glycosylation at position 297 of the Fc domain. For example, the Fc domain contains an amino acid substitution of asparagine at position 297. An example of such amino acid substitution is the replacement of N297 by a glycine or an alanine.

In still another embodiment, the glycosylation of an antibody is modified. For example, an aglycoslated antibody can be made (i.e. the antibody lacks glycosylation). Glycosylation can be altered to, for example, increase the affinity of the antibody for the antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Another modification of the antibodies herein that is contemplated by the present disclosure is pegylation or hesylation or related technologies. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivative other proteins, such as mono ($C_1$-$C_{10}$) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the disclosure. See for example, EP 0 154 316 by Nishimura et al. and EP 0 401 384 by Ishikawa et al.

Another modification of the antibodies that is contemplated by the present disclosure is a conjugate or a protein fusion of at least the antigen-binding region of the antibody of the disclosure to serum protein, such as human serum albumin or a fragment thereof to increase half-life of the resulting molecule. Such approach is for example described in Ballance et al. EP 0 322 094.

Production of Antibodies for Use in Making the ADCs of the Disclosure

Antibodies of the disclosure can be obtained using conventional technical known to those of skill in the art. For more information about nucleic acids encoding antibodies of the disclosure as well as generation of transfectomas producing these antibodies, those of skill in the art can also refer to international application number WO2005080431.

For example, to express the antibodies, or antibody fragments thereof, DNAs encoding partial or full-length light and heavy chains can be obtained by standard molecular biology or biochemistry techniques (e.g., DNA chemical synthesis, PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the VH segment is operatively linked to the CH segment(s) within the vector and the VL segment is operatively linked to the CL segment within the vector. Additionally, or alternatively, the recombinant expression vector can encode a signal peptide that facilitates secretion of the antibody chain from a host cell. The antibody chain gene can be cloned into the vector such that the signal peptide is linked in frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors disclosed herein carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. It will be appreciated by those skilled in the art that the design of the expression vector, including the selection of regulatory sequences, may depend on such factors as the choice of the host cell to be transformed, the level of expression of protein desired, etc. Regulatory sequences for mammalian host cell expression include viral elements that direct high levels of protein expression in mammalian cells, such as promoters and/or enhancers derived from cytomegalovirus (CMV), Simian Virus 40 (SV40), adenovirus (e.g., the adenovirus major late promoter (AdMLP)), and polyoma. Alternatively, nonviral regulatory sequences may be used, such as the ubiquitin promoter or P-globin promoter. Still further, regulatory elements composed of sequences from different sources, such as the SRa promoter system, which contains sequences from the SV40 early promoter and the long terminal repeat of human T cell leukemia virus type 1.

In addition to the antibody chain genes and regulatory sequences, the recombinant expression vectors of the present disclosure may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. It is theoretically possible to express the antibodies of the present disclosure in either prokaryotic or eukaryotic host cells. Expression of antibodies in eukaryotic cells, for example mammalian host cells, yeast or filamentous fungi, is discussed because such eukaryotic cells, and in particular mammalian cells, are more likely than prokaryotic cells to assemble and secrete a properly folded and immunologically active antibody.

The nucleotide sequences encoding the heavy and light chains of preferred antibodies for use in making the ADCs of the disclosure have been described in Tables 3 and 4 (see in particular SEQ ID NOs 13-15).

Mammalian host cells for expressing the recombinant antibodies of the disclosure include Chinese Hamster Ovary (CHO cells) including dhfr-CHO cells (described in Urlaub and Chasin, 1980) used with a DHFR selectable marker (as described inKaufman and Sharp, 1982), CHOK1 dhfr+ cell lines, NSO myeloma cells, COS cells and SP2 cells. When recombinant expression vectors encoding antibody genes are introduced into mammalian host cells, the antibodies are produced by culturing the host cells for a period of time sufficient for expression of the antibody in the host cells and, optionally, secretion of the antibody into the culture medium in which the host cells are grown. Antibodies can be recovered and purified for example from the culture medium after their secretion using standard protein purification methods.

Linker L

As used herein, a "linker" or "linker moiety" refers to any chemical moiety that is capable of covalently joining a compound, such as a drug moiety to another moiety such as an antibody moiety.

The ADCs of the disclosure contain a cleavable linker moiety L bonded to Ab, said anti-FRα antibody as disclosed in the previous section, on one side, and bonded to the drug D on the other side.

In specific embodiments, the linker L is covalently bonded to one or more thiol residues of the antibody Ab, for example from natural or artificial cysteine residues of the antibody sequences.

As used herein, the wording "cleavable" refers to a linker which can be cleaved under specific environmental conditions (such as redox potential or pH) or specific lysosomal enzymes in response to intracellular environments, for example, after internalizing of the ADC in a cell.

In specific embodiments, L is a cleavable linker moiety of formula -A-W—, wherein A is an optional stretcher unit linked to Ab, and W is the cleavable moiety linked to D.

In specific embodiments, the optional stretcher unit A may be selected from the group consisting of one or more amino acid(s), one or more N-substituted amino acid, optionally substituted polyether, $C_1$-$C_{12}$ alkylene, arylene having 6 to 10 ring atoms, $C_3$-$C_8$ cycloalkylene, heterocycloalkylene having 5 to 10 ring atoms, heteroarylene having 5 to 10 ring atoms, $C_2$-$C_{10}$ alkenylene, and any combination thereof, said alkylene and alkenylene being optionally interrupted by one or more heteroatom or chemical groups selected from —O—, —S—, —C(O)—, —NR"—, —C(O)NR"—, —NR"—C(O)—, —NR"—C(O)—NR"—, —NR"—C(O)—O—, —O—C(O)NR"— and triazole, and said alkylene, arylene, cycloalkylene, heterocycloalkylene, heteroarylene, and alkenylene being optionally substituted with one or more of the substituents selected from: halogen, oxo, —OH, —$NO_2$, —CN, $C_1$-$C_6$ alkyl, $C_3$-$C_6$ cycloalkyl, heterocyclyl having 5 to 10 ring atoms, aryl having 6 to 10 ring atoms, heteroaryl having 5 to 10 ring atoms, $C_1$-$C_6$ alkoxy, $C_1$-$C_6$ haloalkyl, $C_1$-$C_6$ haloalkoxy, —(CO)—R', —O—(CO)—R', —(CO)—O—R', —(CO)—NR"R", —NR"—(CO)—R', and —NR"R";

R', R" and R" being independently selected from H and $C_1$-$C_6$ alkyl.

Example of cleavable linkers which may be used for the ADC of the disclosure includes acid-sensitive or acid-labile linkers, such as acid-labile hydrazone linker, lysosomal protease-sensitive linkers, b-glucuronide linker or glutathione-sensitive disulfide linker.

In specific embodiments wherein L is a lysosomal protease-sensitive linker, W comprises a cleavable peptide moiety which may be selected from the group consisting of valine-citruline (Val-Cit), alanine-alanine-asparagine (Ala-Ala-Asn), valine-alanine (Val-Ala) and phenylalanine-lysine (Phe-Lys). Preferably, W comprises a Valine-Alanine peptide moiety.

In other specific embodiments, wherein L is a protease sensitive linker, W comprises a sugar cleavable unit, preferably selected from β-glucuronide or β-galactoside moiety.

In other specific embodiments, wherein L is a glutathione sensitive linker, W comprises a disulfide moiety.

In preferred embodiments, L is a cleavable linker moiety of formula -A-W—, wherein W is of the following formula (III)

(III)

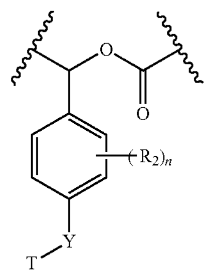

wherein each $R_2$ is independently selected from the group consisting electron-withdrawing groups and $C_1$-$C_4$ alkyl;

n is 0, 1 or 2;

T is a sugar cleavable unit or a polypeptide cleavable unit;

Y is O when T is a sugar cleavable unit, or NR3 when T is a polypeptide cleavable unit; and $R_3$ is selected from the group consisting of H, $C_1$-$C_{24}$ alkyl, $C_2$-$C_6$ alkenyl; optionally substituted polyether, aryl having 6 to 10 ring atoms, $C_3$-$C_8$ cycloalkyl, heterocycloalkyl having 3 to 10 ring atoms, heteroaryl having 5 to 10 ring atoms, and any combination thereof, said alkyl and alkenyl being optionally interrupted by one or more heteroatom or chemical groups selected from —O—, —S—, —C(O)—, —NR"—, —C(O)NR"—, —NR"—C(O)—, —NR"—C(O)—NR'"—, —NR"—C(O)—O—, —O—C(O)NR"— and triazole, R" and R'" being independently selected from H and $C_1$-$C_6$ alkyl, and pharmaceutically acceptable salts thereof.

In specific embodiments, T is a sugar cleavable unit which is a glucuronide or a galactoside.

In other specific embodiments, T is a dipeptide, preferably selected from Val-Cit, Val-Ala and Phe-Lys.

In a more specific embodiment, L corresponds to a linker -A-W— of formula (IV)

(IV)

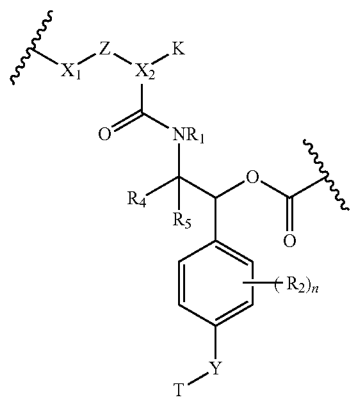

wherein $X_1$ is a connector unit;

Z is an optional spacer;

$X_2$ is a connector unit;

K is an optional hydrophobicity masking entity, preferably selected from polysarcosine and polyethylene glycol;

$R_1$ is selected from the group consisting of H, $C_1$-$C_{24}$ alkyl, $C_2$-$C_6$ alkenyl; optionally substituted polyether, aryl having 6 to 10 ring atoms, $C_3$-$C_8$ cycloalkyl, heterocycloalkyl having 3 to 10 ring atoms, heteroaryl having 5 to 10 ring atoms, and any combination thereof, said alkyl and alkenyl being optionally interrupted by one or more heteroatom or chemical groups selected from —O—, —S—, —C(O)—, —NR"—, —C(O)NR"—, —NR"—C(O)—, —NR"—C(O)—NR"—, —NR"—C(O)—O—, —O—C(O)NR"— and triazole;

$R_4$ is selected from the group consisting H, $C_1$-$C_6$ alkyl and $C_2$-$C_6$ alkenyl, said alkyl and alkenyl being optionally interrupted by one or more heteroatom or chemical groups selected from —O—, —S—, —C(O)—, and —NR"—;

$R_5$ is selected from the group consisting H, $C_1$-$C_6$ alkyl and $C_2$-$C_6$ alkenyl, said alkyl and alkenyl being optionally interrupted by one or more heteroatom or chemical groups selected from —O—, —S—, —C(O)—, and —NR"—.

In a preferred embodiment of the linker of Formula (IV), $X_1$ and $X_2$ are independently selected from the group consisting of one or more amino acid(s), one or more N-substituted amino acid, optionally substituted polyether, $C_1$-$C_{12}$ alkylene, arylene having 6 to 10 ring atoms, $C_3$-$C_8$ cycloalkylene, heterocycloalkylene having 5 to 10 ring atoms, heteroarylene having 5 to 10 ring atoms, $C_2$-$C_{10}$ alkenylene, and any combination thereof, said alkylene and alkenylene being optionally interrupted by one or more heteroatom or chemical groups selected from —O—, —S—, —C(O)—, —NR"—, —C(O)NR"—, —NR"—C(O)—, —NR"—C(O)—NR'"—, —NR"—C(O)—O—, —O—C(O)NR"— and triazole, and said alkylene, arylene, cycloalkylene, heterocycloalkylene, heteroarylene, and alkenylene being optionally substituted with one or more of the substituents selected from: halogen, oxo, —OH, —$NO_2$, —CN, $C_1$-$C_6$ alkyl, $C_3$-$C_6$ cycloalkyl, heterocyclyl having 5 to 10 ring atoms, aryl having 6 to 10 ring atoms, heteroaryl having 5 to 10 ring atoms, $C_1$-$C_6$ alkoxy, $C_1$-$C_6$ haloalkyl, $C_1$-$C_6$ haloalkoxy, —(CO)—R', —O—(CO)—R', —(CO)—O—R', —(CO)—NR"R", —NR"—(CO)—R', and —NR"R";

R', R" and R" being independently selected from H and $C_1$-$C_6$ alkyl.

In other preferred embodiments of the linker of Formula (IV), Z is independently selected from the group consisting of one or more amino acid(s), one or more N-substituted amino acid, optionally substituted polyether, $C_1$-$C_{12}$ alkylene, arylene having 6 to 10 ring atoms, $C_3$-$C_8$ cycloalkylene, heterocycloalkylene having 5 to 10 ring atoms, heteroarylene having 5 to 10 ring atoms, $C_2$-$C_{10}$ alkenylene, and any combination thereof, said alkylene and alkenylene being optionally interrupted by one or more heteroatom or chemical groups selected from —O—, —S—, —C(O)—, —NR"—, —C(O)NR"—, —NR"—C(O)—, —NR"—C(O)—NR"—, —NR"—C(O)—O—, —O—C(O)NR"— and triazole, and said alkylene, arylene, cycloalkylene, heterocycloalkylene, heteroarylene, and alkenylene being optionally substituted with one or more of the substituents selected from: halogen, oxo, —OH, —$NO_2$, —CN, $C_1$-$C_6$ alkyl, $C_3$-$C_6$ cycloalkyl, heterocyclyl having 5 to 10 ring atoms, aryl having 6 to 10 ring atoms, heteroaryl having 5 to 10 ring atoms, $C_1$-$C_6$ alkoxy, $C_1$-$C_6$ haloalkyl, $C_1$-$C_6$ haloalkoxy, —(CO)—R', —O—

(CO)—R', —(CO)—O—R', —(CO)—NR"R", —NR"—(CO)—R', and —NR"R";

R', R" and R" being independently selected from H and $C_1$-$C_6$ alkyl.

In other embodiments of the linker L of formula (IV) or (V), K is a polysarcosine, preferably of the following formula (V)

(V)

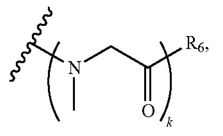

wherein k is an integer between 2 and 50, preferably between 4 and 30, and $R_6$ corresponds to OH or $NH_2$.

In other embodiments of the linker L of formula (IV) or (V), K is a polyethylene glycol moiety (PEG), preferably comprising between 2 and 50 ethylene-glycol moieties.

In a preferred embodiment, L corresponds to the linker of formula (VI):

(VI)

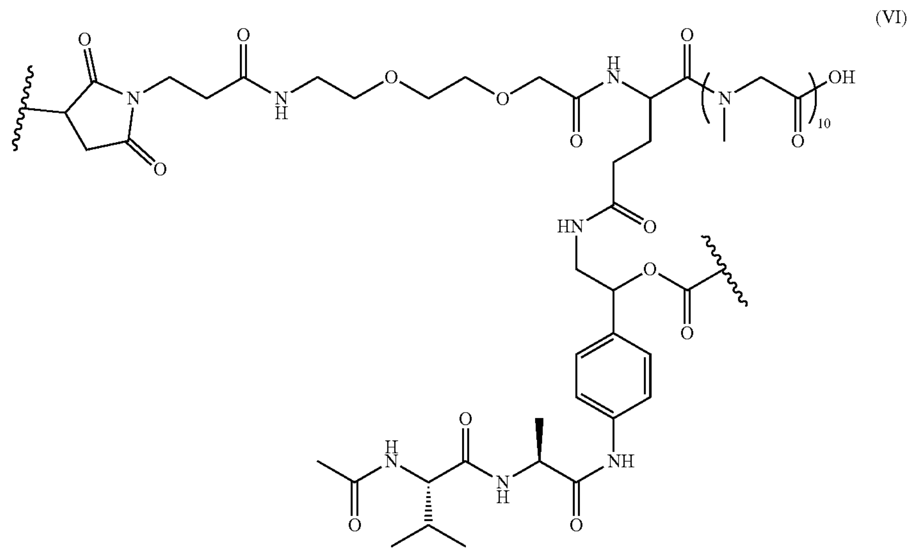

Preferably, said linker L is covalently bonded to one or more thiol residues of the antibody Ab, for example to the eight thiol residues of the antibody Ab.

Payloads

In one embodiment, D of the disclosure is a payload which is linked to X on the side of the carbonyl function of X. In an embodiment, linkage between X and D occurs between carbonyl function of X and amino group of D.

The payload D is an important component of the ADC design. The payload may be a therapeutic agent or a drug. The term "drug" refers in particular to an agent that is capable of modulating a biological process and/or has biological activity.

In specific embodiments, the payload D is a cytotoxic drug which is activated after release from the internalized ADC inside the cytoplasm of tumor cell. It should ideally be able to destroy the tumor cells while not affecting non-tumor cells (when linked to the antibody). The payload should also ideally be of high stability in the systemic circulation and lysosomes. It should preferably have an in vitro subnanomolar IC50 value for cancer cell lines and sufficient solubility in the aqueous environment.

In specific embodiments, the cytotoxic drug is selected from microtubule-disrupting or anti-mitotic agents such as auristatin (including monomethyl auristatin E (MMAE), monomethyl auristatin F (MMAF)), maytansinoids (e.g. maytansine), DNA-damaging agents such as calicheamicin, duocarmycin, and anthracyclines (e.g. daunorubicin, doxorubicin, dihyrdroxyanthracindione), or inhibitors of topoisomerase I such as camptothecines or their analogues.

In specific embodiments, D is selected from the group consisting of: taxon, cytochalasin B, auristatin (including monomethyl auristatin E), gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

In specific embodiments, D is selected from the group consisting of antimetabolites, (e.g., methotrexate, 6-mercaptopurine, 6-thioguanine, cytarabine, 5-fluorouracil decarbazine), ablating agents (e.g., mechlorethamine, thioepa chloraxnbucil, meiphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin)), antibiotics (e.g., dactinomycin (formerly actinomycin), bleomycin, mithramycin, and anthramycin (AMC)), and anti-mitotic agents (e.g., vincristine and vinblastine).

Preferably, D is an inhibitor of topoisomerase I, including without limitation camptothecine analogues, indolocarbazole analogues, phenanthridine analogues, fluoroquinolone analogues, quinoxalines, evodiamines, acridines, naphthyridines, deoxynybomycin analogues, angustine analogues, stilbene thiazole analogues, pyrroloquinazolinoquinoline alkaloids or indenoisoquinoline analogues (see for review: Selas et al., A patent review of topoisomerase I inhibitors (2016-present), 2021, Expert Opinion on Therapeutic Patents, 31 (6), 473-508); preferably selected from the group consisting of camptothecine and their analogues, including without limitation irinotecan, topotecan, camptothecine, SN-38, exatecan, DXd, silatecan, cositecan, lurtotecan, gimatecan, belotecan, rubitecan (see for review: Sriram et al., *Camptothecin and its analogues: a review on their chemotherapeutic potential,* 2005, Natural Product Research, 14 (9), 393-412).

In a preferred embodiment, D is the drug moiety of Exatecan of formula (II) below (II)

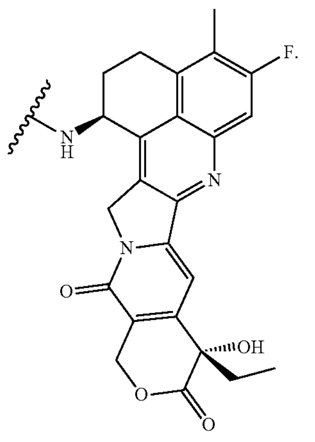

ADC of the Disclosure

In an embodiment, the present disclosure provides ADC where an anti-FRα antibody is linked to a drug (notably Exatecan). Linkers L are as defined above.

Preferably such ADC can selectively deliver an effective dose of the drug, e.g., an inhibitor of topoisomerase I, preferably, Exatecan, to tumor cell expressing FRα.

In an embodiment, the present disclosure provides ADC of formula (I)

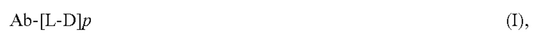

Ab-[L-D]*p* (I), wherein:

Ab is an anti-folate receptor alpha (FRα) antibody which binds specifically to SEQ ID NO:12, p is from 1 to 8, preferably from 6 to 8, and more preferably p is 8.

L is a cleavable linker moiety bonded to said antibody via a thiol residue,

D is a cytotoxic drug moiety bonded to L, e.g. an inhibitor of topoisomerase I,

Ab, L and D have been defined in the previous sections.

The term "p" also referred as the Drug-to-Antibody Ratio or "DAR", corresponds to the number of drug moieties per antibody moiety, or the number of -L-D moieties per antibody Ab in ADCs of Formula (I).

While the Drug-to-Antibody Ratio has in principle an exact value for a single ADC, it is understood that the value will often be an average value when used to describe a composition containing many ADCs, due to some degree of inhomogeneity, typically associated with the conjugation step. The average loading for a sample of an ADC is also referred to herein as the drug to antibody ratio, or "DAR". In some embodiments, the DAR (p) is between about 1 and about 8 (i.e. 1, 1.5, 2, 2.5, 3, 3.5, 4, 4.5, 5, 5.5, 6, 6.5, 7, 7.5 and 8), preferably between about 4 and about 8, more preferably between about 6 and about 8, and even more preferably at about 8.

Hence, in compositions comprising multiple copies of ADCs of Formula (I), "p" refers to the average number of -L-D moieties per antibody Ab. For an average p number close to 8, the ADC will be considered to be a "DAR8".

Methods for measuring the drug-antibody ratio are disclosed in the Examples or for example described in Conilh et al (Pharmaceuticals 2021, 14 (3), 247).

Drug loading to the antibody via the linker L may be limited by the number of attachments sites on the antibody moiety. In some embodiments, the linker moiety (L) of the ADC attaches to the antibody moiety through a chemically active group on one or more amino acid residues on the antibody moiety. For example, the linker may be attached to the antibody moiety via a free amino acid, imino, hydroxyl, thiol or carboxyl group (e.g. to the N- or C-terminus, to the epsilon amino group of one or more lysine residues, to the free carboxylic group of one or more of the glutamic acid or aspartic acid residues, or to the sulfhydryl group of one or more cysteine residues). The site to which the linker is attached can be natural residue in the amino acid sequence of the antibody moiety, or it can be introduced into the antibody moiety, e.g. by DNA recombinant technology (e.g. by introducing a cysteine or a non-natural amino acid residue into the amino acid sequence) or by protein biochemistry (e.g. by reduction, pH adjustment, or hydrolysis).

When the attachment site is inter-chain cysteine thiol group, an antibody may have only one or few cysteine thiol groups through which a linker may be attached. Indeed, most reactive cysteine thiols generally exist as inter-chain disulfide bridges. Over-attachment of linker-toxin to the antibody may destabilize the antibody by reducing the cysteine residues available to form inter-chain disulfide bridge. Therefore, an optimal drug antibody ratio should increase potency of the ADC (by increasing the number of attached drug moieties per antibody) without destabilizing the antibody moiety and without degrading pharmacokinetics properties.

In specific embodiments, -L-D is bonded to the inter-chain reactive thiol residues of the antibody. A typical antibody with full length heavy and light chains comprises 8 available inter-chain reactive thiol residues. Hence, in specific embodiments, the ADC is a DAR8 ADC wherein the eight-L-D moieties are covalently bonded to the 8 inter-chain reactive thiol residues of the antibody Ab, and, most preferably, wherein-L-corresponds to Formula (VI).

In specific embodiments, an ADC of the disclosure corresponds to the following formula (VII)

(VII)

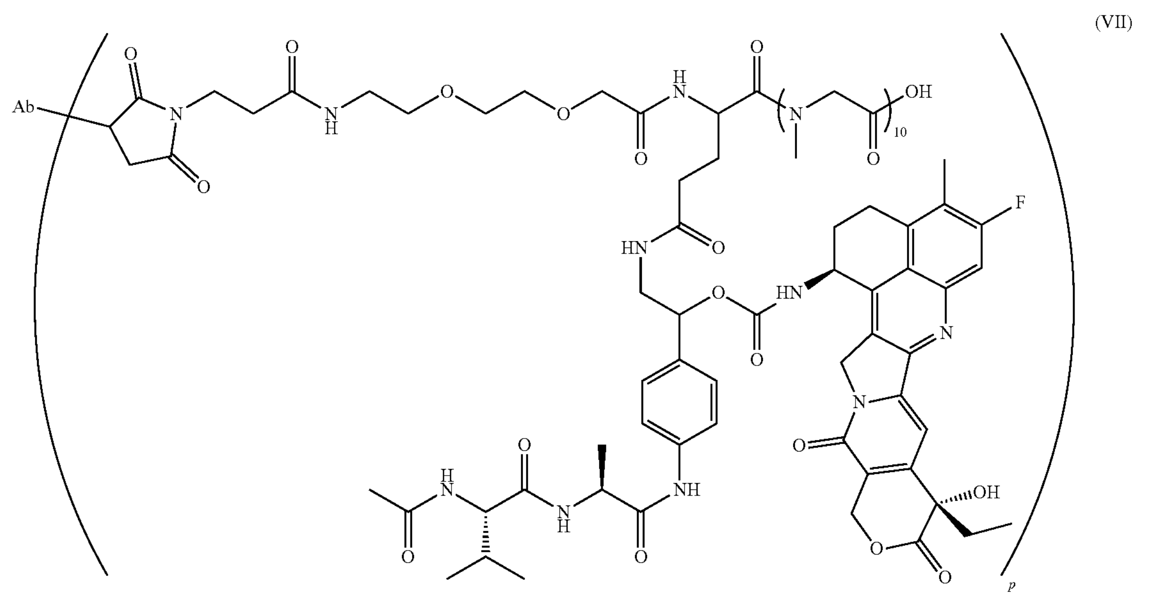

wherein Ab is the anti-FRα as defined in the previous sections and p is from 4 to 8, preferably from 6 to 8.

In a more preferred embodiment, an ADC of the disclosure corresponds to the following formula (VII)

(VII)

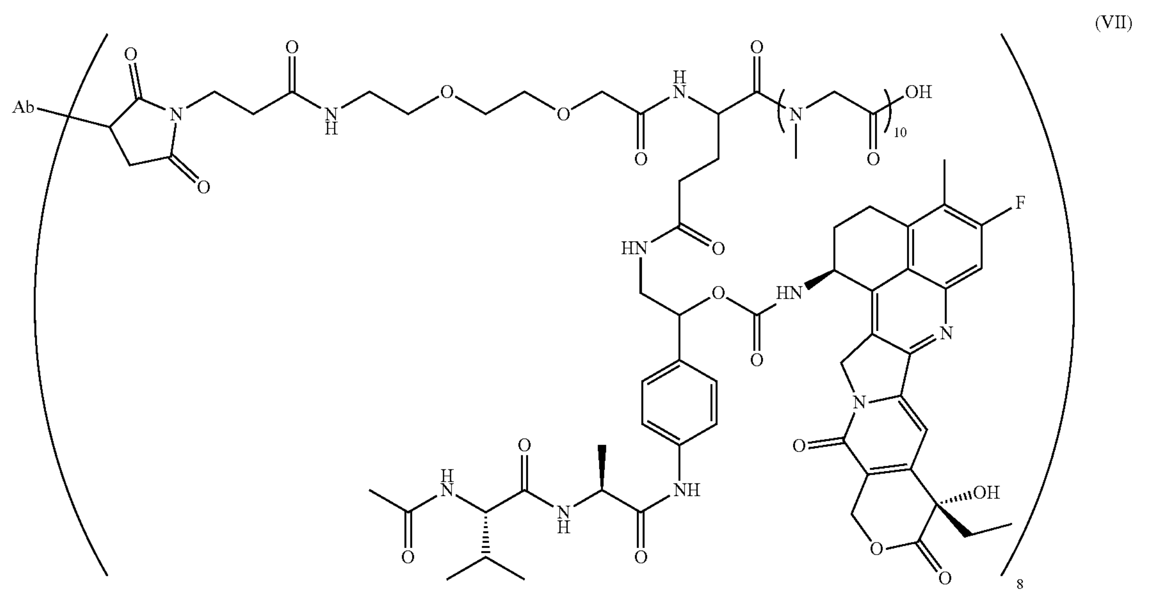

wherein Ab is the anti-FRA as defined in the previous sections.

In a specific embodiment, the ADC of the disclosure corresponds to formula (I) wherein (i) Ab is an anti-folate receptor alpha antibody or an antigen-binding fragment thereof, comprising
   a variable heavy chain polypeptide comprising HCDR1 of SEQ ID NO: 1, HCDR2 of SEQ ID NO:2, HCDR3 of SEQ ID NO:3 and
   a variable light chain polypeptide comprising LCDR1 of SEQ ID NO:4, LCDR2 of SEQ ID NO:5 and LCDR3 of SEQ ID NO:6;
(ii) L is a cleavable linker of formula -A-W—, wherein A is an optional stretcher unit linked to the Ab, and W is a cleavable moiety linked to D
(iii) D is an inhibitor of topoisomerase I, e.g. exatecan;
(iv) p is from 1 to 8, preferably 8.

In a specific embodiment, the ADC of the disclosure corresponds to formula (I) wherein (i) Ab is an antibody comprising a heavy chain of SEQ ID NO:9 and a light chain of SEQ ID NO:10;

(ii) L is a cleavable linker of formula -A-W—, wherein A is an optional stretcher unit linked to the Ab, and W is a cleavable moiety linked to D (iii) D is an inhibitor of topoisomerase I, e.g., exatecan;

(iv) p is from 1 to 8, preferably between 6 and 8, for example about 8.

In a specific embodiment, the ADC of the disclosure is an ADC of formula (I) wherein (i) Ab is an antibody comprising a heavy chain of SEQ ID NO:11 and a light chain of SEQ ID NO:10;

(ii) L is a cleavable linker of formula -A-W—, wherein A is an optional stretcher unit linked to the Ab, and W is a cleavable moiety linked to D (iii) D is an inhibitor of topoisomerase I, e.g., exatecan;

(iv) p is from 1 to 8, preferably between 6 and 8, for example about 8.

In a preferred embodiment, the ADC of the disclosure is an ADC of formula (VII) wherein Ab is an antibody comprising a heavy chain of SEQ ID NO:9 and a light chain of SEQ ID NO: 10.

In another specific embodiment, the ADC of the disclosure is an ADC of formula (VII) wherein Ab is an antibody comprising a heavy chain of SEQ ID NO:11 and a light chain of SEQ ID NO:10.

Pharmaceutical Compositions—Formulations

In another aspect, the present disclosure provides a composition, e.g. a pharmaceutical composition, containing one or a combination of ADC disclosed herein, (for example, mAb1 bounded to a linker L of formula (VI), itself bounded to a drug such as Exatecan), formulated together with a pharmaceutically acceptable carrier.

As used herein, "pharmaceutically acceptable carrier" includes any and all solvents, dispersion media, coatings, antibacterial and antifungal agents, isotonic and absorption delaying agents, and the like that are physiologically compatible. The pharmaceutical formulation of the disclosure may further comprise one or more pharmaceutically acceptable excipients selected from stabilizers, surfactants, buffering agents, antimicrobial preservatives, protectants, antioxidants, chelating agents, bulking agents.

As used herein, a "solvent" is any pharmaceutically acceptable (i.e., safe and non-toxic for administration to a human or another mammal) and useful ingredient for the preparation of a liquid formulation, such as an aqueous formulation. Exemplary solvents include water such as sterile water for injection (WFI) or bacteriostatic water for injection (BWFI), pH buffered solution (e.g., phosphate-buffered saline), sterile saline solution, Ringer's solution or dextrose solution, and combinations thereof. Preferably, the solvent is sterile water for disclosure or bacteriostatic water for injection (BWFI).

As used herein, stabilizers are compounds increasing protein stability, especially against unfolding and aggregation. Preferably, the stabilizer is admitted by the authorities as a suitable additive or excipient in pharmaceutical formulations.

The stabilizer may be a saccharide. A "saccharide" herein comprises the general composition $(CH_2O)_n$ and derivatives s thereof, including monosaccharides, disaccharides, trisaccharides, polysaccharides, sugar alcohols, reducing sugars, nonreducing sugars, etc. Examples of saccharides herein include glucose, sucrose, trehalose, lactose, fructose, maltose, dextran, glycerin, dextran, erythritol, glycerol, arabitol, sylitol, sorbitol, mannitol, mellibiose, melezitose, raffinose, mannotriose, stachyose, maltose, lactulose, maltulose, glucitol, maltitol, lactitol, iso-maltulose, etc.

The concentration of the stabilizer in the pharmaceutical formulation of the disclosure be comprised between 1 and 500 mM.

As used herein, a "surfactant" refers to a surface-active agent. Surfactants are generally added in protein formulations in order to reduce the exposure of hydrophobic regions and so decreasing protein-protein interactions and interface-induced aggregation, also prevented by competition for adsorption sites.

Examples of surfactants herein include polysorbate (for example, polysorbate 20 and, polysorbate 80); poloxamer (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; polyethylglycol, polypropyl glycol, and copolymers of ethylene and propylene glycol (e.g. Pluronics, PF68 etc). Other examples of pharmaceutically acceptable surfactants include polyoxyethylen-sorbitan fatty acid esters (Tween), polyethylene-polypropylene glycols, polyoxyethylene-stearates, polyoxyethylene alkyl ethers, e.g. polyoxyethylene monolauryl ether, alkylphenylpolyoxyethylene ethers (Triton-X), polyoxyethylene-polyoxypropylene copolymer (Poloxamer, Pluronic), and sodium dodecyl sulphate (SDS). Most suitable polyoxyethylenesorbitan-fatty acid esters are polysorbate 20, (sold under the trademark Tween 20™) and polysorbate 80 (sold under the trademark Tween 80™).

Most suitable polyethylene-polypropylene copolymers are those sold under the names Pluronic® F68 or Poloxamer 188™. Most suitable polyoxyethylene alkyl ethers are those sold under the trademark Brij™. Most suitable alkylphenol-polyoxyethylene ethers are sold under the trade name Triton-X.

The concentration of surfactant in the pharmaceutical formulation of the disclosure may be comprised between 0.01 and 0.1% (w/v).

As used herein, the term "buffering agent" refers to an agent which provides that the solution comprising it resists changes in pH by the action of its acid/base conjugate components. Examples of buffering agents that will control the pH in this range include acetate, succinate, gluconate, histidine, citrate, glycylglycine and other organic acid buffers.

A "preservative" is a compound which can be added to the formulations herein to reduce contamination by and/or action of bacteria, fungi, or another infectious agent. The addition of a preservative may, for example, facilitate the production of a multi-use (multiple-dose) formulation. Examples of potential preservatives include octadecyldimethylbenzylammonium chloride, hexamethonium chloride, benzalkonium chloride (a mixture of alkylbenzyldimemylammonium chlorides in which the alkyl groups are long-chained), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and w-cresol.

A "protectant", as generally used herein, is a substance which, when combined with a protein, significantly reduces chemical and/or physical instability of the protein upon lyophilization and/or subsequent refrigerated storage. Exemplary protectants include sugars and their corresponding sugar alcohols, such as sucrose, lactose, trehalose, dextran, erythritol, arabitol, xylitol, sorbitol, and mannitol; amino acids, such as arginine or histidine; lyotropic salts, such as magnesium sulfate; polyols, such as propylene glycol, glycerol, poly(ethylene glycol), or poly(propylene glycol); and combinations thereof. Additional exemplary of protectants include gelatin, dextrins, modified starch, and carboxymethyl cellulose.

The protectant may be added to a pre-lyophilized formulation in a "lyoprotecting amount". This means that, following lyophilization of the protein in the presence of lyoprotecting amount of the protectant, the protein essentially retains its physical and chemical stability and integrity.

An "antioxidant", as generally used herein is a pharmaceutically acceptable excipient generally used to limit oxidation reactions and maintain the stability and safety of proteins. Examples of antioxidants are ascorbic acid, sodium metabisulfite, histamine, methionine, ascorbic acid, glutathione, vitamin E, polyethylenimine.

The antioxidant concentration in the pharmaceutical formulation of the disclosure may be comprised between 5 and 25 mM.

A "chelating agent" is a pharmaceutically acceptable excipient generally used to maintain the stability of proteins. Examples of chelating agent include edetate disodium, diethylenetriamine penta-acetic acid, citric acid, hexaphosphate, thioglycolic acid, zinc.

A "bulking agent," as generally used herein, is a pharmaceutically acceptable excipient generally used to add mass to a lyophilized mixture and contributes to the physical structure of the lyophilized cake (e.g. facilitates the production of an essentially uniform lyophilized cake which maintains an open pore structure). Exemplary bulking agents include mannitol, glycine, lactose, modified starch, polyethylene glycol), and sorbitol.

The form of the pharmaceutical compositions, the route of administration, the dosage and the regimen naturally depend upon the condition to be treated, the severity of the illness, the age, weight, and sex of the patient.

The pharmaceutical compositions of the disclosure can be formulated for a topical, oral, parenteral, intraperitoneal, intranasal, intravenous, intramuscular, subcutaneous or intraocular administration and the like, preferably intraperitoneal or intravenous.

Preferably, the pharmaceutical compositions contain vehicles, which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

To prepare pharmaceutical compositions, an effective amount of the ADC may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders or lyophilisates for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

An ADC of the disclosure can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The ADC of the disclosure may be formulated within a therapeutic mixture to comprise about 0.0001 to 1.0 milligrams, or about 0.001 to 0.1 milligrams, or about 0.1 to 1.0 or even 1.0 to about 10 milligrams per dose. Multiple doses can also be administered.

The pharmaceutical formulation comprising the ADC of the disclosure may be a "Ready-to-Use" injectable formulation or a lyophilized formulation.

In a specific embodiment, the pharmaceutical formulation comprising the ADC of the disclosure may be supplied in a pre-filled syringe.

Uses and Methods of the ADC of the Disclosure

ADC of the present disclosure have therapeutic utilities. For example, these molecules can be administered in a subject, e.g. in vivo, to treat, or prevent a variety of disorders.

It is the contemplated herein to use the ADC of the present disclosure as a medicament, in particular for use in the treatment of cancer in a subject in need thereof, in particular cancer with tumor cells expressing FRα, more specifically, a cancer with a solid tumor, and more specifically selected from the group consisting of ovarian cancer, breast cancer, lung cancer, or mesothelioma.

The terms "cancer" refers to or describe the physiological condition in mammals that is typically characterized by unregulated cell growth. Examples of cancer include, but are not limited to, carcinoma, lymphoma, blastoma (including medulloblastoma and retinoblastoma), sarcoma (including liposarcoma and synovial cell sarcoma), neuroendocrine tumors (including carcinoid tumors, gastrinoma and islet cell cancer), mesothelioma, schwannoma (including acoustic neuroma), meningioma, adenocarcinoma, melanoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophageal cancer, tumors of the biliary tract, as well as head and neck cancer.

The ADC of the disclosure are particularly useful in the treatment of cancer selected from the group consisting of ovarian cancer, triple negative breast cancer, and non-small cell lung cancer.

Hence, the disclosure relates to a method of treating cancer, in particular one of the above listed cancers, and more preferably cancer selected from the group consisting of ovarian cancer, triple negative breast cancer, and non-small cell lung cancer, said method comprising administering a therapeutically efficient amount of an ADC of formula (I) as disclosed herein.

The ADC for use as disclosed above may be administered as the sole active ingredients or in conjunction with, e.g. as an adjuvant to or in combination to, other drugs e.g. anti-viral, anti-inflammatory agents or cytotoxic, anti-proliferative, chemotherapy or anti-tumor agents, e.g. for the treatment or prevention of diseases mentioned above.

For example, the ADC for use as disclosed above may be used in combination with AZT, IFN-alpha, anti-CD20 mAb, anti-CD25 mAb, anti-PD1 mAb, anti-PDL-1 mAb, anti-CTLA4 mAb, chemotherapy agents.

Examples of such anti-PD1 or anti-PDL1 antibody includes without limitation, nivolumab, pembrolizumab, avelumab, durvalumab, cemiplimab, or atezolizumab.

Suitable anti-tumor agents may include without limitation, alkylating agents (such as cyclophosphamide, mechloretamine, chlorambucil, melphalan, nitrosureas, temozolomide), anthracyclines (such as daunorubicin, doxorubicin, epirubicin, idarubicin, mitoxantrone, valrubicin), taxanes (such as paclitaxel, docetaxel), epothilones, inhibitors of Topoisomerase I (such as Irinotecan or Topotecan), inhibitors of Topoisomerase II (such as etoposide, teniposide, or tafluposide), nucleotide analogs and precursor analogs (such as azacitidine, azathioprine, capecitabine, cytarabine, flurouracil, gemcitabine, hydroxyurea, mercaptopurine, methotrexate, or Tioguanine), peptide antibiotics (such as bleomycin, colistin, gramicidin), platinum-based antineoplastic agents (such as carboplatin, cisplatin and oxaliplatin), retinoids (such as tretinoin, alitretinoin, bexarotene), vinca alkaloids and derivatives (such as vinblastine, vincristine, vindesine, vinorelbine), anti-VEGF agents (such as bevacizumab, ranibizumab, sunitinib, sorafenib, pazopanib, targeted therapies such as kinase inhibitors (such as ibrutinib, idelalisib, erlotinib, gefitinib, imatinib, vemurafenib, vismodegib), proteasome inhibitors (such as bortezomib, carfilzomib), histone deacetylase inhibitors (such as vorinostat or romidepsin).

In accordance with the foregoing the present disclosure provides in a yet further aspect a method comprising co-administration, e.g. concomitantly or in sequence, of a therapeutically effective amount of an ADC of the disclosure, and at least one second drug substance, said second drug substance being anti-viral, anti-inflammatory agents or cytotoxic, anti-proliferative, chemotherapy or other anti-tumor agents, e.g. as indicated above.

Also within the scope of the present disclosure are kits consisting of the compositions (e.g. comprising ADC) disclosed herein and instructions for use. The kit can further contain a least one additional reagent, or one or more additional antibodies or proteins (e.g. an antibody having a complementary activity which binds to an epitope on the target antigen distinct from the first antibody). Kits typically include a label indicating the intended use of the contents of the kit. The term label includes any writing, or recorded material supplied on or with the kit, or which otherwise accompanies the kit. The kit may further comprise tools for diagnosing whether a patient belongs to a group that will respond to an ADC treatment, as defined above, in particular having FRα-expressing tumors.

Process of Making ADC of the Disclosure

Antibodies of the disclosure can be conjugated to at least one drug by linkers L by any techniques known in the art. Such techniques are for example described in Greg T. Hermanson, Bioconjugate Techniques, 3rd Edition, 2013, Academic Press (eBook ISBN: 9780123822406). For more information relative to methods for conjugating therapeutic agents to antibodies, see Lyon et al., "*Chapter six—Conjugation of Anticancer Drugs Through Endogenous Monoclonal Antibody Cysteine Residues*", 2012, Methods in Enzymology, 502, 123-138 (doi: 10.1016/B978-0-12-416039-2.00006-9); Chapter 2-7 of "*Antibody-Drug Conjugates: Fundamentals, Drug Development, and Clinical Outcomes*

*to Target Cancer"*, 3 Nov. 2016, eBook ISBN: 9781119060727, doi: 10.1002/9781119060727 and Panowksi S et al. 2014 Jan. 1; 6 (1): 34-45.

In an embodiment, a process for obtaining ADC of Formula (I) comprises the following steps:

culturing a host cell under conditions suitable for expression of a nucleic acid encoding the antibody Ab as defined in the previous sections, isolating the antibody, synthesis of exatecan bonded to the Linker L of formula (VIII):

(VIII)

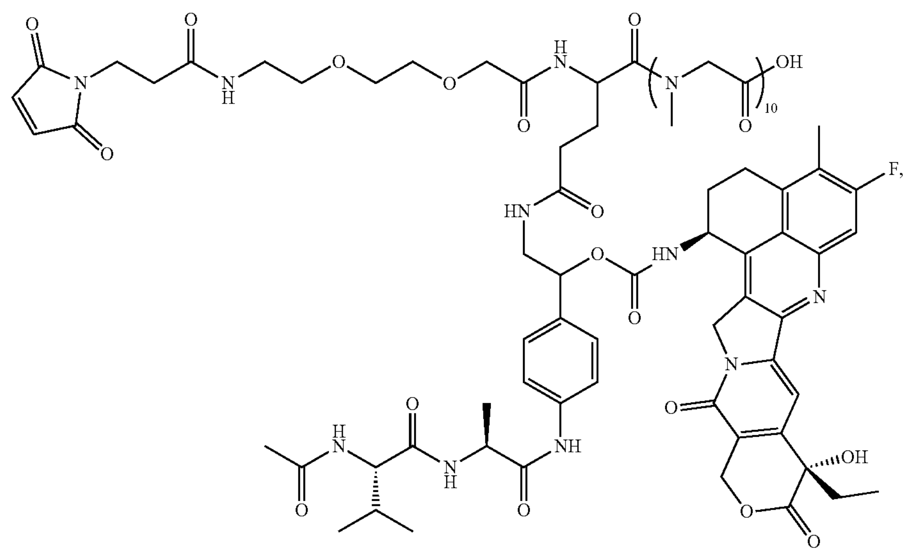

and, conjugating said antibody to the compound of formula (VIII), thereby obtaining an ADC of formula (I).

Antibodies can be obtained as explained above. Antibodies contain four accessible interchain disulfide bonds that can be used as potential conjugation sites. The four interchain disulfide bonds can be reduced, for example by tris(2-carboxyethyl) phosphine (TCEP) or dithiothreitol (DTT), which results in eight thiol groups that are available for conjugation.

The moiety-L-D of formula (VIII) can be prepared following procedures that are known in the art of organic synthesis (chemical reactions, extraction, evaporation, precipitation, chromatography, filtration, trituration, crystallization, and the like), and analytical procedures, which are known to persons of ordinary skill in the art of analytical chemistry. The details of such reactions and techniques can be found in a number of treatises, including Richard Larock, *Comprehensive Organic Transformations, A Guide to Functional Group Preparations,* 2nd Ed (2010), and the multivolume series edited by Michael B. Smith and others, Compendium of Organic Synthetic Methods (1974 et seq.). Starting materials and reagents may be obtained from commercial sources or may be prepared using literature methods.

Exatecan compound can be synthesized following known procedures (see U.S. Pat. No. 5,834,476; WO2019044946 or Sugimori et al., 1998, J. Med. Chem., 41 (13), 2308-2318 doi: 10.1021/jm970765q). Exatecan can also be purchased from reputable sources (for example MedChemExpress cat #HY-13631A or Carbosynth cat #FE72401).

Final ADC of formula (I) is obtained after conjugation of -L-D component to native or engineered cysteine thiol residues of the antibody, following known procedures. See for example Lyon et al., "*Chapter six—Conjugation of Anticancer Drugs Through Endogenous Monoclonal Antibody Cysteine Residues",* 2012, Methods in Enzymology, 502, 123-138 (doi: 10.1016/B978-0-12-416039-2.00006-9) or S J Walsh et al., *Site-selective modification strategies in antibody-drug conjugates*, Chem. Soc. Rev., 2021, 50, 1305-1353, doi: 10.1039/DOCS00310G. Typically, the antibody component is reduced with a reducing agent such as tris(2-carboxyethyl) phosphine (TCEP) or dithiothreitol (DTT); -L-D component is added and is allowed to covalently react with the cysteine thiol residues of the antibody; the final ADC compound is purified and buffer-exchanged.

The invention having been fully described is now further illustrated by the following embodiments and examples, which are illustrative only and are not meant to be further limiting.

SPECIFIC EMBODIMENTS

1. An antibody-drug conjugate of the formula (I):

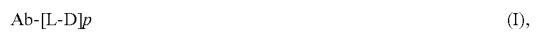

Ab-[L-D]*p* (I), wherein:

Ab is an anti-folate receptor alpha (FRα) antibody which binds specifically to SEQ ID NO:12, L is a cleavable linker moiety bonded to said antibody, preferably via a thiol residue, D is a cytotoxic drug moiety bonded to L, p is from 1 to 8, preferably from 6 to 8, and more preferably p is 8.

2. The antibody-drug conjugate according to embodiment 1, wherein D is an inhibitor of topoisomerase I, preferably selected from the group consisting of camptothecine analogues, and more preferably D is the drug moiety of Exatecan of formula (II) below (II)

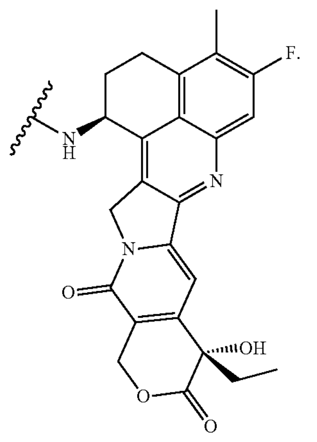

3. The antibody-drug conjugate according to any one of embodiments 1-2, wherein L is a cleavable linker moiety of formula -A-W—, wherein A is an optional stretcher unit linked to Ab, and W is a cleavable moiety linked to D.
4. The antibody-drug conjugate according to embodiment 3, wherein L is a lysosomal protease-sensitive linker, and W comprises a cleavable peptide moiety, for example selected from the group consisting of valine-citrulline (Val-Cit), alanine-alanine-asparagine (Ala-Ala-Asn), valine-alanine (Val-Ala) and phenylalanine-lysine (Phe-Lys).
5. The antibody-drug conjugate according to embodiment 3, wherein L is a protease sensitive cleavable linker and W comprises a sugar cleavable unit, preferably selected from a β-glucuronide or a 3-galactoside moiety.
6. The antibody-drug conjugate according to embodiment 3, wherein L is a glutathione-sensitive linker and W comprises a disulfide moiety.
7. The antibody-drug conjugate according to embodiment 3, wherein W is of the following formula (III)

(III)

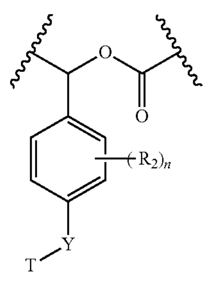

wherein each $R_2$ is independently selected from the group consisting electron-withdrawing groups and $C_1$-$C_4$ alkyl;

n is 0, 1 or 2;

T is a sugar cleavable unit or a polypeptide cleavable unit;

Y is O when T is a sugar cleavable unit, or $NR_3$ when T is a polypeptide cleavable unit; and $R_3$ is selected from the group consisting of H, $C_1$-$C_{24}$ alkyl, $C_2$-$C_6$ alkenyl; optionally substituted polyether, aryl having 6 to 10 ring atoms, $C_3$-$C_8$ cycloalkyl, heterocycloalkyl having 3 to 10 ring atoms, heteroaryl having 5 to 10 ring atoms, and any combination thereof, said alkyl and alkenyl being optionally interrupted by one or more heteroatom or chemical groups selected from —O—, —S—, —C(O)—, —NR"—, —C(O)NR"—, —NR"—C(O)—, —NR"—C(O)—NR"—, —NR"—C(O)—O—, —O—C(O)NR"— and triazole, R" and R" being independently selected from H and $C_1$-$C_6$ alkyl, and pharmaceutically acceptable salts thereof.

8. The antibody-drug conjugate according embodiment 7, wherein L corresponds to a linker -A-W— of formula (IV)

(IV)

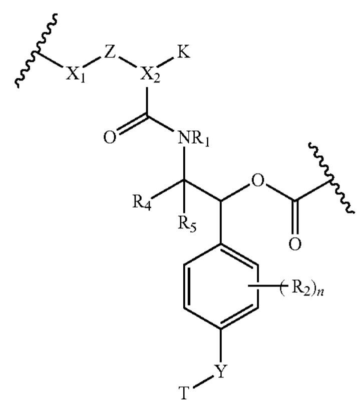

wherein $X_1$ is a connector unit;

Z is an optional spacer;

$X_2$ is a connector unit;

K is an optional hydrophobicity masking entity, preferably selected from polysarcosine and polyethylene glycol;

$R_1$ is selected from the group consisting of H, $C_1$-$C_{24}$ alkyl, $C_2$-$C_6$ alkenyl; optionally substituted polyether, aryl having 6 to 10 ring atoms, $C_3$-$C_8$ cycloalkyl, heterocycloalkyl having 3 to 10 ring atoms, heteroaryl having 5 to 10 ring atoms, and any combination thereof, said alkyl and alkenyl being optionally interrupted by one or more heteroatom or chemical groups selected from —O—, —S—, —C(O)—, —NR"—, —C(O)NR"—, —NR"—C(O)—, —NR"—C(O)—NR'"—, —NR"—C(O)—O—, —O—C(O)NR"— and triazole;

$R_4$ is selected from the group consisting H, $C_1$-$C_6$ alkyl and $C_2$-$C_6$ alkenyl, said alkyl and alkenyl being optionally interrupted by one or more heteroatom or chemical groups selected from —O—, —S—, —C(O)—, and —NR"—; and $R_5$ is selected from the group consisting H, $C_1$-$C_6$ alkyl and $C_2$-$C_6$ alkenyl, said alkyl and alkenyl being optionally interrupted by one or more heteroatom or chemical groups selected from —O—, —S—, —C(O)—, and —NR"—.

9. The antibody-drug conjugate according to embodiment 8, wherein $X_1$ and $X_2$ are independently selected from the group consisting of one or more amino acid(s), one or more N-substituted amino acid, optionally substituted polyether, $C_1$-$C_{12}$ alkylene, arylene having 6 to 10 ring atoms, $C_3$-$C_8$ cycloalkylene, heterocycloalkylene having 5 to 10 ring atoms, heteroarylene having 5 to 10 ring atoms, $C_2$-$C_{10}$ alkenylene, and any combination thereof, said alkylene and alkenylene being optionally interrupted by one or more heteroatom or chemical groups selected from —O—, —S—, —C(O)—, —NR''—, —C(O)NR''—, —NR''—C(O)—, —NR''—C(O)—NR'''—, —NR''—C(O)—O—, —O—C(O)NR''— and triazole, and said alkylene, arylene, cycloalkylene, heterocycloalkylene, heteroarylene, and alkenylene being optionally substituted with one or more of the substituents selected from: halogen, oxo, —OH, —$NO_2$, —CN, $C_1$-$C_6$ alkyl, $C_3$-$C_6$ cycloalkyl, heterocyclyl having 5 to 10 ring atoms, aryl having 6 to 10 ring atoms, heteroaryl having 5 to 10 ring atoms, $C_1$-$C_6$ alkoxy, $C_1$-$C_6$ haloalkyl, $C_1$-$C_6$ haloalkoxy, —(CO)—R', —O—(CO)—R', —(CO)—O—R', —(CO)—NR''R'', —NR''—(CO)—R', and —NR''R'';

R', R'' and R'' being independently selected from H and $C_1$-$C_6$ alkyl.

10. The antibody-drug conjugate according to any one of embodiments 8-9, wherein Z is independently selected from the group consisting of one or more amino acid(s), one or more N-substituted amino acid, optionally substituted polyether, $C_1$-$C_{12}$ alkylene, arylene having 6 to 10 ring atoms, $C_3$-$C_8$ cycloalkylene, heterocycloalkylene having 5 to 10 ring atoms, heteroarylene having 5 to 10 ring atoms, $C_2$-$C_{10}$ alkenylene, and any combination thereof, said alkylene and alkenylene being optionally interrupted by one or more heteroatom or chemical groups selected from —O—, —S—, —C(O)—, —NR''—, —C(O)NR''—NR''—C(O)—, —NR''—C(O)—NR''—, —NR''—C(O)—O—, —O—C(O)NR''— and triazole, and said alkylene, arylene, cycloalkylene, heterocycloalkylene, heteroarylene, and alkenylene being optionally substituted with one or more of the substituents selected from: halogen, oxo, —OH, —$NO_2$, —CN, $C_1$-$C_6$ alkyl, $C_3$-$C_6$ cycloalkyl, heterocyclyl having 5 to 10 ring atoms, aryl having 6 to 10 ring atoms, heteroaryl having 5 to 10 ring atoms, $C_1$-$C_6$ alkoxy, $C_1$-$C_6$ haloalkyl, $C_1$-$C_6$ haloalkoxy, —(CO)—R', —O—(CO)—R', —(CO)—O—R', —(CO)—NR''R'', —NR''—(CO)—R', and —NR''R'';

R', R'' and R'' being independently selected from H and $C_1$-$C_6$ alkyl.

11. The antibody-drug conjugate according to any one of embodiments 8-10, wherein K is a polysarcosine, preferably of the following formula (V)

(V)

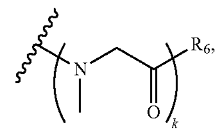

wherein k is an integer between 2 and 50, preferably between 4 and 30, and $R_6$ corresponds to OH or $NH_2$.

12. The antibody-drug conjugate according to any one of embodiments 7-11, wherein T is a sugar cleavable unit which is a glucuronide or a galactoside.

13. The antibody-drug conjugate according to any of embodiments 7-11, wherein T is a dipeptide, preferably selected from Val-Cit, Val-Ala and Phe-Lys.

14. The antibody-drug conjugate according to any one of embodiments 1-3, wherein L is covalently bonded to one or more thiol residues of said antibody, preferably, said L corresponding to a linker of formula (VI):

(VI)

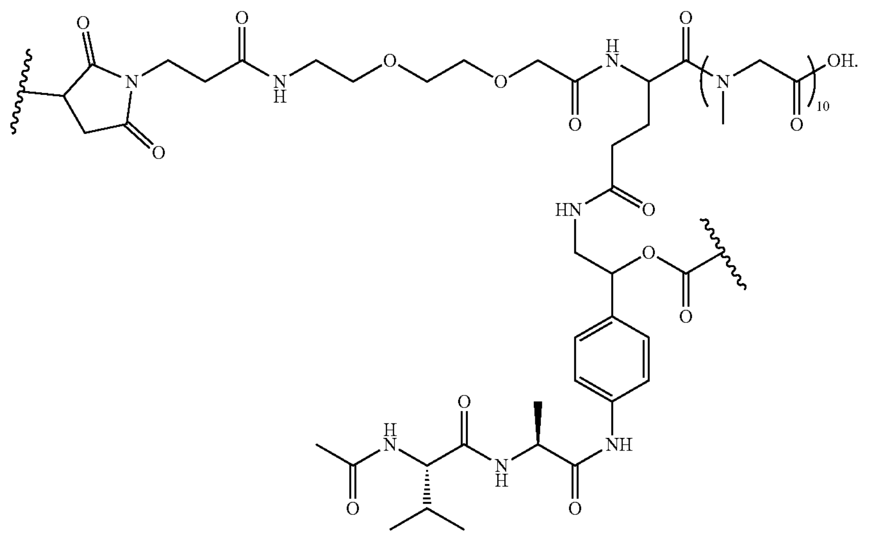

15. The antibody-drug conjugate according to any one of embodiments 1-14, wherein said antibody includes full-length antibodies or antibodies fragments containing antigen binding portions.

16. The antibody-drug conjugate according to any one of embodiments 1-15, which corresponds to the following formula (VII)

(VII)

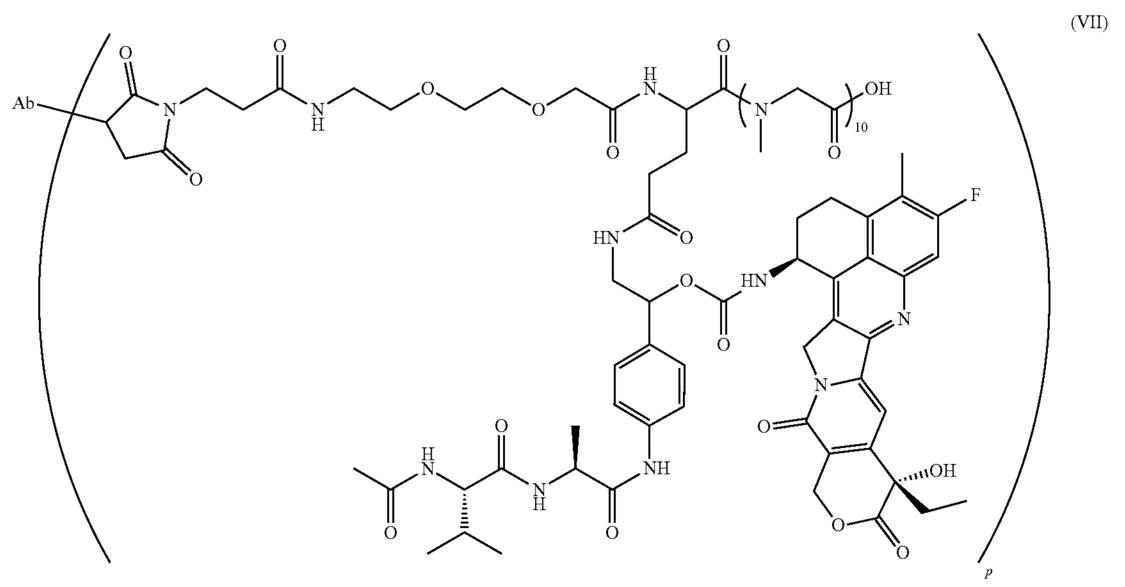

wherein Ab is an anti-FRα antibody, such as farletuzumab, or its silent IgG1 variants, typically comprising alanine substitutions in Leucine 234 and Leucine 235 of IgG1 Fc constant region, and p is from 4 to 8, preferably 8.

17. The antibody-drug conjugate according to any one of embodiments 1-16, wherein:
   Ab is an antibody which comprises a human IgG1 isotype constant region, or a mutant or chemically modified constant region, wherein said mutant or chemically modified constant region confers no or decreased ADCC activity to said antibody when compared to a corresponding antibody with wild type human IgG1 isotype constant region; or,
   Ab is an antibody which comprises a human IgG4 isotype constant region, or a mutant or chemically modified constant region, wherein said mutant or chemically modified constant region confers no or decreased ADCC activity to said antibody when compared to a corresponding antibody with wild type IgG4 isotype constant region.

18. The antibody-drug conjugate according to any one of embodiments 1-17, wherein Ab is an anti-FRα antibody which comprises either:
   (i) a variable heavy chain polypeptide comprising HCDR1 of SEQ ID NO:1, HCDR2 of SEQ ID NO:2, HCDR3 of SEQ ID NO:3 and a variable light chain polypeptide comprising LCDR1 of SEQ ID NO:4, LCDR2 of SEQ ID NO:5 and LCDR3 of SEQ ID NO:6; or
   (ii) a variable heavy chain polypeptide comprising VH of SEQ ID NO:7 and a variable light chain polypeptide comprising VL of SEQ ID NO:8.

19. The antibody-drug conjugate according to any one of embodiments 1-18, wherein Ab comprises or essentially consists of either
   (i) a heavy chain of SEQ ID NO:9 and a light chain of SEQ ID NO:10; or,
   (ii) a heavy chain of SEQ ID NO:11 and a light chain of SEQ ID NO:10.

20. The antibody-drug conjugate according to any one of embodiments 1-19, wherein
   (i) Ab is an anti-folate receptor alpha antibody or an antigen-binding fragment thereof, comprising
      a variable heavy chain polypeptide comprising HCDR1 of SEQ ID NO: 1, HCDR2 of SEQ ID NO:2, HCDR3 of SEQ ID NO:3 and.
      a variable light chain polypeptide comprising LCDR1 of SEQ ID NO:4, LCDR2 of SEQ ID NO:5 and LCDR3 of SEQ ID NO:6;
   (ii) L is a cleavable linker of formula -A-W—, wherein A is an optional stretcher unit linked to the Ab, and W is a cleavable moiety linked to D;
   (iii) D is an inhibitor of topoisomerase I, e.g., exatecan; and,
   (iv) p is from 1 to 8, preferably 8.

21. The antibody-drug conjugate according to embodiments 20, wherein Ab is either
   (i) an antibody or antigen-binding fragment which comprises a heavy chain of SEQ ID NO:9 and a light chain of SEQ ID NO:10, or
   (ii) an antibody or antigen-binding fragment comprises a heavy chain of SEQ ID NO:11 and a light chain of SEQ ID NO:10.

22. The antibody-drug conjugate according to any one of embodiments 1-21, for use as a medicament, preferably for use in the treatment of a tumor in a subject in need thereof, for example a solid tumor, more specifically selected from the group consisting of ovarian cancer, breast cancer, lung cancer, or mesothelioma.

23. The antibody-drug conjugate according to any one of embodiments 1-21, for use in the treatment of a cancer, in a subject in need thereof, selected from the group consisting of ovarian cancer, triple negative breast cancer, and non-small cell lung cancer.

24. A pharmaceutical composition comprising an antibody-drug conjugate according to any one of embodiments 1-21, in combination with one or more pharmaceutical acceptable excipient, diluent or carrier, optionally comprising other active ingredients.

25. A process for obtaining an antibody-drug conjugate according to any one of embodiments 1-23, wherein the method comprises:
 culturing a host cell under conditions suitable for production of an anti-FRα antibody as defined in any one of embodiments 1-21,
 isolating said anti-FRα antibody,
 synthesis of exatecan bonded to the linker L of formula (VIII):

(VIII)

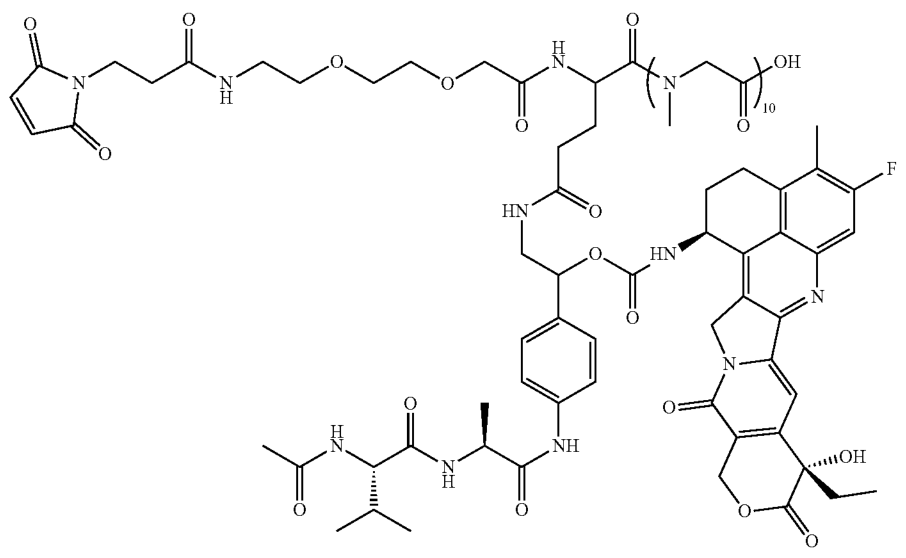

conjugating said anti-FRα antibody to the compound of formula (VIII), thereby obtaining an ADC as defined in any one of embodiments 1-21.

EXAMPLES

Functional Assays

Human FRα-Binding Affinity by ELISA

Sandwich ELISA assays are performed using 96-well high-binding ELISA plates (Corning Inc., New York, NY, USA, Cat #3590). Plates are coated using 100 μL/well of recombinant human FRa protein (Sino Biological cat #11241-H08H) in PBS (pH 7.4) at 2 μg/mL and incubated overnight at 4° C. After 2 washes with PBS-T (PBS+0.05% Tween-20), the plates are blocked with 200 μL/well of incubation buffer (PBS-T+0.1% BSA) for 1 h at room temperature. The plates are washed 4 times with PBS-T, and 100 μL of a threefold dilution series of tested compound (antibody or antibody-drug conjugate) is added. Then, the plates are incubated for 2 h at room temperature in the dark. After 5 washes with PBS-T, plates are incubated 1 h at room temperature with 100 μL/well of a goat anti-human IgG (H+L) HRP conjugated antibody (Jackson Immunoresearch cat #109-035-088), previously diluted 1:250 000 in incubation buffer. After 5 washes with PBS-T, TMB substrate solution (Thermo-Fisher cat #N301) is added. Peroxidase activity is stopped with 0.18M $H_2SO_4$ and absorbance is read at 450 nm (reference wavelength 650 nm) using a Thermo Scientific MultiSkan EX microplate reader. Sigmoidal fittings were performed using GraphPad Prism 9 software.

SPR Biacore Affinity

Surface plasmon resonance (SPR) experiments are performed on a Biacore T200 apparatus, at 25° C. Tested antibody or ADC are captured at low density (300-500 RU) on a CM5 series S sensorchip, beforehand functionalized with a Human Antibody Capture kit (Cytiva cat #BR100839). A functionalized surface/flow cell treated similarly but omitting ligand is used as reference. To measure kinetics rates and affinities, recombinant human FRα (Sino Biological cat #11241-H08H) analyte sample is injected in duplicates at 5 concentrations (0.5, 1, 2, 4, 8 nM) in series using single cycle kinetics strategy and at constant 70 μL/mL flow rate of running buffer (HBS-EP+, Cytiva cat #BR100669) with contact pulses of 300 sec. The dissociation phase is measured by injection of running buffer for 900 sec. Between duplicates, surfaces/flow cells are regenerated with 3M MgCl2 to remove both analyte and ligand, and fresh ligand capture are done using identical conditions. The data analysis is performed using the Biacore Evaluation software after subtraction of reference surface and analyte zero-concentration signals. Data are processed and fit to a 1:1 binding model to determine the binding kinetic rate constants, $k_a$ (on-rate) and $k_d$ (off-rate), and the $K_D$ (equilibrium dissociation constant, also referred to as "affinity"). Mean values and standard deviations over replicates are reported.

Cell-Binding Affinity by Flow Cytometry

Antibody or ADC binding to extracellular human FRα expressed on cancerous cell lines is assessed by flow cytometry. Tested antibody or ADC is conjugated to APC fluorophore using LYNX Rapid APC Antibody Conjugation Kit according to the manufacturer's protocol (Bio-Rad, Cat #LNK032APC). Into 500 000 cells (suspended in 100 μL of PBS in flow cytometry plastic tubes) is added 5 μL of a 10 μg/mL solution of tested APC-labelled antibody or ADC. Cells are incubated 20 min in the dark, are washed with PBS 3 times by centrifugation and are re-suspended in 200 μL of PBS for analysis. Flow cytometry is performed using a BD Fortessa flow cytometer controlled by BD FACSDiva software (BD Biosciences) and data are analyzed using FlowJo software (BD Bioscience).

Stability Assay in Human Plasma

ADC samples (>6 mg/mL solutions in PBS) are diluted with pure sterile Human plasma (GeneTex Cat #GTX73265) in centrifuge tubes with screw cap to yield a final ADC concentration of 200 μg/mL (residual PBS volume below 5% v/v). Samples are incubated at 37° C. and aliquots are taken at time points of 5 min, 6 hours, 1 day, 2 days, 3 days, and 7 days (aliquots were kept frozen at −80° C. until analysis). ADCs are isolated from plasma by immunocapture using Dynabeads™ M-280 Streptavidin (Thermo Scientific) magnetic beads, previously coated with biotinylated human folate receptor alpha recombinant protein (Sino Biologicals cat #11241-H08H). Briefly, 600 μL of commercial bead solution are washed twice with HBS-EP buffer (Cytiva, catalog #BR100188) and re-suspended in 1.2 mL of HBS-EP buffer. 65 μL (48 μg protein amount) of biotinylated recombinant FRα solution is added and solution was agitated for 2 hours at room temperature. Beads are then washed 3 times with HBS-EP buffer and re-suspended in 1.2 mL of HBS-EP buffer. For one immunocapture, 100 μL of previous bead solution is added onto 100 μL of HBS-EP in a microcentrifuge tube. 10 μL of ADC solution in plasma (theoretical 2 μg ADC amount) is added and solution is agitated 2 hours at room temperature. After incubation, the beads-ADC complex is washed twice with HBS-EP buffer, resuspended with 200 μL of HBS-EP buffer and deglycosylated by adding 2 μL/1000 U of PNGase F (New England Biolabs cat #P0705L) overnight at 37° C. with gentle agitation. Beads are then washed twice with HBS-EP buffer, twice with distilled water and once with 10% acetonitrile in water (v/v). The beads are incubated for 30 min with gentle agitation at room temp with 50 μL of a 30% acetonitrile in water (v/v) containing 0.1% (v/v) of formic acid. The eluted samples containing the deglycosylated ADC are then analyzed by denaturing reversed phase chromatography-mass spectrometry using a Thermo UltiMate 3000 UHPLC system equipped with a Bruker Impact II™ Q-TOF mass spectrometer. Mobile phase A is water+0.1% formic acid and mobile phase B is acetonitrile+0.1% formic acid. Column is an Agilent PEEK PLRP-S 1000 Å 2.1×100 mm 5 μm (80° C.). Linear gradient is 20% B to 50% B in 25 min. Flow rate is 0.4 mL/min. UV detection is monitored at 280 nm. The Q-ToF mass spectrometer is used in the m/z range 500-5000 ($ESI^+$). Data are deconvoluted using the MaxEnt algorithm included in the Bruker Compass® software. For stability data analysis, the deconvolution of the raw spectrum within selected light-chain (LC) and heavy-chain (HC) elution time windows is implemented. The drug-linker loss or modifications are identified according to the corresponding mass shifts from the starting ADC material. The relative ratios of ADC with different DAR are calculated by dividing the intensity of the specific ADC sub-species with the intensity from the total ADC species. Final DAR value is calculated as described in Xu et al., Anal. Biochem., 2011, 412 (1), 56-66.

In Vitro Efficacy in FRa Negative Cell Line (BT-474 Cell Line)

To assess unspecific (off-target) cytotoxicity of ADCs, in vitro cytotoxicity assays are realized in BT-474 (FRa negative) cancer cell line. Cells are plated in 96-well plates at an appropriate density depending on the cell line (between 1000 and 10 000 cells/well in 100 μL of appropriate culture media) and incubated at 37° C. for 24 hours. Serial dilutions of the tested compound previously dissolved in culture media (50 μL) are added, and incubation is carried at 37° C. out for 144 hours. MTT (5 mg/mL, 20 μL, Sigma-Aldrich) was added into the wells, and incubation is continued for 1 to 2 hours at 37° C. Culture media is then carefully removed, and well content is homogeneously dissolved with acidified isopropanol. Absorbance values are measured on a Multiskan™ Sky microplate reader (Thermo Scientific) using a wavelength of 570 nm (with a reference wavelength of 690 nm). The IC50 concentration values compared to untreated control cells were determined using inhibition dose response curve fitting (GraphPad Prism 9).

In Vivo Efficacy in Cancer Xenograft Models

Four to five-week-old female CB-17 severe combined immunodeficient (SCID) mice are obtained and quarantined for 7 days prior to study initiation. Mice are inoculated subcutaneously with cells (5-10×106 cells per mouse) resuspended in PBS (OV-90, SW-620, KB, BT-474 cell lines) or 50% BD Matrigel (Corning®) in PBS (PA-1, IGROV-1, OVCAR-3, NCI-H2110 cell lines). When average tumor volume reached about 120-150 mm3 mice are randomized (typically 7 mice per group) and treated by a single (unless stated otherwise) intravenous injection of PBS (negative control) or investigated antibody-drug conjugate. Tumor volumes are measured every 3-5 days using a caliper device (length×width) and calculated using the following formula $V=4/3\times TT\times R_3$, where R represents the radius. Mice are sacrificed when the tumor volume exceeded 1500 mm3 or in case of ulceration of the tumor.

Drug-Antibody-Ratio (DAR) Assessment by Reverse Phase Liquid Chromatography-Mass Spectrometry (RPLC-MS):

Denaturing RPLC-QTOF analysis is used to asses drug-antibody-ratio (DAR) of conjugates. Briefly, ADCs are eluted on an Agilent PLRP-S 1000 Å 2.1×150 mm 8 μm (80° C.) using a mobile phase gradient of water/acetonitrile+0.1% formic acid (0.4 mL/min) and detected using a Bruker Impact II™ Q-TOF mass spectrometer scanning the 500-3500 m/z range ($ESI^+$). Data are deconvoluted using the MaxEnt algorithm included in the Bruker Compass® software.

Example 1: Synthesis of Exatecan-Based Chemical Drug-Linkers

Materials and General Organic Synthesis Methods

All solvents and reagents were obtained from reputable commercial sources (Sigma-Aldrich, Fluorochem, TCI Chemicals, Acros Organics, Alfa Aesar, Enamine, Thermo Fisher, Carbosynth, WuXi AppTec, Iris Biotech) and used without further purification unless stated otherwise. Anhydrous solvents were purchased from Sigma-Aldrich. Fmoc-aminoacids, 2-chlorotrityl, Wang and Rink amide polystyrene 1% DVB 100-200 mesh resins (pre-loaded with first Fmoc-sarcosine aminoacid) were purchased from Christof Senn Laboratories and Sigma-Aldrich. Exatecan Mesylate was purchased from MedChemExpress.

On-resin synthesis was performed in empty SPE plastic tubes equipped with a 20 μm polyethylene frit (Sigma-Aldrich). A Titramax 101 platform shaker (Heidolph) was used for agitation. Unless stated otherwise, all chemical reactions were carried out at room temperature under an inert argon atmosphere.

Liquid nuclear magnetic resonance spectra were recorded on a Bruker Fourier 300HD or Bruker AVANCE III HD400 spectrometer, using residual solvent peak for calibration. Mass spectroscopy analysis has been performed by the Centre Commun de Spectrométrie de Masse (CCSM) of the UMR5246 CNRS institute of the University Claude Bernard Lyon 1.

Normal phase flash chromatography was performed on Teledyne Isco CombiFlash® Rf200 devices using Macherey-Nagel Chromabond® flash cartridges (40-63 μm).

Reverse phase chromatography was performed using Biotage® Sfär C18 Duo 100 Å 30 μm cartridges or Interchim PuriFlash RP-AQ (30 μm) cartridges on Teledyne Isco Combiflash® Rf200 devices; or using an Agilent 1100 preparative binary HPLC system.

Chemical reactions and compound characterization were respectively monitored and analyzed by thin-layer chromatography using pre-coated 40-63 μm silica gel (Macherey-Nagel), HPLC-UV (Agilent 1100 systems) or UHPLC-UV/MS (Thermo UltiMate 3000 UHPLC system equipped with a Bruker Impact II™ Q-TOF mass spectrometer or Agilent 1260 HPLC system equipped with a Bruker MicrOTOF-QII mass spectrometer).

HPLC Method 1: Agilent 1100 HPLC system equipped with DAD detection. Mobile phase A was water+0.1% TFA and mobile phase B was acetonitrile. Column was an Agilent Zorbax SB-Aq 4.6×150 mm 5 μm (room temperature). Linear gradient was 0% B to 50% B in 30 min, followed by a 5 min hold at 50% B. Flow rate was 1.0 mL/min.

HPLC Method 2: Agilent 1100 HPLC system equipped with DAD detection. Mobile phase A was water+0.1% TFA and mobile phase B was acetonitrile. Column was an Agilent Poroshell 120 EC-C18 3.0×50 mm 2.7 μm (room temperature). Linear gradient was 5% B to 80% B in 9 min, followed by a 1 min hold at 80% B. Flow rate was 0.8 mL/min.

HPLC Method 3: Agilent 1100 HPLC system equipped with DAD detection. Mobile phase A was water+0.1% TFA and mobile phase B was acetonitrile. Column was an Agilent Poroshell 120 EC-C18 3.0×50 mm 2.7 μm (room temperature). Linear gradient was 5% B to 80% B in 20 min, followed by a 2 min hold at 80% B. Flow rate was 0.8 mL/min.

HPLC Method 4: Thermo UltiMate 3000 UHPLC system+Bruker Impact II™ Q-ToF mass spectrometer. Mobile phase A was water+0.1% formic acid and mobile phase B was acetonitrile+0.1% formic acid. Column was an Agilent PLRP-S 1000 Å 2.1×150 mm 8 μm (80° C.). Linear gradient was 10% B to 50% B in 25 min. Flow rate was 0.4 mL/min. UV detection was monitored at 280 nm. The Q-ToF mass spectrometer was used in the m/z range 500-3500 ($ESI^+$). Data were deconvoluted using the MaxEnt algorithm included in the Bruker Compass® software.

HPLC Method 5 (preparative method): Teledyne Isco CombiFlash® Rf200 binary MPLC system equipped with DAD detection. Mobile phase A was water+0.1% TFA and mobile phase B was acetonitrile. Reusable cartridges were Biotage® Sfär C18 Duo 100 Å 30 μm (30 g). Linear gradient was 10% B to 50% B in 35 min, followed by a 5 min hold at 50% B. Flow rate was 25 mL/min.

HPLC Method 6 (preparative method): Agilent 1100 preparative binary HPLC system equipped with dual-loop auto-injector, DAD detection and fraction collector. Mobile phase A was water+0.1% TFA and mobile phase B was acetonitrile. Column was a Waters SunFire C18 OBD Prep Column, 100 Å, 5 μm, 19 mm×250 mm (room temperature). Linear gradient was 10% B to 60% B in 40 min, followed by a 5 min hold at 60% B. Flow rate was 25 mL/min.

1.1) Monodisperse Polysarcosines Intermediates

1.1.1) General Methods

On-resin synthesis of monodisperse polysarcosines were realized using sub-monomer synthesis iterative procedures (as described in WO2019081455) for Rink amide and 2-chlorotrityl resin or following classic Fmoc/SPPS methodologies with the commercial Fmoc-Sar-Sar-OH dipeptoid building block (CAS #2313534-20-0) for Wang resin. On-resin dimeric stage (n=2) was avoided due to diketopiperazine formation. All synthesis yields are reported based upon initial Fmoc-sarcosine loading indicated by the manufacturer. Unless stated otherwise, all reactions were carried out at room temperature. Rink amide, 2-chlorotrityl or Wang polystyrene 1% DVB 100-200 mesh resins preloaded with a first Fmoc-sarcosine residue (Christof Senn Laboratories) were used (typical initial loading of 0.6-1 mmol/g). Laboratories) were used (typical initial loading of 0.6-1 mmol/g).

1.1.2) Elongation of Polysarcosines

Fmoc-sarcosine preloaded Rink amide, 2-chlorotrityl or Wang resin was treated with 20% piperidine in DMF (1 mL per 100 mg of resin) for 2 times 15 min at room temperature. The resin was then washed with DMF (4 times) and DCM (4 times). To the resin was added a solution of Fmoc-Sar-Sar-OH (3 eq), HATU (2.9 eq) and DIPEA (6 eq) in DMF (1 mL per 100 mg of resin). The reaction vessel was agitated for 2 hours and the resin was washed with DMF (4 times) and DCM (4 times). The resin was treated with 20% piperidine in DMF (1 mL per 100 mg of resin) for 2 times 15 min at room temperature. The resin was then washed with DMF (4 times) and DCM (4 times).

For synthesis on Rink amide or 2-chlorotrityl resin, classic sub-monomer synthesis procedures were then used, as described in WO2019081455. Elongation of the n=3 polysarcosine oligomer was performed until the desired length was obtained, by alternating bromoacetylation and amine displacement steps. The bromoacetylation step was performed by adding 10 eq of bromoacetic acid and 13 eq of diisopropylcarbodiimide in DMF (2 mL per 100 mg of resin). The mixture was agitated for 30 min, drained and washed with DMF (4 times). For the amine displacement step, a 40% (wt) methylamine in water solution was added (1.5 mL per 100 mg of resin) and the vessel was shaken for 30 min, drained and washed with DMF (4 times) and DCM (4 times).

For synthesis on Wang resin, classic Fmoc/SPPS procedures were used. Elongation of the n=3 polysarcosine oligomer was performed by iterative coupling of Fmoc-Sar-Sar-OH dipeptoid building block (CAS #2313534-20-0). To the resin was added a solution of Fmoc-Sar-Sar-OH (3 eq), HATU (2.9 eq) and DIPEA (6 eq) in DMF (1 mL per 100 mg of resin). The reaction vessel was agitated for 90 min and the resin was extensively washed with DMF (4 times) and DCM (4 times). Resin was then treated with 20% piperidine in DMF (1 mL per 100 mg of resin) for 2 times 15 min at room temperature. The resin was washed with DMF (4 times) and DCM (4 times). This coupling/Fmoc-deprotection cycle was repeated until desired polysarcosine length is obtained. If necessary, the last coupling is made with commercial Fmoc-Sar-OH aminoacid instead of Fmoc-Sar-Sar-OH dipeptoid unit in order to obtain a final polysarcosine of even length.

1.1.3) Final On-Resin Side-Functionalization of Polysarcosines, Optional Capping, Resin Cleavage and Purification When the desired on-resin polysarcosine monodisperse oligomer length is reached, orthogonal chemical functionalization is performed. It is optionally followed by a final capping with a Fmoc-aminoacid (for example Fmoc-Gly-OH, Fmoc-β-Ala-OH, Fmoc-Amino-3,6 dioxaoctanoic acid, Fmoc-9-Amino-4,7-Dioxanonanoic acid). The Fmoc protecting group capping the N-terminus of the final compound can be removed before or after resin cleavage, depending on the orthogonal functionalization chemistry that is used (see after).

1.1.3.1) 2-Azidoethan-1-Amine Side-Functionalized Polysarcosines

To the Rink or 2-chlorotrityl resin is added 10 eq of bromoacetic acid and 13 eq of diisopropylcarbodiimide in DMF (2 mL per 100 mg of resin). The mixture was agitated for 30 min, drained and washed with DMF (4 times). A 3 molar solution of 2-azidoethan-1-amine in DMF was added (1 mL per 100 mg of resin) and the vessel was shaken for 45 min, drained and washed with DMF (4 times) and DCM (4 times). It was followed by a 1-hour Fmoc-Gly-OH coupling (5 eq Fmoc-Gly-OH, 4.9 eq HATU, 10 eq DIPEA in DMF (1 mL per 100 mg of resin) and Fmoc-deprotection with 20% piperidine in DMF (1 mL per 100 mg of resin) for 2 times 15 min at room temperature. The resin was washed with DMF (4 times) and DCM (4 times).

Final polysarcosine compounds were cleaved from the resin (100% TFA 2 times 30 min for Rink and Wang resins, 20% TFA in DCM 2 times 15 min for 2-chlorotrityl resin). Resin was filtered, and volatiles were removed under reduced pressure to afford a crude that was purified on Interchim® RP-AQ (30 μm) cartridges. Mobile phase A was water+0.1% TFA and mobile phase B was acetonitrile.

1.1.3.2) Glutamic Acid Side-Functionalized Polysarcosines

To the Rink, Wang or 2-chlorotrityl resin was added a solution of Fmoc-Glu(OAll)-OH (3 eq), HATU (2.9 eq) and DIPEA (6 eq) in DMF (1 mL per 100 mg of resin). The reaction vessel was agitated for 90 min and the resin was extensively washed with DMF (4 times) and DCM (4 times). Resin was then treated with 20% piperidine in DMF (1 mL per 100 mg of resin) for 2 times 15 min at room temperature. The resin was washed with DMF (4 times) and DCM (4 times). It was followed by a 1-hour coupling with Fmoc-Amino-3,6 dioxaoctanoic acid (3 eq), HATU (2.9 eq), DIPEA (6 eq) in DMF (1 mL per 100 mg of resin). The resin was washed with DMF (4 times), DCM (4 times). Alloc-protecting group was removed by a 2 times 30 min treatment with a DCM solution containing 0.25 eq of $Pd(PPh_3)_4$ and 20 eq of phenylsilane (gently agitated under a stream of argon). The resin was then washed with DMF (5 times) and DCM (5 times). Optionally an N-hydroxysuccinimide (NHS) ester was introduced to the carboxylic acid side chain of the final polysarcosine compound, by a 90 min treatment with a DMF solution containing 50 eq of DIC and 60 eq of N-hydroxysuccinimide (1.5 mL per 100 mg of resin). The resin was then washed with DMF (4 times) and DCM (4 times).

Final polysarcosine compounds were cleaved from the resin (100% TFA 2 times 30 min for Rink and Wang resins, 20% TFA in DCM 2 times 15 min for 2-chlorotrityl resin). Resin was filtered, and volatiles were removed under reduced pressure to afford a crude that was purified on Interchim® RP-AQ (30 μm) cartridges. Mobile phase A was water+0.1% TFA and mobile phase B was acetonitrile.

1.1.4) Final Polysarcosine Intermediates

The following table 6 lists the resulting compounds.

TABLE 6

| Compound name | Structure | Resin | Yield | MS ($ESI^+$) | HPLC retention time |
|---|---|---|---|---|---|
| Compound PSR1 NH2-Gly-(N3)-PSAR10-CONH2 (transparent oil) | 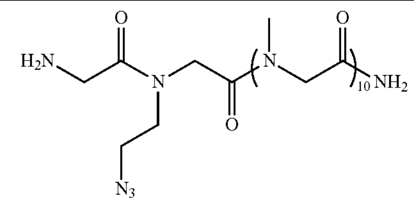 | Rink amide | 48% | Calc $[M + H]^+ = 911.5$ Obs $[M + H]^+ = 911.5$ | 12.5 min |
| Compound PSR2 $NH_2$-Gly($N_3$)-PSAR10-COOH (transparent oil) | 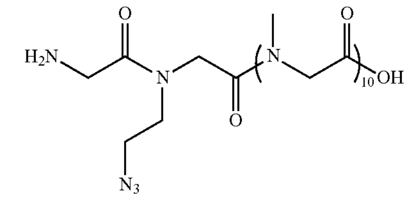 | 2-chlorotrityl | 14% | Calc $[M + H]^+ = 912.5$ Obs $[M + H]^+ = 912.5$ | 14.5 min (HPLC method 1) |
| Compound PSR3 NHFmoc-PEG2-(Glu-NHS)-PSAR10-$CONH_2$ (white solid) | 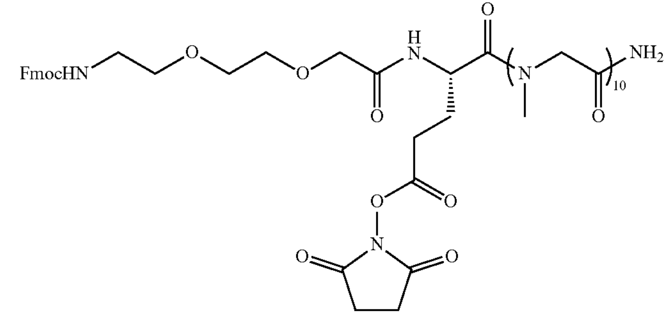 | Rink amide | 49% | Calc $[M + 2H]^{2+} = 661.3$ Obs $[M + 2H]^{2+} = 661.3$ | 5.9 min (HPLC method 2) |

TABLE 6-continued
| Compound name | Structure | Resin | Yield | MS ($ESI^+$) | HPLC retention time |
|---|---|---|---|---|---|
| Compound PSR4 NHFmoc-PEG2-(Glu-NHS)-PSAR10-COOH (white solid) | 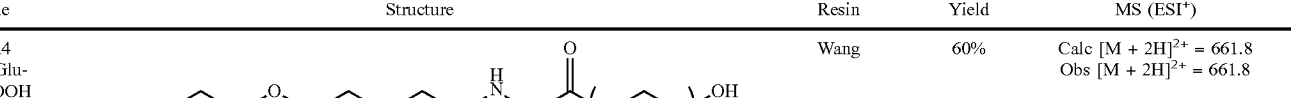 | Wang | 60% | Calc $[M + 2H]^{2+}$ = 661.8<br>Obs $[M + 2H]^{2+}$ = 661.8 | 5.7 min (HPLC method 2) |

1.2) Intermediate Compounds Synthesis

1.2.1) Synthesis of Compound INT1

Compound INT1

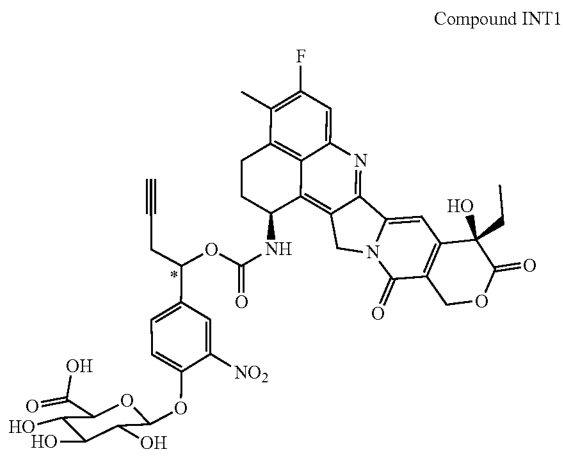 [SMILES: C#CCC(OC(=O)N[C@H]1CCc2c(C)c(F)cc3nc4c(c1c23)Cn1c-4cc2c(c1=O)COC(=O)[C@]2(O)CC)c1ccc(OC2OC(C(=O)O)C(O)C(O)C2O)c([N+](=O)[O-])c1]

Compound INT1 was synthesized following procedures described in patent application WO2019081455. This compound is an equimolar diastereoisomeric mixtures (stereogenic center indicated by an asterisk).

1.2.2) Synthesis of Compound INT2, INT2-S and INT2-R

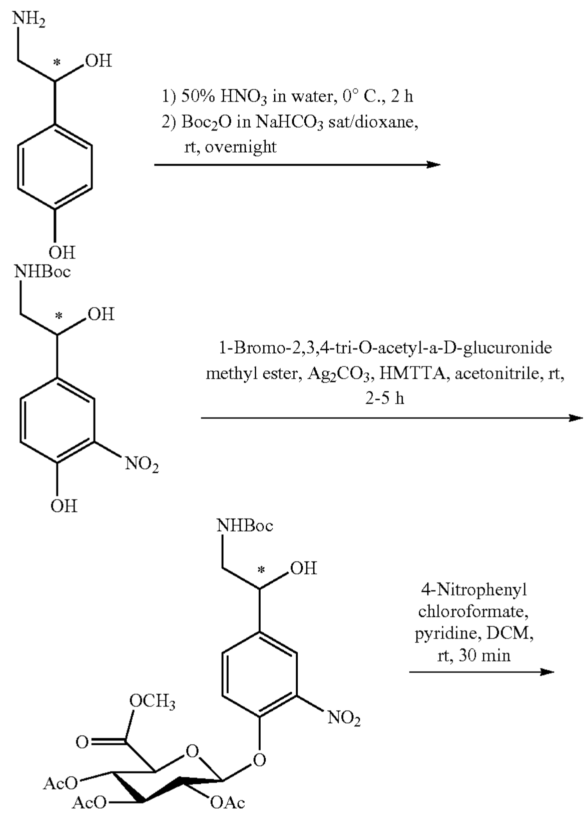

-continued

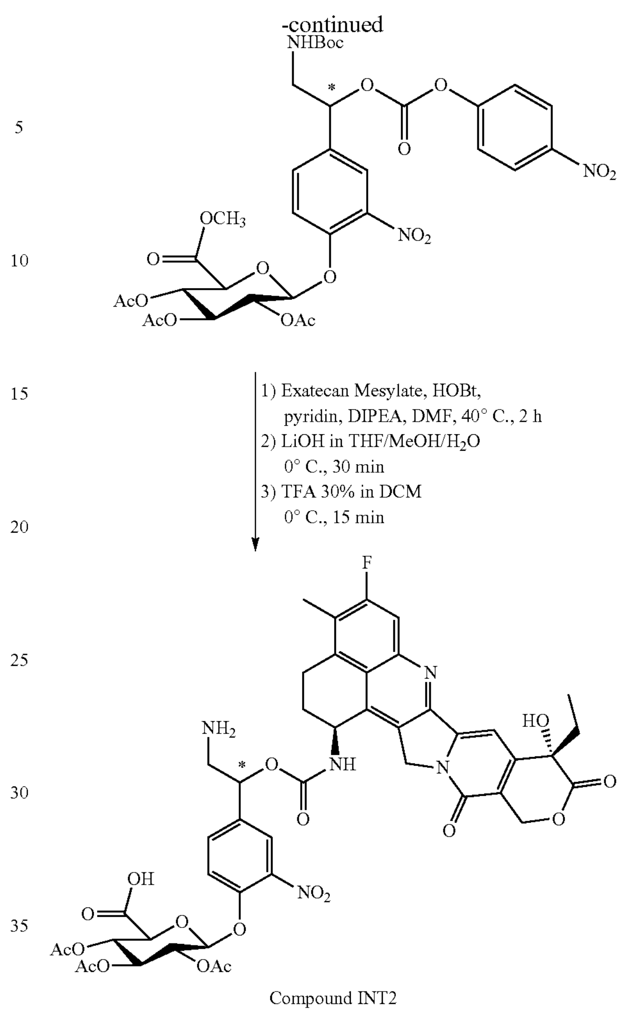

Compound INT2

1.2.2.1) Synthesis of tert-butyl(2-hydroxy-2-(4-hydroxy-3-nitrophenyl)ethyl)carbamate (±)-octopamine hydrochloride (1690 mg/11 mmol) was weighted in a round-bottom flask and suspended in 4 mL of distilled water. The flask was chilled at 0° C. and 4 mL of a pre-chilled 65% nitric acid solution was slowly added. The reaction was kept at 0° C. for 20 minutes, showing complete mono-nitration of the starting material as assessed by HPLC. The content of the flask was transferred in a 250 mL pre-chilled Erlenmeyer and slowly neutralized at 0° C. with a saturated $NaHCO_3$ solution (approx. 50 mL) until a pH value of 8-9 is reached. 30 mL of dioxane was then added, followed by Boc2O (7202 mg/13.2 mmol). The reaction was then allowed to reach room temperature and was stirred overnight. The reaction was then diluted with EtOAc and washed 3 times with a saturated citric acid solution and once with saturated NaCl solution. The organic phase was dried over MgSO4, filtered and evaporated under vacuum to afford a crude that was purified by chromatography on silica gel (petroleum ether/EtOAc, gradient from 70:30 to 20:80) to afford title compound (1320 mg/40%) as a thick yellow-to-brown oil. 1H NMR (300 MHz, DMSO-d6) δ 10.79 (s, 1H), 7.79 (d, J=2.1 Hz, 1H), 7.47 (dd, J=8.6, 2.1 Hz, 1H), 7.08 (d, J=8.6 Hz, 1H), 6.74 (t, J=5.9 Hz, 1H), 4.56 (t, J=6.3 Hz, 1H), 3.07 (td, J=6.1, 1.6 Hz, 2H), 1.31 (s, 9H). MS m/z (ESI+): Calc [M+H]+=299.1; Exp [M+H]+=299.1. HPLC Method 2 retention time=5.5 min.

1.2.2.2) Synthesis of (2S,3R,4S,5S,6S)-2-(4-(2-((tert-butoxycarbonyl)amino)-1-hydroxyethyl)-2-nitrophenoxy)-6-(methoxycarbonyl)tetrahydro-2H-pyran-3,4,5-triyl triacetate In a round-bottom flash, $Ag_2CO_3$ (1500 mg/5.4 mmol) and 1,1,4,7,10,10-hexamethyltriethylenetetramine (251 mg/1.1 mmol) were taken up in 4 mL of anhydrous acetonitrile and stirred during 2 hours at room temperature. Previous compound tert-butyl(2-hydroxy-2-(4-hydroxy-3-nitrophenyl)ethyl)carbamate (292 mg/0.98 mmol) and 1-bromo-2,3,4-tri-O-acetyl-α-D-glucuronide methyl ester (583 mg/1.46 mmol) were added at 0° C. and the solution mixture was stirred for 4 h at room temperature. The reaction was then filtered on celite, diluted with EtOAc, and washed 3 times with a saturated citric acid solution and once with a saturated NaCl solution. The organic phase was dried over $MgSO_4$, filtered and evaporated under vacuum to afford a crude that was purified by chromatography on silica gel (petroleum ether/EtOAc, gradient from 70:30 to 30:70) to afford title compound (244 mg/48%) as a yellow foam. 1H NMR (300 MHZ, DMSO-d6) δ 7.76 (dd, J=3.3, 2.1 Hz, 1H), 7.60 (t, J=7.6 Hz, 1H), 7.36 (dd, J=8.7, 2.6 Hz, 1H), 6.77 (s, 1H), 5.71 (d, J=7.8 Hz, 1H), 5.61 (s, 1H), 5.46 (td, J=9.5, 1.1 Hz, 1H), 5.21-5.02 (m, 3H), 4.75 (dd, J=9.9, 1.4 Hz, 1H), 4.62 (s, 1H), 3.65 (s, 3H), 3.17 (s, 2H), 3.10 (t, J=6.1 Hz, 2H), 2.81-2.59 (m, 6H), 2.05-1.96 (m, 9H), 1.30 (d, J=1.7 Hz, 9H). MS m/z (ESI+): Calc [M+Na]+=637.2; Exp [M+Na]+=637.2. HPLC Method 2 retention time=6.75 min.

1.2.2.3) Synthesis of (2S,3R,4S,5S,6S)-2-(4-(2-((tert-butoxycarbonyl)amino)-1-(((4-nitrophenoxy)carbonyl)oxy)ethyl)-2-nitrophenoxy)-6-(methoxycarbonyl)tetrahydro-2H-pyran-3,4,5-triyl triacetate Previous compound (2S,3R,4S,5S,6S)-2-(4-(2-((tert-butoxycarbonyl)amino)-1-hydroxyethyl)-2-nitrophenoxy)-6-(methoxycarbonyl)tetrahydro-2H-pyran-3,4,5-triyl triacetate (334 mg/0.54 mmol) and 4-nitrophenyl chloroformate (219 mg/1.09 mmol) were dissolved in 6 mL of dry DCM at 0° C. Anhydrous pyridine (112 mg/1.41 mmol) was added and the mixture was stirred 30 min at room temperature. The reaction was filtered over a 0.45 μm PTFE filter and purified by chromatography on silica gel (petroleum ether/EtOAc, gradient from 85:15 to 30:70) to afford title compound (380 mg/90%) as a yellow foam. 1H NMR (300 MHZ, DMSO-d6) δ 8.39-8.26 (m, 2H), 7.93 (d, J=2.2 Hz, 1H), 7.75 (d, J=8.8 Hz, 1H), 7.55 (dd, J=9.2, 1.2 Hz, 2H), 7.46 (d, J=8.8 Hz, 1H), 7.20 (d, J=4.8 Hz, 1H), 5.77 (dd, J=7.7, 3.7 Hz, 1H), 5.47 (t, J=9.5 Hz, 1H), 5.11 (q, J=9.6 Hz, 2H), 4.77 (d, J=9.9 Hz, 1H), 3.73-3.59 (m, 3H), 3.59-3.37 (m, 2H), 2.05-1.96 (m, 9H), 1.48-1.35 (m, 1H), 1.32 (s, 9H). MS m/z (ESI+): Calc [M+Na]+=802.15; Exp [M+Na]+=802.15. HPLC Method 2 retention time=8.5 min.

1.2.2.4) Synthesis of Compound INT2

381 mg (0.49 mmol) of previous compound (2S,3R,4S,5S,6S)-2-(4-(2-((tert-butoxycarbonyl)amino)-1-(((4-nitrophenoxy)carbonyl)oxy)ethyl)-2-nitrophenoxy)-6-(methoxycarbonyl)tetrahydro-2H-pyran-3,4,5-triyl triacetate, 200 mg (0.38 mmol) of Exatecan Mesylate and 51 mg (0.38 mmol) of HOBt were dissolved in 5 mL of a 85:15 (v/v) mixture of anhydrous DMF/pyridine. 53.5 mg (0.51 mmol) of DIPEA was added. The reaction was stirred 2 hours at 40° C. and volatiles were evaporated under reduced pressure. The crude residue was purified by chromatography on silica gel (DCM/MeOH gradient from 99:1 to 95:5) to afford 360 mg (87%) of intermediate compound (2S,3R,4S,5S,6S)-2-(4-(2-((tert-butoxycarbonyl)amino)-1-((((1R,9R)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)carbamoyl)oxy)ethyl)-2-nitrophenoxy)-6-(methoxycarbonyl)tetrahydro-2H-pyran-3,4,5-triyl triacetate as a yellow/greenish solid. ESI+ [M+Na]+=1098.3. HPLC Method 3 retention time=14.7 and 14.9 min (diastereoisomeric mixture).

355 mg (0.33 mmol) of this intermediate compound was dissolved in 8 mL of MeOH/THF 75:25 at 0° C. LiOH monohydrate (138 mg/3.3 mmol) was dissolved in water (1 mL) and was added to the reaction vessel. After stirring at 0° C. for 30 min (reaction followed by HPLC), the mixture was neutralized with acetic acid (258 mg/4.3 mmol) and concentrated under reduced pressure. The obtained crude was re-dissolved at 0° C. with a TFA/DCM (30:70 v/v) solution and stirred 20 minutes at room temperature. Volatiles were evaporated under reduced pressure, the crude residue was taken up in a water/ACN (1:1 v/v) solution and purified using HPLC preparative method 5 to afford 172 mg (62%) of compound INT2 as a yellow solid. ESI+ [M+H]+=836.2. HPLC Method 3 retention time=7.3 and 7.8 min (diastereoisomeric mixture).

1.2.2.5) Synthesis of Stereopure Compound INT2-S and INT2-R

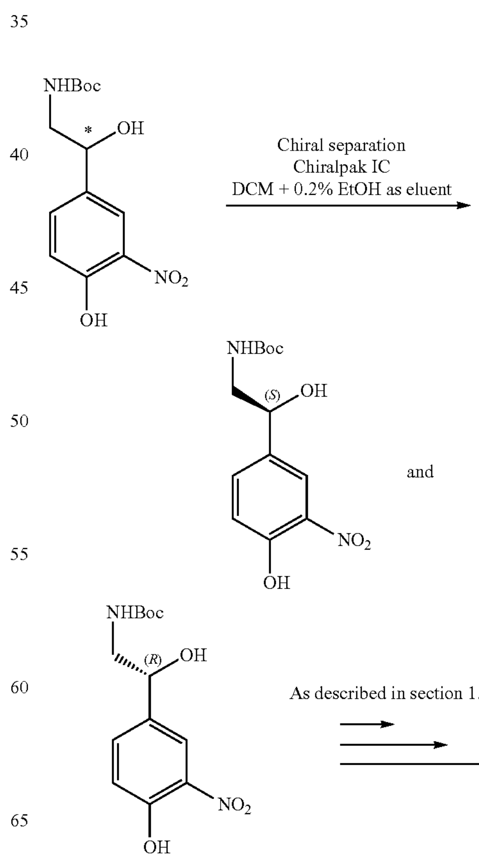

-continued

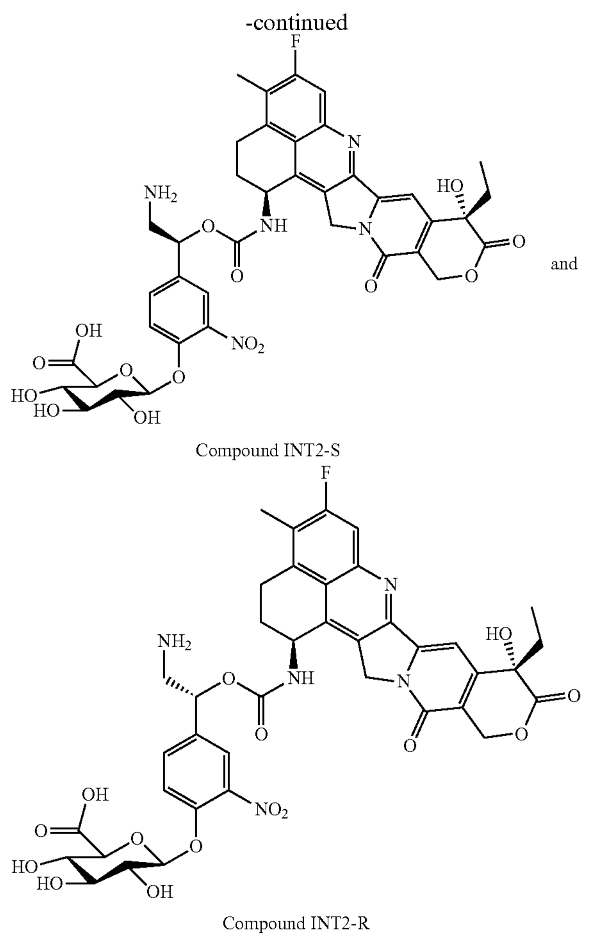

and

Compound INT2-S

Compound INT2-R

1.2.2.5.1) Chiral Separation of Racemic Mixture of Tert-Butyl(2-hydroxy-2-(4-hydroxy-3-nitrophenyl) ethyl)carbamate Chiral separation of racemic tert-butyl(2-hydroxy-2-(4-hydroxy-3-nitrophenyl)ethyl)carbamate (synthesized as previously described) was performed using Chiralflash® IC MPLC column 30×100 mm, 20 μm (Daicel cat #83M73) on a Teledyne Isco CombiFlash® Rf200 system. Mobile phase was DCM+0.2% (v/v) EtOH (isocratic gradient). Flow rate was 12 mL/min. Sample solvent was DCM+0.2% (v/v) EtOH. Mass recovery of the two enantiomers after separation was above 80%.

tert-butyl(S)-(2-hydroxy-2-(4-hydroxy-3-nitrophenyl) ethyl)carbamate retention time was 15 min, whereas tert-butyl (R)-(2-hydroxy-2-(4-hydroxy-3-nitrophenyl)ethyl) carbamate retention time was 25 min.

To determine absolute configuration, phenolic position of both enantiomers was esterified with 1.2 molar equivalents of 4-nitrobenzoyl chloride and 2 molar equivalents of triethylamine in anhydrous THF. Compounds were purified by chromatography on silica gel (petroleum ether/EtOAc, gradient from 90:10 to 10:90) to afford 4-(2-((tert-butoxycarbonyl)amino)-1-hydroxyethyl)-2-nitrophenyl 4-nitrobenzoate. 1H NMR (300 MHz, DMSO-d6) δ 8.51 (d, J=9.1 Hz, 2H), 8.44 (d, J=9.1 Hz, 2H), 8.19 (d, J=1.9 Hz, 1H), 7.88 (d, J=10.2 Hz, 1H), 7.72 (d, J=8.4 Hz, 1H), 6.93 (t, J=5.9 Hz, 1H), 5.84 (d, J=4.7 Hz, 1H), 4.86-4.76 (m, 1H), 3.24 (t, J=6.1 Hz, 2H), 1.38 (s, 9H). ESI+ [M+Na]+=470.1. Absolute configuration of enantiomers (previously dissolved in a 1:1 mixture of heptane/dichloromethane and allowed to slowly evaporate for 3 weeks to induce the formation of crystals) was confirmed by x-ray crystallography. A block-shaped crystal was mounted on a nylon loop in perfluoroether oil. Data were collected using a Xcalibur, Atlas, Gemini ultra-diffractometer equipped with an Oxford Cryosystems low-temperature device operating at T=150.00 (5) K. Data were measured using ω scans using Cu Kα radiation. The structure was solved with the ShelXT solution program using dual methods and by using Olex2 (O. V. Dolomanov et al., Olex2: A complete structure solution, refinement and analysis program, J. Appl. Cryst., 2009, 42, 339-341) as the graphical interface. The model was refined with ShelXL 2018/3 (Sheldrick, G. M., Crystal structure refinement with ShelXL, Acta Cryst., 2015, C71, 3-8) using full matrix least squares minimisation on F2.

1.2.2.5.2) Synthesis of Stereopure INT2-S and INT2-R Compounds

Stereopure compounds INT2-S and INT2-R were synthesized as described in previous section 1.2.2, without any appreciable changes in reaction conditions, reactivity or overall yields.

Final purification using HPLC preparative method 5 afforded 33 mg of compound INT2-S as a yellow solid. ESI+ [M+H]+=836.2. HPLC Method 3 retention time=7.3 min.

Final purification using HPLC preparative method 5 afforded 21 mg of compound INT2-R as a yellow solid. ESI+ [M+H]+=836.2. HPLC Method 3 retention time=7.8 min.

1.2.3) Synthesis of Compound INT3

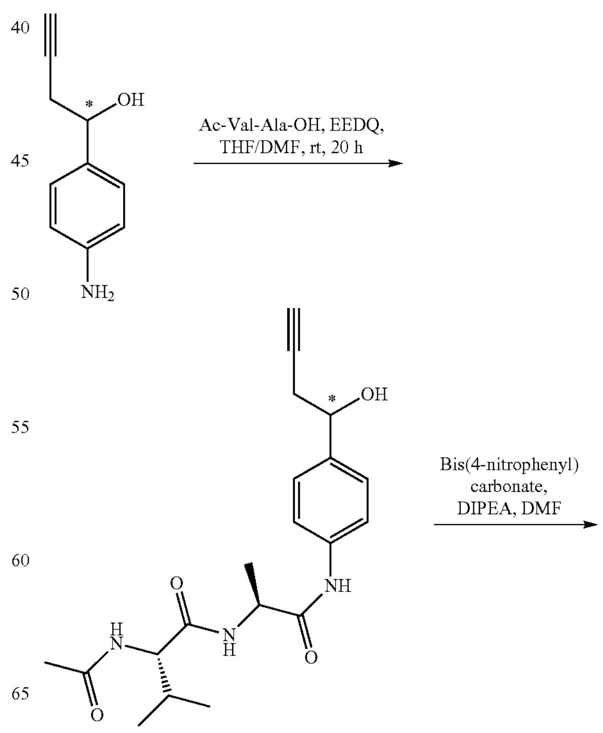

-continued

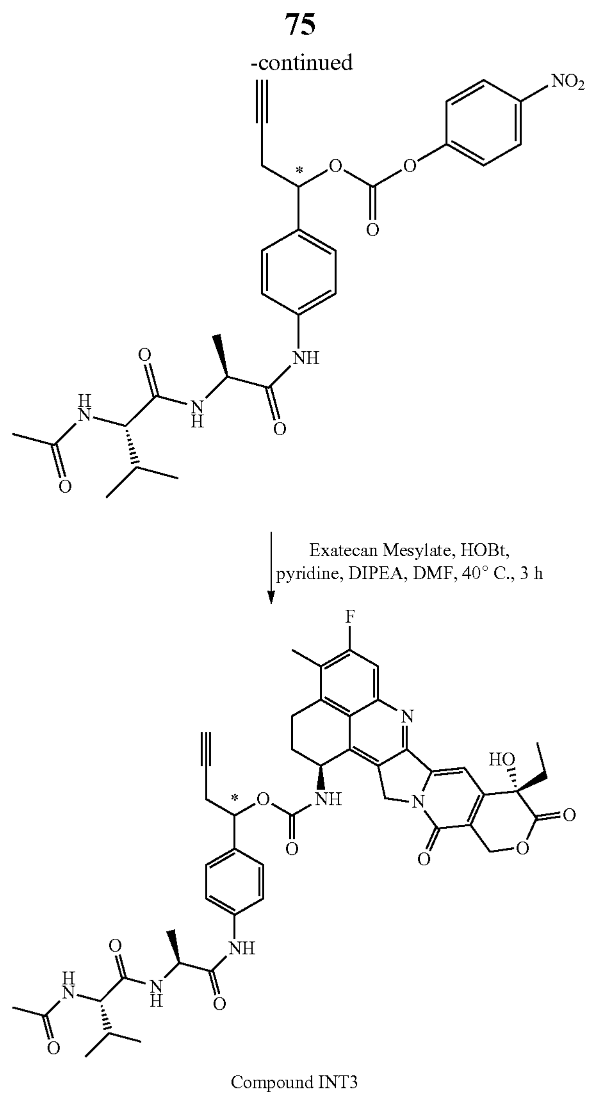

Compound INT3

1.2.3.1) Synthesis of Ac-Val-Ala-OH (Acetyl-L-Valyl-L-Alanine)

To a solution of L-alanine benzyl ester hydrochloride (542 mg/2.5 mmol) in 30 mL of DCM were sequentially added triethylamine (254 mg/2.5 mmol), distilled water (30 mL), N-α-Acetyl-L-valine (400 mg/2.5 mmol) and HOBt (339 mg/2.5 mmol). The mixture was then cooled to 0° C. and EDC-HCl (530 mg/2.75 mmol) was added. The resulting mixture was stirred at 0° C. overnight. The reaction was diluted with 20 mL of 2M HCl and the layers were separated. The organic phase was washed 2 times with 2M HCl, 2 times with saturated $NaHCO_3$ solution and once with saturated NaCl solution. The organic phase was dried over $MgSO_4$, filtered and evaporated under vacuum to afford 714 mg (89%) of benzyl acetyl-L-valyl-L-alaninate as a white solid intermediate.

This intermediate was solubilized in 10 mL of EtOAc/MeOH 1:1 (v/v) and was transferred into a stainless steel hydrogenation reactor. After a first argon purge, a catalytic amount of 5% wt Pd/C was added. The reactor was then purged twice with $H_2$ and kept under a $H_2$ pressure of 10 bar overnight at room temperature. After filtration of the reaction with a 0.45 μm PTFE filter and solvent removal under vacuum, a quantitative amount of pure acetyl-L-valyl-L-alanine was obtained as a white solid. 1H NMR (300 MHZ, DMSO-d6) δ 12.45 (s, 1H), 8.23 (d, J=6.9 Hz, 1H), 7.85 (d, J=9.0 Hz, 1H), 4.25-4.11 (m, 2H), 1.94 (dt, J=13.6, 6.8 Hz, 1H), 1.85 (s, 3H), 1.26 (d, J=7.3 Hz, 3H), 0.85 (dd, J=12.1, 6.8 Hz, 6H).

1.2.3.2) Synthesis of (2S)-2-acetamido-N-((2S)-1-((4-(1-hydroxybut-3-yn-1-yl)phenyl)amino)-1-oxopropan-2-yl)-3-methylbutanamide In a round bottom flash, 420 mg (2.60 mmol) of 1-(4-aminophenyl) but-3-yn-1-ol (synthesized following procedures described in Sharma A. et al., Chem 2018, 4 (10), 2370-2383) and 600 mg (2.60 mmol) of previous compound Ac-Val-Ala-OH were suspended in 20 ml of anhydrous THF. 676 mg (2.74 mmol) of 2-Ethoxy-1-ethoxycarbonyl-1,2-dihydroquinoline (EEDQ) previously dissolved in 5 mL of anhydrous DMF was then into the flask and the turbid reaction mixture was stirred overnight at room temperature. Volatiles were then evaporated under reduced pressure and the crude residue was dry-loaded and purified by chromatography on silica gel (DCM/MeOH gradient from 99:1 to 85:15) to afford 809 mg (83%) of title compound as a white solid. 1H NMR (300 MHZ, DMSO-d6) δ 9.84 (s, 1H), 8.18 (d, J=7.0 Hz, 1H), 7.90 (d, J=8.6 Hz, 1H), 7.53 (d, J=8.6 Hz, 2H), 7.28 (d, J=8.6 Hz, 2H), 5.44 (d, J=4.4 Hz, 1H), 4.62 (q, J=6.2 Hz, 1H), 4.39 (p, J=7.6, 7.2 Hz, 1H), 4.17 (dd, J=8.5, 6.8 Hz, 1H), 2.70 (t, J=2.6 Hz, 1H), 1.96 (dt, J=13.2, 6.6 Hz, 1H), 1.88 (s, 3H), 1.30 (d, J=7.1 Hz, 3H), 0.86 (dd, J=10.9, 6.8 Hz, 6H). ESI+ [M+H]+=374.2. HPLC Method 2 retention time=3.95 min.

1.2.3.3) Synthesis of 1-(4-((S)-2-((S)-2-acetamido-3-methylbutanamido)propanamido)phenyl) but-3-yn-1-yl(4-nitrophenyl)carbonate 94 mg (0.25 mmol) of (2S)-2-acetamido-N-((2S)-1-((4-(1-hydroxybut-3-yn-1-yl)phenyl)amino)-1-oxopropan-2-yl)-3-methylbutanamide and 153 mg (0.50 mmol) of bis(4-nitrophenyl)carbonate were dissolved in 2 mL of anhydrous DMF. 98 mg (0.76 mmol) of DIPEA were added and the reaction mixture was stirred overnight at room temperature. Volatiles were removed under reduced pressure and the crude residue was purified by chromatography on silica gel (DCM/MeOH gradient from 99:1 to 90:10) to afford 118 mg (87%) of title compound as a yellow solid. 1H NMR (300 MHZ, DMSO-d6) δ 9.99 (s, 1H), 8.35-8.26 (m, 2H), 8.22 (d, J=7.0 Hz, 1H), 7.89 (d, J=8.6 Hz, 1H), 7.63 (d, J=8.7 Hz, 2H), 7.58-7.48 (m, 2H), 7.43 (d, J=8.7 Hz, 2H), 5.74 (d, J=7.5 Hz, 1H), 4.39 (p, J=7.2 Hz, 1H), 4.17 (dd, J=8.5, 6.9 Hz, 1H), 3.01-2.84 (m, 3H), 1.99-1.91 (m, 1H), 1.88 (s, 3H), 1.31 (d, J=7.1 Hz, 3H), 0.86 (dd, J=11.2, 6.8 Hz, 6H). ESI+ [M+H]+=539.1. HPLC Method 2 retention time=6.48 min.

1.2.3.4) Synthesis of Compound INT3

43 mg (0.081 mmol) of previous compound 1-(4-((S)-2-((S)-2-acetamido-3-methylbutanamido)propanamido)phenyl) but-3-yn-1-yl(4-nitrophenyl)carbonate, 55.5 mg (0.11) of Exatecan Mesylate and 11.0 mg (0.08 mmol) of HOBt were dissolved in 2 mL of a 85:15 (v/v) mixture of anhydrous DMF/pyridine. 11.5 mg (0.09 mmol) of DIPEA was added. The reaction was stirred 3 hours at 40° C. After removal of volatiles under reduced pressure, the reaction mixture was purified by chromatography on silica gel (DCM/MeOH gradient from 99:1 to 95:5) to afford 42 mg (62%) of compound INT3 as a yellow/greenish solid. ESI+

[M+H]+=835.3. HPLC Method 2 retention time=6.50 and 6.60 min (diastereoisomeric mixture).

1.2.4) Synthesis of Compound INT4, INT4-S and INT4-R

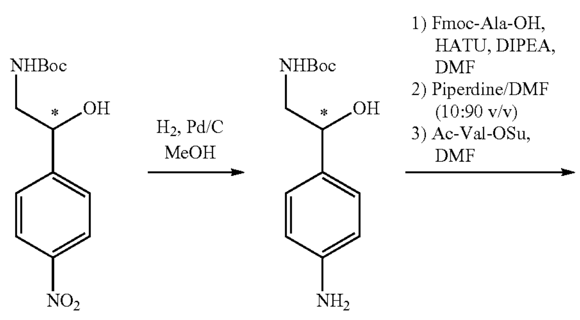

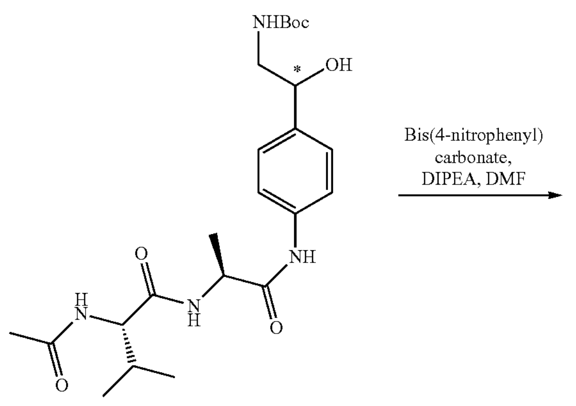

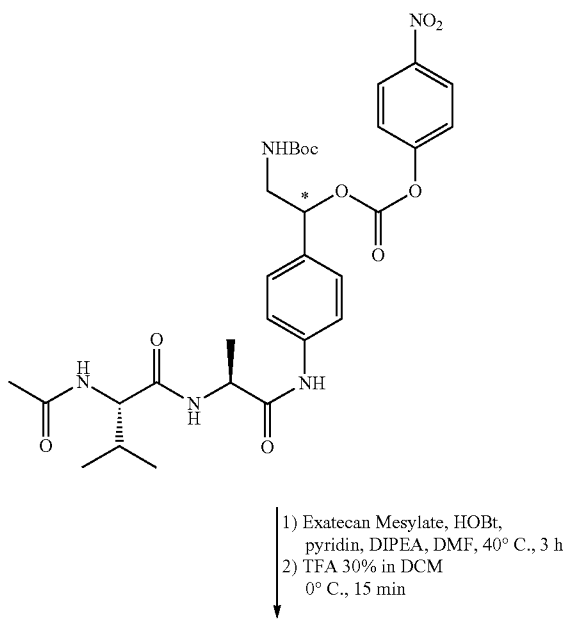

-continued

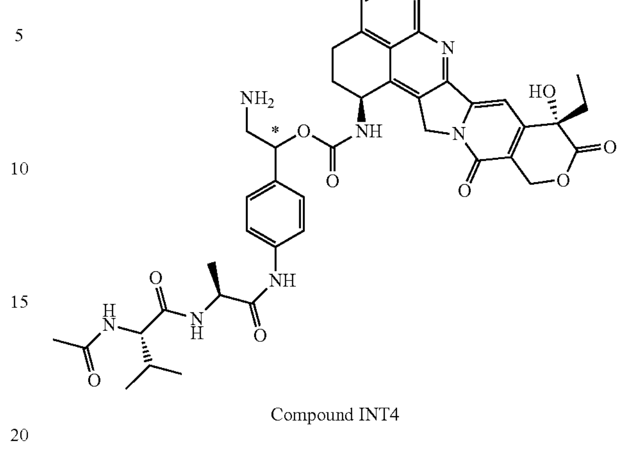

Compound INT4

1.2.4.1) Synthesis of tert-butyl(2-(4-aminophenyl)-2-hydroxyethyl)carbamate

A MeOH solution containing 911 mg (3.23 mmol) of commercially available tert-butyl(2-5 hydroxy-2-(4-nitrophenyl)ethyl)carbamate (CAS #939757-25-2) was transferred into a stainless steel hydrogenation reactor. After a first argon purge, a catalytic amount of 5% wt Pd/C was added. The reactor was then purged twice with $H_2$ and kept under a $H_2$ pressure of 10 bar for 5 hours at room temperature, while keeping the reaction stirred. After filtration of the reaction with a 0.45 μm PTFE filter and MeOH removal under 10 vacuum, 749 mg (92%) of title compound was obtained as a white solid. ESI+ [M+H]+=253.2. HPLC Method 2 retention time=2.73 min.

1.2.4.2) Synthesis of tert-butyl(2-(4-((S)-2-((S)-2-acetamido-3-methylbutanamido)propanamido)phenyl)-2-hydroxyethyl)carbamate 150 mg (0.60 mmol) of previous compound tert-butyl(2-(4-aminophenyl)-2-hydroxyethyl)carbamate, 222 mg (0.71 mmol) of Fmoc-Ala-OH and 81 mg (0.62 mmol) of DIPEA were dissolved in 5 mL of anhydrous DMF. 181 mg (0.71 mmol) of HATU is added and the reaction is stirred at room temperature overnight. Volatiles were then removed under reduced pressure and the crude residue was purified by chromatography on silica gel (DCM/MeOH gradient from 100:0 to 90:10) to quantitatively afford the first intermediate tert-butyl(2-(4-((S)-2-((((9H-fluoren-9-yl) methoxy)carbonyl)amino)propanamido)phenyl)-2-hydroxyethyl)carbamate that was directly engaged in Fmoc-deprotection. HPLC Method 2 retention time=7.7 min.

tert-butyl(2-(4-((S)-2-((((9H-fluoren-9-yl) methoxy)carbonyl)amino)propanamido)phenyl)-2-hydroxyethyl)carbamate was dissolved in 5 mL of DMF/piperidine 9:1 (v/v) and stirred 15 min at room temperature. Volatiles were then removed under reduced pressure and the crude residue was purified by chromatography on silica gel (DCM/MeOH gradient from 99:1 to 80:20) to afford 130 mg (68% over two steps) of the second intermediate tert-butyl(2-(4-((S)-2-aminopropanamido)phenyl)-2-hydroxyethyl)carbamate as a white foamy solid. HPLC Method 2 retention time=3.75 min.

130 mg (0.40 mmol) of tert-butyl(2-(4-((S)-2-aminopropanamido)phenyl)-2-hydroxyethyl)carbamate and 124 mg (0.48 mmol) of commercially available Ac-Val-OSu (CAS #56186-37-9) were dissolved in 3 mL of anhydrous DMF and the reaction mixture was stirred at room temperature overnight. Volatiles were then removed under reduced pressure and the crude residue was triturated with 3 mL of DCM to afford 95 mg (51%) of title compound as a white solid. 1H NMR (300 MHZ, DMSO-d6) δ 9.82 (s, 1H), 8.16 (d, J=7.1 Hz, 1H), 7.88 (d, J=8.6 Hz, 1H), 7.53 (d, J=8.4 Hz, 2H), 7.22 (d, J=8.5 Hz, 2H), 6.73-6.58 (m, 1H), 5.27 (d, J=4.4 Hz, 1H), 4.58-4.47 (m, 1H), 4.40 (q, J=7.1 Hz, 1H), 4.17 (dd, J=8.4, 6.8 Hz, 1H), 3.15-2.90 (m, 2H), 1.88 (s, 4H), 1.35 (s, 9H), 1.30 (d, J=7.1 Hz, 3H), 0.92-0.73 (m, 6H). ESI+ [M+H]+=487.3. HPLC Method 2 retention time=4.50 min.

1.2.4.3) Synthesis of tert-butyl(2-(4-((S)-2-((S)-2-acetamido-3-methylbutanamido)propanamido)phenyl)-2-(((4-nitrophenoxy)carbonyl)oxy)ethyl)carbamate 286 mg (0.62 mmol) of tert-butyl(2-(4-((S)-2-((S)-2-acetamido-3-methylbutanamido)propanamido)phenyl)-2-hydroxyethyl)carbamate and 375 mg (1.23 mmol) of bis(4-nitrophenyl)carbonate were dissolved in 3 mL of anhydrous DMF. 318 mg (2.46 mmol) of DIPEA were added and the reaction mixture was stirred 3 hours at room temperature. Volatiles were removed under reduced pressure and the crude residue was purified by chromatography on silica gel (DCM/MeOH gradient from 99:1 to 90:10) to afford 336 mg (87%) of title compound as a yellow solid. 1H NMR (300 MHZ, DMSO-d6) δ 9.99 (s, 1H), 8.36-8.26 (m, 2H), 8.22 (d, J=6.9 Hz, 1H), 7.89 (d, J=8.6 Hz, 1H), 7.63 (d, J=8.6 Hz, 2H), 7.56-7.46 (m, 2H), 7.34 (d, J=8.6 Hz, 2H), 7.22 (t, J=5.6 Hz, 1H), 5.68 (t, J=6.0 Hz, 1H), 4.38 (p, J=7.1 Hz, 1H), 4.17 (dd, J=8.5, 6.9 Hz, 1H), 3.49-3.34 (m, 2H), 2.01-1.90 (m, 1H), 1.87 (s, 3H), 1.37 (s, 9H), 1.30 (d, J=7.1 Hz, 3H), 0.86 (dd, J=11.1, 6.8 Hz, 6H). ESI+ [M+Na]+=652.2. HPLC HPLC Method 2 retention time=7.13 min.

1.2.4.4) Synthesis of Compound INT4

231 mg (0.37 mmol) of previous compound tert-butyl(2-(4-((S)-2-((S)-2-acetamido-3-methylbutanamido)propanamido)phenyl)-2-(((4-nitrophenoxy)carbonyl)oxy)ethyl)carbamate, 150 mg (0.28) of Exatecan Mesylate and 38 mg (0.28 mmol) of HOBt were dissolved in 5 mL of a 85:15 (v/v) mixture of anhydrous DMF/pyridine. 40 mg (0.31 mmol) of DIPEA was added. The reaction was stirred 3 hours at 40° C. and volatiles were evaporated under reduced pressure. The crude residue was purified by chromatography on silica gel (DCM/MeOH gradient from 99:1 to 90:10). 220 mg of intermediate (85%) compound 1-(4-((S)-2-((S)-2-acetamido-3-methylbutanamido)propanamido)phenyl)-2-((tert-butoxycarbonyl)amino)ethyl((1R,9R)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)carbamate was obtained at a brown yellow solid. ESI+ [M+H]+=926.4. HPLC Method 2 retention time=6.7 and 6.8 min (diastereoisomeric mixture).

The obtained solid was re-dissolved at 0° C. with a TFA/DCM (30:70 v/v) solution and stirred 20 minutes at room temperature. Volatiles were evaporated under reduced pressure, the crude residue was taken up in a water/ACN (1:1 v/v) solution and purified using HPLC preparative method 5 to afford 171.4 mg (73%) of compound INT4 as a yellow solid. ESI+ [M+H]+=826.4. HPLC Method 3 retention time=8.3 and 8.75 min (diastereoisomeric mixture).

1.2.4.5) Synthesis of Stereopure Compounds INT4-S and INT4-R

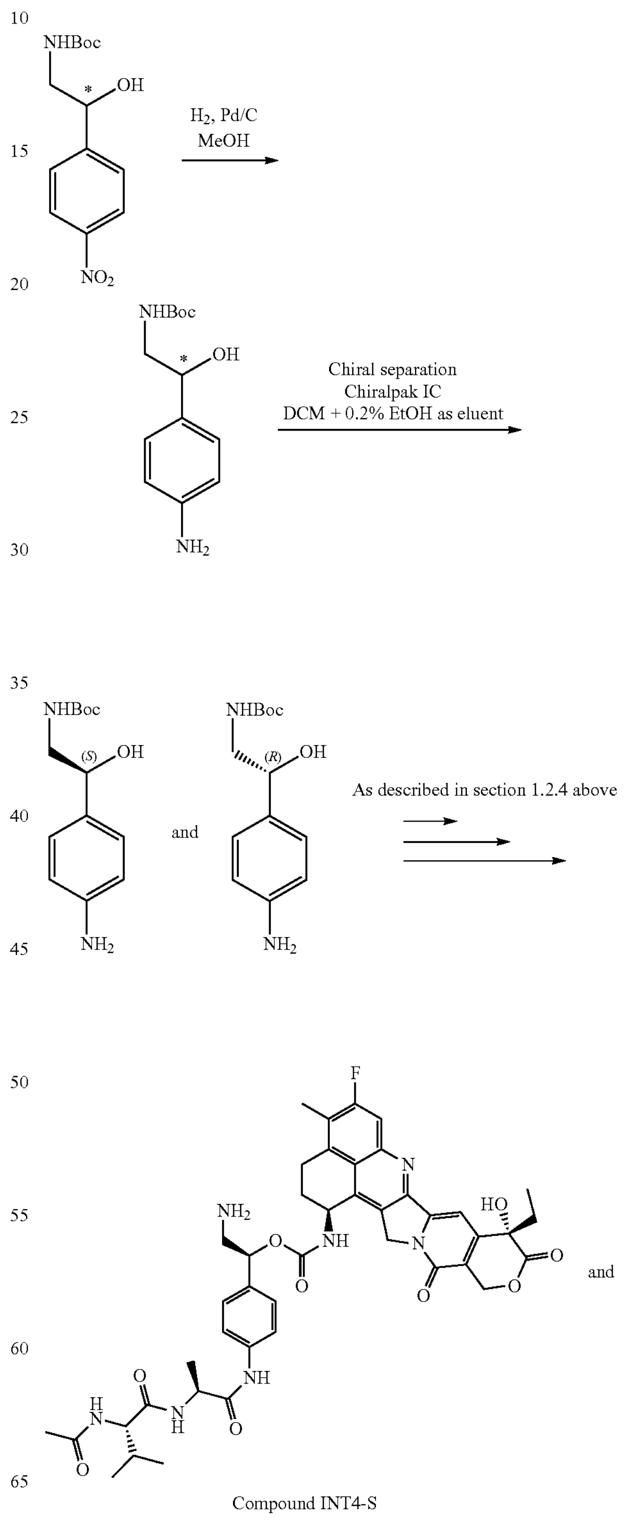

and

Compound INT4-S

-continued

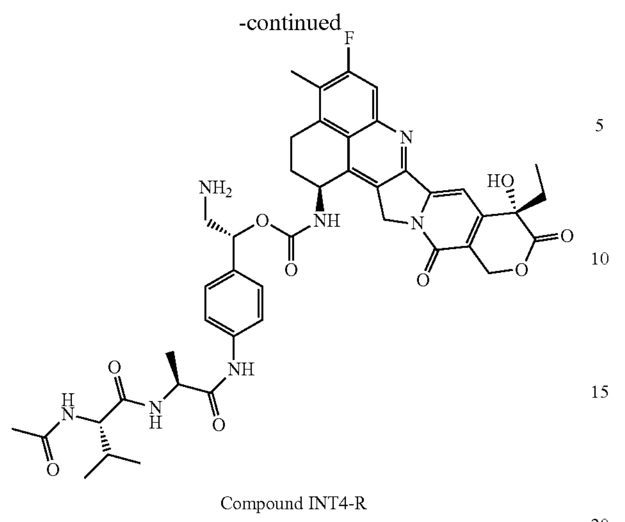

Compound INT4-R 1.2.4.5.1) Chiral Separation of Racemic Mixture of tert-butyl(2-(4-aminophenyl)-2-hydroxyethyl)carbamate Chiral separation of racemic tert-butyl(2-(4-aminophenyl)-2-hydroxyethyl)carbamate was performed using Chiralflash® IC MPLC column 30×100 mm, 20 μm (Daicel cat #83M73) on a Teledyne Isco CombiFlash® Rf200 system. Mobile phase was DCM+0.2% (v/v) EtOH (isocratic gradient). Flow rate was 12 mL/min. Sample solvent was DCM+0.2% (v/v) EtOH. Mass recovery of the two enantiomers after separation was above 75%.

tert-butyl(S)-(2-(4-aminophenyl)-2-hydroxyethyl)carbamate retention time was 21 min, whereas tert-butyl (R)-(2-(4-aminophenyl)-2-hydroxyethyl)carbamate retention time was 29 min. Absolute configuration of the enantiomers (previously dissolved in a 1:1 mixture of heptane/ethanol and allowed to slowly evaporate for 1 week to induce the formation of crystals) was confirmed by x-ray crystallography. A block-shaped crystal was mounted on a nylon loop in perfluoroether oil. Data were collected using a Xcalibur, Atlas, Gemini ultra-diffractometer equipped with an Oxford Cryosystems low-temperature device operating at T=150.00 (10) K. Data were measured using ω scans using Cu Kα radiation. The structure was solved with the ShelXT solution program using dual methods and by using Olex2 (O. V. Dolomanov et al., Olex2: A complete structure solution, refinement and analysis program, J. Appl. Cryst., 2009, 42, 339-341) as the graphical interface. The model was refined with ShelXL 2018/3 (Sheldrick, G. M., Crystal structure refinement with ShelXL, Acta Cryst., 2015, C71, 3-8) using full matrix least squares minimization on F2.

1.2.4.5.2) Synthesis of Stereopure INT4-S and INT4-R Compounds

Stereopure compounds INT4-S and INT4-R were synthesized as described in previous section 1.2.4, without any appreciable changes in reaction conditions, reactivity or overall yields.

Final purification using HPLC preparative method 5 afforded 54 mg of compound INT4-S as a yellow solid. ESI+ [M+H]+=826.4. HPLC Method 3 retention time=8.45 min.

Final purification using HPLC preparative method 5 afforded 46 mg of compound INT4-R as a yellow solid. ESI+ [M+H]+=826.4. HPLC Method 3 retention time=8.90 min.

1.3) Synthesis of Drug-Linkers 1.3.1) Synthesis of Glucuronide-Based Drug-Linkers 1.3.1.1) Synthesis of Compound LNK1

Compound LNK1

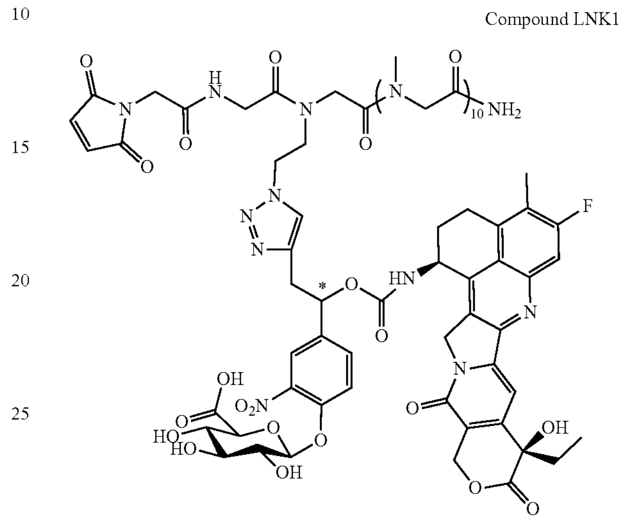

44.5 mg (0.049 mmol) of compound PSR1 (azide-polysarcosine intermediate) and 27.5 (0.033 mmol) of compound INT1 (alkyne-payload) were dissolved in a 1:1 (v/v) solution of 100 mM PBS (pH=7.5) and DMSO, in order to reach a 0.060M concentration of compound INT1. Freshly prepared CuSO4 pentahydrate and sodium ascorbate solutions (approximately 250 mg/mL) were then sequentially added into the reaction vial in order to reach 0.08 molar equivalent Cu and 1 molar equivalent of sodium ascorbate (based on compound INT1 molar equivalent in the reaction mixture). The reaction is purged with argon and stirred at 40° C. The reaction is monitored by HPLC and was complete in less than 2 hours. The reaction mixture is then diluted with a 0.1% TFA solution in water/ACN 1:1 (v/v) and purified using HPLC preparative method 5 to afford 44 mg (77% based on starting compound INT1) of intermediate compound (2S,3S,4S,5R,6S)-6-(4-(2-(1-(35-amino-3-glycyl-6,9,12,15,18,21,24,27,30,33-decamethyl-5,8,11,14,17,20,23,26,29,32,35-undecaoxo-3,6,9,12,15,18,21,24,27,30,33-undecaazapentatriacontyl)-1H-1,2,3-triazol-4-yl)-1-((((1R,9R)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)carbamoyl)oxy)ethyl)-2-nitrophenoxy)-3,4,5-trihydroxytetrahydro-2H-pyran-2-carboxylic acid as a yellow solid. ESI+ [M+H]+=1755.7. HPLC Method 3 retention time=7.51 min and 7.82 min (diastereoisomeric mixture).

26.0 mg (0.015 mmol) of this compound and 4.11 mg (0.016 mmol) of maleimidoacetic acid N-hydroxysuccinimide ester were dissolved in anhydrous DMF (0.1M concentration of maleimide compound). 2.25 mg (0.022 mmol) of triethylamine was added and the reaction was stirred for 2 hours until entire conversion of the reaction was observed by HPLC. The reaction mixture was then diluted with a 1% TFA solution in water/ACN 1:1 (v/v) and purified using HPLC preparative method 6 to afford 16.0 mg (57%) of compound LNK1 as a yellow solid. ESI+ [M+H]+=1892.7. HPLC Method 3 retention time=7.95 min and 8.20 min (equimolar diastereoisomeric mixture).

1.3.1.2) Synthesis of Compound LNK2

Compound LNK2

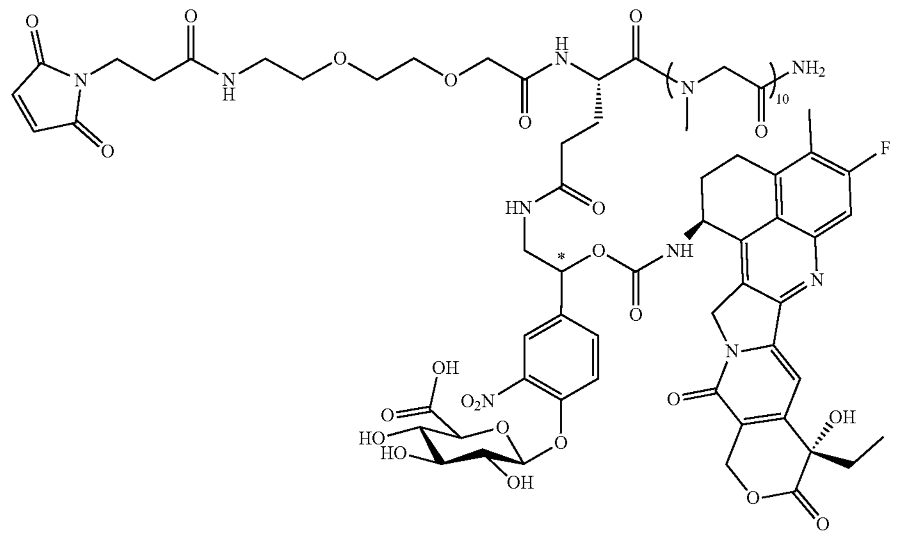

409 mg (0.31 mmol) of compound PSR3 (NHS-activated polysarcosine intermediate) and 172 mg (0.21 mmol) of compound INT2 ($NH_2$-payload) were dissolved in anhydrous DMF in a small vial (0.080M concentration of compound INT2). 83.5 mg (0.83 mmol) of triethylamine was added and the reaction was stirred 30 min at room temperature. After entire conversion of the reaction as observed by HPLC, piperidine is directly added into the reaction vial in order to reach a 8% (v/v) piperidine solution in DMF. The reaction is then stirred at room temperature 5-10 min, until entire Fmoc-deprotection is observed by HPLC. The reaction is slowly neutralized with a 10% TFA solution in water/ACN 1:1 (v/v) and purified using HPLC preparative method 5 to afford 254 mg (67% yield based on starting compound INT2) of intermediate compound (2S,3S,4S,5R,6S)-6-(4-((9S)-40-amino-9-(2-(2-(2-aminoethoxy) ethoxy) acetamido)-1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl) amino)-11,14,17,20,23,26,29,32,35,38-decamethyl-1,6,10,13,16,19,22,25,28,31,34,37,40-tridecaoxo-2-oxa-5,11,14,17,20,23,26,29,32,35,38-undecaazatetracontan-3-yl)-2-nitrophenoxy)-3,4,5-trihydroxytetrahydro-2H-pyran-2-carboxylic acid as a yellow solid. ESI+ [M+H]+=1819.7. HPLC Method 2 retention time=4.60 min and 4.69 min (equimolar diastereoisomeric mixture).

254 mg (0.14 mmol) of this compound and 39.1 mg (0.15 mmol) of maleimidoacetic acid N-hydroxysuccinimide ester were dissolved in anhydrous DMF (0.1M concentration of maleimide compound). 22.6 mg (0.22 mmol) of triethylamine was added and the reaction was stirred for 1 hour until entire conversion of the reaction as observed by HPLC. The reaction mixture is then diluted with a 1% TFA solution in water/ACN 1:1 (v/v) and purified using HPLC preparative method 6 to afford 161 mg (58%) of final compound LNK2 as a yellow solid. HRMS m/z (ESI+): Calc [M+2H]2+ =985.8900; Exp [M+2H]2+=985.8896; Error=0.4 ppm. HPLC Method 2 retention time=7.9 min and 8.1 min (equimolar diastereoisomeric mixture).

1.3.1.3) Synthesis of Compound LNK2-S and LNK2-R

Compound LNK2-S

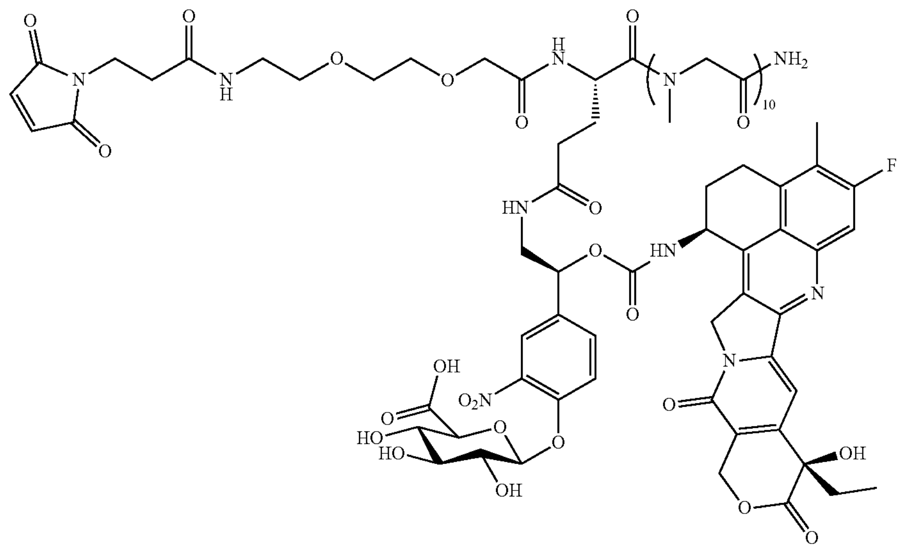

Compound LNK2-R

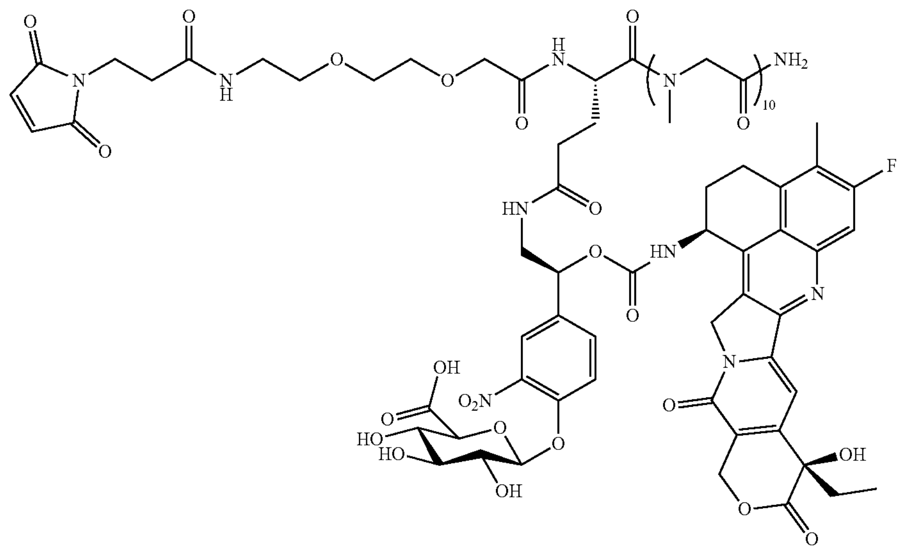

Compound LNK-2-S and LNK2-R were synthesized as described above, using the same procedure that was used for compound LNK2. Starting materials were respectively compound INT2-S and INT2-R (NH2-payload) and compound PSR3 (NHS-activated polysarcosine intermediate).

53.4 mg of compound LNK2-S was obtained as a yellow solid. ESI+ [M+2H]2+=985.9. HPLC Method 3 retention time=7.8 min.

44.0 mg of compound LNK2-R was obtained as a yellow solid. ESI+ [M+2H]2+=985.9. HPLC Method 3 retention time=8.1 min.

1.3.2) Synthesis of Dipeptide-Based Drug-Linkers 1.3.2.1) Synthesis of Compound LNK3

Compound LNK3

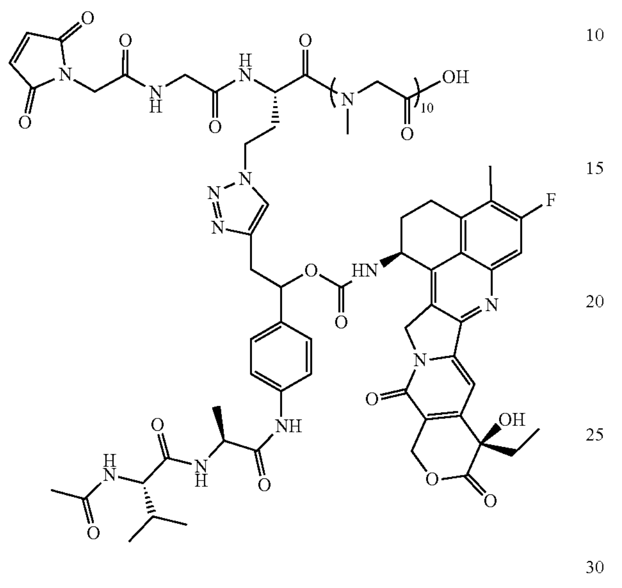

Final compound LNK3 was synthesized as described above, using the same procedure that was used for compound LNK1. Starting materials were compound PSR2 (azide-polysarcosine intermediate) and compound INT3 (alkyne-payload).

14.0 mg (36% over two steps) of compound LNK3 was obtained as a yellow solid. ESI+ [M+H]+=1883.8. HPLC Method 3 retention time=8.82 min and 9.07 min (equimolar diastereoisomeric mixture).

1.3.2.2) Synthesis of Compound LNK4

Compound LNK4

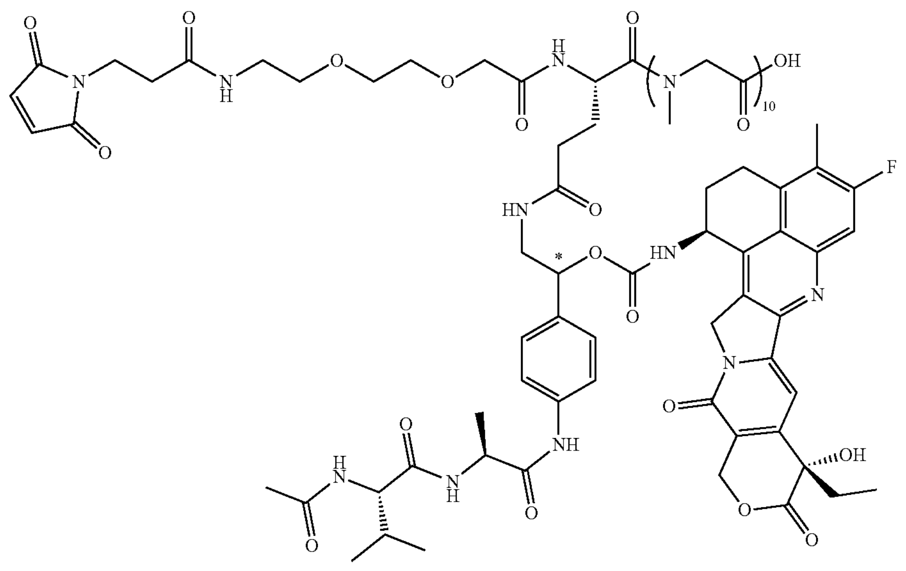

Compound LNK4 was synthesized as described above, using the same procedure that was used for compound LNK2. Starting materials were compound PSR4 (NHS-activated polysarcosine intermediate) and compound INT4 (NH2-payload).

34.9 mg (46% over two steps) of compound LNK4 was obtained as a yellow solid. HRMS m/z (ESI+): Calc [M+2H]2+=981.4394; Exp [M+2H]2+=981.4398; Error=−0.4 ppm. HPLC Method 3 retention time=8.81 min and 8.94 min (equimolar diastereoisomeric mixture).

1.3.2.3) Synthesis of Compound LNK4-S and LNK4-R

Compound LNK4-S

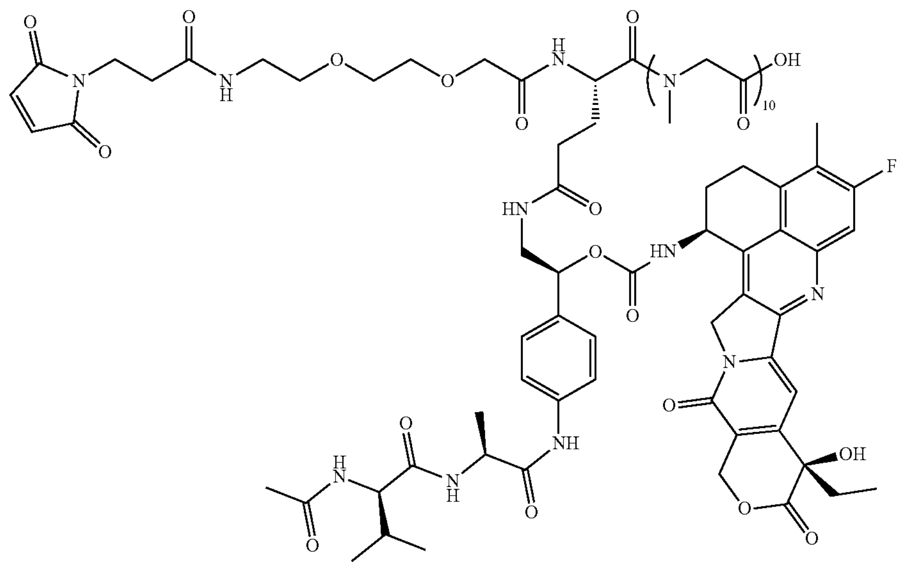

Compound LNK4-R

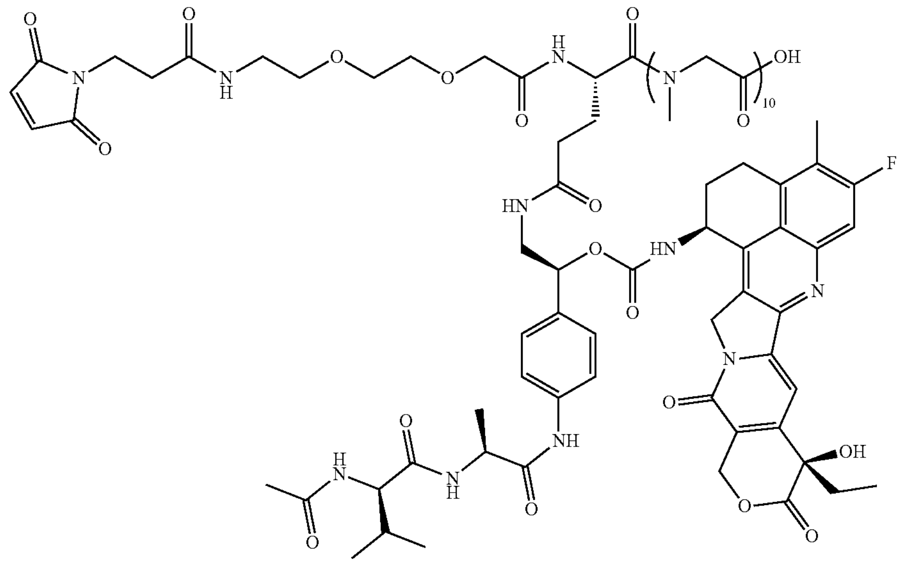

Compound LNK4-S and LNK4-R were synthesized as described above, using the same procedure that was used for compound LNK2. Starting materials were respectively compound INT4-S and INT4-R (NH2-payload) and compound PSR4 (NHS-activated polysarcosine intermediate).

18.1 mg of compound LNK4-S was obtained as a yellow solid. ESI+ [M+2H]2+=981.4. HPLC Method 3 retention time=8.78 min.

16.3 mg of compound LNK4-R was obtained as a yellow solid. ESI+ [M+2H]2+=981.4. HPLC Method 3 retention time=8.96 min.

Example 2: Preparation and Characterization of Antibody-Drug Conjugates 2.1) Antibody Production Monoclonal antibodies amino acid sequences were obtained from the literature. Farletuzumab light (SEQ ID. 10) and heavy chain (SEQ ID. 11) sequences were obtained from the International Nonproprietary Names for Pharmaceutical Substances (INN) List 62, published in the World Health Organization (WHO) Drug Information Vol 23, No. 3, 2009 and from WO2017151979. Farletuzumab-LALA that includes Fc-silencing mutations L234A and L235A ("LALA") on the heavy chain (Wines et al. The Journal of Immunology May 15, 2000, 164 (10) 5313-5318) of farletuzumab was also produced (heavy chain "LALA" SEQ ID.

9 sequence). Mirvetuximab light (SEQ ID. 17) and heavy chain (SEQ ID. 16) sequences were obtained from patent application WO2011106528. Human IgG1k non-binding isotype control was cat #HG1K from Sino Biologicals (proprietary amino acid sequences). Trastuzumab (Herceptin® 150 mg) was purchased from Roche. Enhertu® (trastuzumab deruxtecan) was purchased from Daiichi Sankyo/AstraZeneca.

Monoclonal antibodies were produced by transient transfection of CHO K1 cells using art-recognized techniques (outsourced to Evitria AG, Switzerland). cDNAs were cloned into Evitria's vector system using conventional (non-PCR based) cloning techniques. pDNA was prepared under low-endotoxin conditions based on anion exchange chromatography. DNA concentration was determined by measuring the absorption at a wavelength of 260 nm. Correctness of the sequences was verified with Sanger sequencing (up to two sequencing reactions per plasmid). Suspension-adapted CHO K1 cells (originally received from ATCC and adapted to serum-free growth in suspension culture at Evitria) were used for antibody production. The seed was grown in Evitria's proprietary animal-component and serum-free medium. Cells were transfected with Evitria's proprietary transfection reagent. Supernatant was harvested by centrifugation and subsequent filtration (0.2 μm filter). The antibody was purified using MabSelect SuRe protein A purification resin (Cytiva) and SEC preparative resin. Purity of antibody materials was confirmed by SDS-PAGE and size exclusion chromatography and was over 95%. Endotoxin content was measured using the Charles River Endosafe PTS system.

2.2) Preparation of Cysteine-Conjugated Antibody-Drug Conjugates

A solution of antibody (10 mg/mL in PBS 7.4+1 mM EDTA) was treated with a required amount (2.2 molar equivalent for final ~DAR4 ADC or 14 molar equivalent for final DAR8 ADC) of tris(2-carboxyethyl) phosphine (TCEP) for 1-2 hours at 37° C. The reduced antibody was buffer-exchanged with potassium phosphate 100 mM pH 7.4+1 mM EDTA by three rounds of dilution/centrifugation using Amicon 30K centrifugal filters device (Millipore). For a final ~DAR4 ADC, 6 molar equivalents of drug-linker (from a 12 mM DMSO stock solution) was added to the antibody. For a final DAR8 ADC, 10-12 molar equivalents of drug-linker was added. The solution was incubated 30 min at room temperature. The final conjugate was buffer-exchanged/purified with either PBS pH 7.4 buffer or with histidine sucrose buffer (20 mM histidine buffer pH 6.0, 4% (w/v) sucrose+75 mM NaCl) by four rounds of dilution/centrifugation using Amicon 30K centrifugal filters device and were sterile-filtered (0.20 μm PES filter).

Final protein concentration was assessed spectrophotometrically at 280 nm using a Nanodrop One device (Thermo Fisher Scientific).

2.3) Characterization of Cysteine-Conjugated Antibody-Drug Conjugates

The resulting conjugates were characterized as follows: Drug-Antibody-Ratio (DAR) Assessment by Reverse Phase Liquid Chromatography-Mass Spectrometry (RPLC-MS):

Denaturing RPLC-QTOF analysis was performed using the HPLC method 4 described above in Example 1. Briefly, conjugates were eluted on an Agilent PLRP-S 1000 Å 2.1×150 mm 8 μm (80° C.) using a mobile phase gradient of water/acetonitrile+0.1% formic acid (0.4 mL/min) and detected using a Bruker Impact II™ Q-TOF mass spectrometer scanning the 500-3500 m/z range (ESI+). Data were deconvoluted using the MaxEnt algorithm included in the Bruker Compass® software.

Reverse Phase Liquid Chromatography (RPLC-UV):

Denaturing RPLC-UV analysis was also conducted on an Agilent 1100 HPLC-DAD system, using a slightly modified version of HPLC method 4 described above. Mobile phase modifier 0.1% formic acid was replaced with 0.1% TFA, and detection was made using a DAD UV absorbance only (no mass spectrometry detector).

Size Exclusion Chromatography (SEC):

SEC was performed on an Agilent 1100 HPLC system having an extra-column volume below 15 μL (equipped with short sections of 0.12 mm internal diameter peek tubing and a micro-volume UV flow cell). Column was an Agilent AdvanceBioSEC 300 Å 4.6×150 mm 2.7 μm (maintained at 30° C.). Mobile phase was 100 mM sodium phosphate and 200 mM sodium chloride (pH 6.8). 10% acetonitrile (v/v) was added to the mobile phase to minimize secondary hydrophobic interactions with the stationary phase and prevent bacterial growth. Flow rate was 0.35 mL/min. UV detection was monitored at 280 nm or any other relevant wavelengths.

2.4) Preparation of Lysine-Conjugated Antibody-Drug Conjugates

A solution of antibody mirvetuximab or farletuzumab (10 mg/mL in 100 mM $KH_2PO_4$ PH 8.0) was treated with a 12 mM DMSO solution of sulfo-SPDB-DM4 CAS #1626359-59-8 (MedChemExpress), reaching a 7.5 molar equivalent final concentration of sulfo-SPDB-DM4. The solution was incubated for 3 hours at room temperature and was filtered using a 0.20 μm PES filter. The final conjugate was buffer-exchanged/purified with either PBS pH 7.4 buffer or with histidine sucrose buffer (20 mM histidine buffer pH 6.0, 4% (w/v) sucrose+75 mM NaCl) by five rounds of dilution/centrifugation using Amicon 30K centrifugal filters device and were sterile-filtered (0.20 μm PES filter).

Final protein concentration was assessed spectrophotometrically at 280 nm using a Nanodrop One device (Thermo Fisher Scientific).

2.5) Characterization of Lysine-Conjugated Antibody-Drug Conjugates

The resulting conjugates were characterized as follows: Average Drug-Antibody-Ratio (DAR) Assessment by Native SEC-MS:

Before analysis, ADC was deglycosylated by adding 50 U of IgGZERO® (Genovis) enzyme for 50 μg of ADC. ADC was separated on an Agilent AdvanceBio SEC 200A 1.9 μm 2.1×150 mm PEEK column (cat #PL1980-3201PK) maintained at 30° C. The column was equilibrated in 50 mM ammonium acetate+10% (v/v) HPLC grade isopropanol. The flow rate was maintained at 0.075 mL/min during the run, and the ADC was typically eluted between 3.5 and 4.5 min. The flow and buffer composition were maintained following elution of the mAb or ADC. The column eluent was directed into a Bruker Impact II™ Q-TOF mass spectrometer scanning the 300-8000 m/z range ($ESI^+$). The source capillary voltage was set to 4500 V. The source drying gas and nebulizing gas were set at 8.0 L/min and 25 Psi, respectively. The source drying temperature was set at 200° C. ADC mass spectra were deconvoluted using Max- Ent algorithm included in the Bruker Compass® software, and the DAR was calculated using ion intensity peak height of each ADC sub-species.

Size Exclusion Chromatography (SEC):

SEC was performed on an Agilent 1100 HPLC system having an extra-column volume below 15 μL (equipped with short sections of 0.12 mm internal diameter peek tubing and a micro-volume UV flow cell). Column was an Agilent AdvanceBioSEC 300 Å 4.6×150 mm 2.7 μm (maintained at 30° C.). Mobile phase was 100 mM sodium phosphate and 200 mM sodium chloride (pH 6.8). 10% isopropanol (v/v) was added to the mobile phase to minimize secondary hydrophobic interactions with the stationary phase and prevent bacterial growth. Flow rate was 0.35 mL/min. UV detection was monitored at 280 nm or any other relevant wavelengths.

2.6) Overview of Synthesized Antibody-Drug Conjugates

TABLE 7

| Name of the conjugate | Drug-linker component | Antibody component | DAR | Deconvoluted mass spectrometry data | Monomeric purity (%) |
|---|---|---|---|---|---|
| T-GLC-EXA | LNK1 | Trastuzumab | 8 | Obs LC-1d: 25332 Da (Mass error 0 Da)<br>Obs HC-3d: 56274 Da (Mass error 1 Da) | 95%+ |
| T-VA-EXA | LNK3 | Trastuzumab | 8 | Obs LC-1d: 25323 Da (Mass error 0 Da)<br>Obs HC-3d: 56249 Da (Mass error 3 Da) | 95%+ |
| F-VA-EXA | LNK4-S | Farletuzumab | 8 | Obs LC-1d: 25713 Da (Mass error 1 Da)<br>Obs HC-3d: 56140 Da (Mass error 3 Da) | 95%+ |
| F-VA-EXA-4 | LNK4-S | Farletuzumab | 4.1 | Obs LC-0d: 23751 Da (Mass error 0 Da)<br>Obs LC-1d: 25712 Da (Mass error 0 Da)<br>Obs HC-0d: 50257 Da (Mass error 3 Da)<br>Obs HC-1d: 52218 Da (Mass error 2 Da)<br>Obs HC-2d: 54179 Da (Mass error 3 Da)<br>Obs HC-3d: 56141 Da (Mass error 4 Da) | 95%+ |
| F-LALA-VA-EXA | LNK4-S | Farletuzumab-LALA | 8 | Obs LC-1d: 25712 Da (Mass error 0 Da)<br>Obs HC-3d: 56054 Da (Mass error 1 Da) | 95%+ |
| F-LALA-VA-EXA-4 | LNK4-S | Farletuzumab-LALA | 4.2 | Obs LC-0d: 23751 Da (Mass error 0 Da)<br>Obs LC-1d: 25712 Da (Mass error 0 Da)<br>Obs HC-0d: 50173 Da (Mass error 2 Da)<br>Obs HC-1d: 52133 Da (Mass error 1 Da)<br>Obs HC-2d: 54094 Da (Mass error 2 Da)<br>Obs HC-3d: 56055 Da (Mass error 2 Da) | 95%+ |
| F-GLC-EXA | LNK2-S | Farletuzumab | 8 | Obs LC-1d: 25722 Da (Mass error 0 Da)<br>Obs HC-3d: 56167 Da (Mass error 2 Da) | 95%+ |
| M-SORAV | sulfo-SPDB-DM4 | Mirvetuximab | 3.35 | Native SEC-MS data:<br>DAR0 species: 146391 Da (2% Int.)<br>DAR1 species: 147351 Da (11% Int.)<br>DAR2 species: 148310 Da (22% Int.)<br>DAR3 species: 149270 Da (24% Int.)<br>DAR4 species: 150230 Da (19% Int.)<br>DAR5 species: 151191 Da (12% Int.)<br>DAR6 species: 152152 Da (9% Int.)<br>DAR7 species: 154084 Da (1% Int.) | 95%+ |
| F-SORAV | sulfo-SPDB-DM4 | Farletuzumab | 4.1 | Native SEC-MS data:<br>DAR1 species: 147745 Da (4% Int.)<br>DAR2 species: 148706 Da (10% Int.)<br>DAR3 species: 149667 Da (22% Int.)<br>DAR4 species: 150625 Da (27% Int.)<br>DAR5 species: 151586 Da (21% Int.)<br>DAR6 species: 152546 Da (10% Int.)<br>DAR7 species: 153507 Da (4% Int.)<br>DAR8 species: 154468 Da (2% Int.) | 95%+ |
| M-VA-EXA | LNK4-S | Mirvetuximab | 8 | Obs LC-1d: 25765 Da (Mass error 0 Da)<br>Obs HC-3d: 56259 Da (Mass error 3 Da) | 95%+ |
| NEG-VA-EXA | LNK4-S | Neg. control IgG Sino Bio. #HG1K | 8 | Obs LC-1d: 25371 Da (Mass error 1 Da)<br>Obs HC-3d: 55148 Da (Mass error 4 Da) | 95%+ |

LC-0d: light chain; LC-1d: light chain with 1 drug-linker; HC-0d: heavy chain; HC-1d: heavy chain with 1 drug-linker; HC-2d: heavy chain with 2 drug-linkers; HC-3d: heavy chain with 3 drug-linkers. Major glycoform is reported for HC.

Example 3: General Cell Culture Practices and Animal Experiments

Human cancer cell lines used in the present project were purchased from either the American Type Culture Collection (ATCC), The Leibniz Institute DSMZ German Collection of Microorganisms and Cell Cultures GmbH (DSMZ) or the European Collection of Authenticated Cell Cultures (ECACC). For use in experiments, cells were cultivated following good and established cell culture practices, following instructions from the original ATCC/DSMZ/ECACC supplier for cell culture media & supplement, cryopreservation, and subculturing procedures. Cells were incubated under a 5% $CO_2$ atmosphere at 37° C. for no longer than 2 months.

All animal procedures were performed in accordance with the European Union directive 86/609/EEC. Experiments were performed under individual permit and in animal care facilities accredited by the French Ministry of Agriculture. The study was approved by the local animal ethics committee (CECCAPP).

Example 4: Rodent Therapeutic Index Comparison of Glucuronide or Dipeptide Drug-Linker Designs Mice therapeutic index of drug-linker constructs LNK1 (glucuronide-exatecan) and LNK3 (dipeptide Val-Ala-Exatecan) were assessed, to compare mice therapeutic index of the two enzyme-cleavable modalities glucuronide and dipeptide Val-Ala. T-GLC-EXA ADC and T-VA-EXA ADCs were formulated, using model human HER2 targeting trastuzumab monoclonal antibody as targeting moiety. These ADCs were compared in terms of in vivo efficacy in a HER2+ gastric cancer model and in terms of tolerability (therapeutic index). As trastuzumab does not cross-react in mice, this assay gives useful information about apparent toxicity of the drug-linker component of the ADC (possible target-mediated toxicities are excluded).

Assessment of in vivo efficacy: NCI-N87 gastric cancer cells were implanted subcutaneously in female SCID mice (4 weeks old). ADCs were dosed once intravenously at a sub-curative dose of 1 mg/kg when tumors had grown to approximately 150 $mm^3$ (6 animals per group, assigned to minimize differences in initial tumor volumes between groups). Tumor volume was measured every 3-5 days by a caliper device and was calculated using the formula (L×W2)/2. Mice were sacrificed when the tumor volume exceeded 1000 $mm^3$.

Assessment of pharmacokinetic profile: PK profile (total Antibody-Drug Conjugate concentration based on mAb component over time) in rats following a single intravenous 3 mg/kg dose of conjugate. ADCs were injected at 3 mg/kg in female Sprague-Dawley rats (4-6 weeks old, Charles River) via the tail vein (three animals per group, randomly assigned). Blood was drawn into citrate tubes via retro-orbital bleeding at various time points, processed to plasma and stored at −80° C. until analysis. ADC concentration based on antibody component was assessed using a human IgG ELISA kit (Stemcell™ Technologies) according to manufacturer's protocol. Standard curves of corresponding monoclonal antibody were used for quantification. PK parameters (clearance, half-life and AUC) were calculated by two-compartmental analysis using Microsoft® Excel® software incorporating PK functions (add-in developed by Usansky et al., Department of Pharmacokinetics and Drug Metabolism, Allergan, Irvine, USA).

Assessment of in vivo tolerability: female SCID mice (n=3) were treated with a single intraperitoneal high dose of 200 mg/kg of ADC compound. Mice were observed for weight loss or apparent signs of toxicity over the course of 12 days. Enhertu® (trastuzumab deruxtecan) was used as a positive control in this experiment.

The results of this study are shown in FIG. 1. T-GLC-EXA and T-VA-EXA showed similar in vivo efficacy (FIG. 1A) and similar rat PK profile (FIG. 1B) but exhibited significant differences in mice tolerability at high doses (FIG. 1C). It was concluded that, at least for a use with the exatecan payload, the dipeptide Val-Ala cleavable modality provided a better efficacy/tolerability profile. As such, this entity was preferred for other ADC constructs.

Example 5: Flow Cytometry Assessment of Folate Receptor Alpha (FRa) Extracellular Binding Sites For FRa cell surface quantification, cells were incubated for 20 min at room temperature with PE anti-FOLR1 antibody (BioLegend cat #908304). Cell viability was assessed using a eBioscience™ Fixable Viability Dye eFluor™ 780 kit (Thermo Fisher Scientific cat #65-0865-18), following manufacturer's instructions. Analysis was performed using a BD Fortessa flow cytometer controlled by BD FACSDiva software (BD Biosciences) and data were analyzed using FlowJo software (BD Bioscience).

Figure 2:
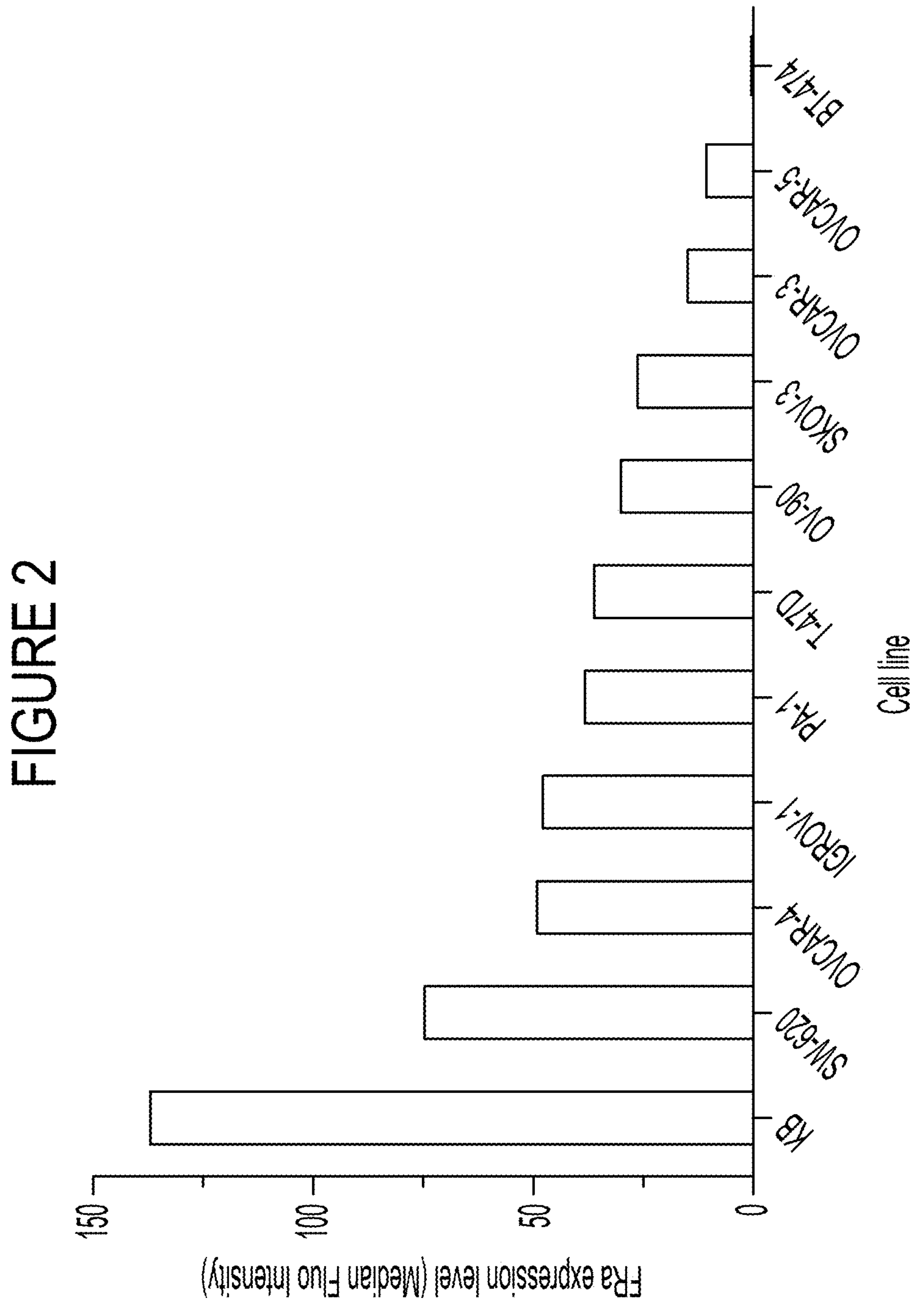
FIG. 2 represents flow cytometry assessment of folate receptor alpha extracellular expression, according to example 5.

The results are shown in FIG. 2. Cell lines of the present research program presented different levels of extracellular expression of FRa. BT-474 breast cancer cell did not express extracellular FRa, and was thus considered to be a negative control cell line in the context of the present research program.

Example 6: In Vitro Cytotoxicity Assay of Exatecan Mesylate on FRa+ Cancerous Cell Lines In vitro cytotoxicity of compound exatecan mesylate was assessed on several FRa positive cancerous cell lines. Cells were plated in 96-well plates at an appropriate density depending on the cell line (between 1000 and 10 000 cells/well in 100 μL of appropriate culture media) and incubated at 37° C. for 24 hours. Serial dilutions of the tested compound previously dissolved in culture media (50 μL) were added, and incubation was carried at 37° C. out for 144 hours. MTT (5 mg/mL, 20 μL, Sigma-Aldrich) was added into the wells, and incubation was continued for 1 to 2 hours at 37° C. Culture media was then carefully removed, and well content was homogeneously dissolved with acidified isopropanol. Absorbance values were measured on a Multiskan™ Sky microplate reader (Thermo Scientific) using a wavelength of 570 nm (with a reference wavelength of 690 nm). The IC50 concentration values compared to untreated control cells were determined using inhibition dose response curve fitting (GraphPad Prism 9).

Figure 3:
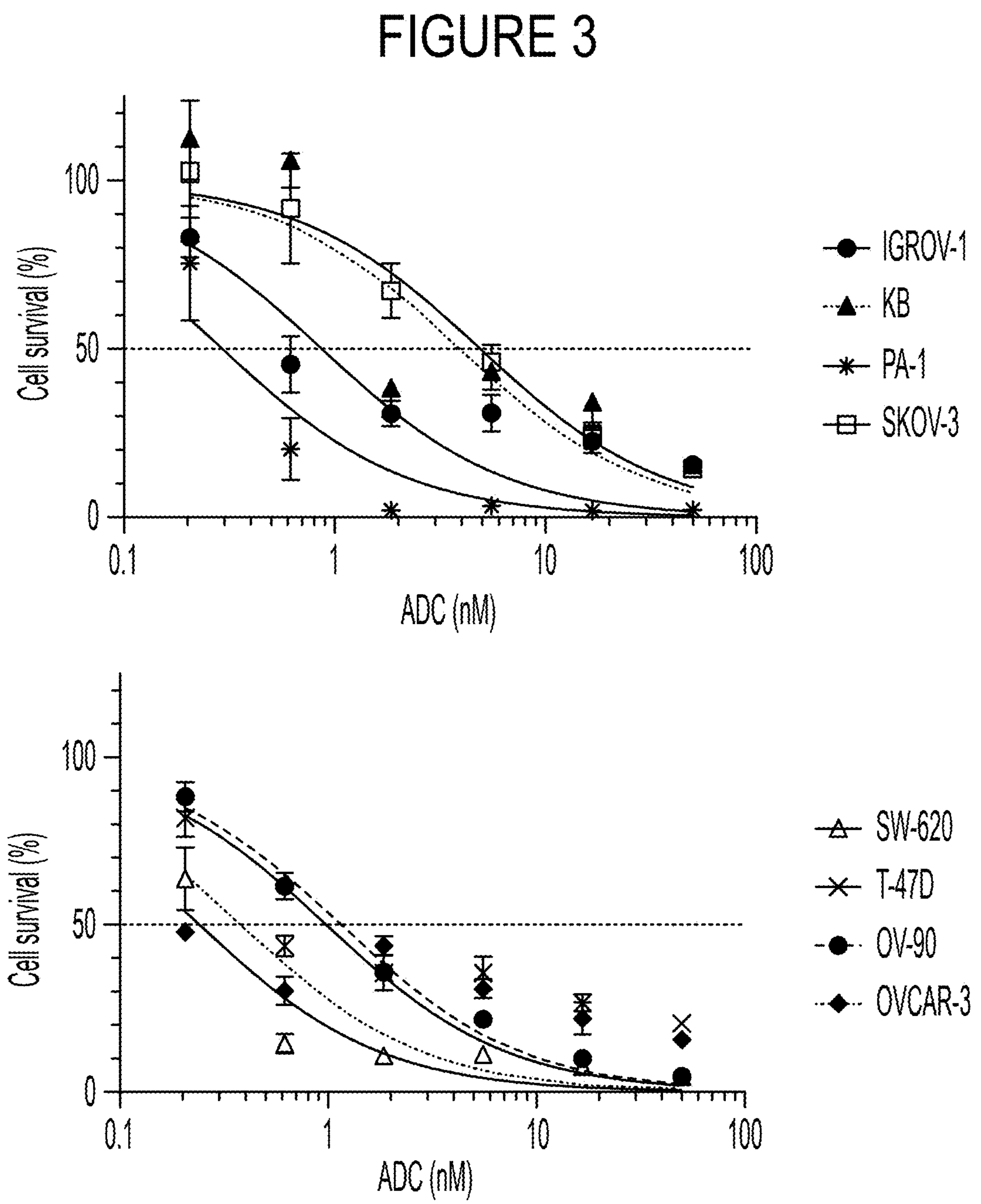
FIG. 3 represents in vitro cytotoxicity data of compound exatecan mesylate on several folate receptor alpha positive cancerous cell lines, according to example 6.

The results are shown in FIG. 3. Exatecan Mesylate exhibited sub-nM to low-nM IC50's in vitro potencies, prompting us to investigate the use of this compound as an ADC payload for FRa-expressing malignancies.

Example 7: Recombinant FRα-Binding Affinity by ELISA

Sandwich ELISA assays were performed using 96-well high-binding ELISA plates (Corning Inc., New York, NY, USA, Cat #3590). Plates were coated using 100 μL/well of recombinant human FRa protein (Sino Biological cat #11241-H08H); recombinant cynomolgus FRa protein (Sino Biological cat #90950-C08H); recombinant rat FRa protein (Sino Biological cat #81073-R08H) or recombinant mouse FRa protein (Sino Biological cat #50573-M08H) in PBS (pH 7.4) at 2 μg/mL and incubated overnight at 4° C. After 2 washes with PBS-T (PBS+0.05% Tween-20), the plates were blocked with 200 μL/well of incubation buffer (PBS-T+0.1% BSA) for 1 h at room temperature. The plates were washed 4 times with PBS-T, and 100 μL of a threefold dilution series of tested compound (antibody or antibody-drug conjugate) was added. Then, the plates were incubated for 2 h at room temperature in the dark. After 5 washes with PBS-T, plates were incubated 1 h at room temperature with 100 μL/well of a goat anti-human IgG (H+L) HRP conjugated antibody (Jackson Immunoresearch cat #109-035-088), previously diluted 1:250 000 in incubation buffer. After 5 washes with PBS-T, TMB substrate solution (Thermo-Fisher cat #N301) was added. Peroxidase activity was stopped with 0.18M $H_2SO_4$ and absorbance was read at 450 nm (reference wavelength 650 nm) using a Thermo Scientific MultiSkan EX microplate reader. Sigmoidal fittings were performed using GraphPad Prism 9 software.

The results are shown in FIG. 4. FIG. 4A: all antibodies and ADCs exhibited similar recombinant human FRα binding affinity of approximately EC50=0.1 nM. No loss of binding was observed between native antibody and respective ADC construct. No loss of binding was observed between farletuzumab and farletuzumab-LALA and their respective ADC constructs. No significant loss of binding was observed between mirvetuximab and M-SORAV ADC construct. No human FRα binding was detected for negative control ADC NEG-VA-EXA. FIG. 4B: F-LALA-VA-EXA binds equally to human and cynomolgus recombinant FRa protein and does not bind to rat and mouse recombinant FRa protein. As such, F-LALA-VA-EXA is not rodent cross-reactive but is cynomolgus cross-reactive.

Example 8: Human FRα-Binding Affinity by SPR

Surface plasmon resonance (SPR) experiments were performed on a Biacore T200 apparatus, at 25° C. Tested antibody or ADC were captured at low density (300-500 RU) on a CM5 series S sensorchip, beforehand functionalized with a Human Antibody Capture kit (Cytiva cat #BR100839). A functionalized surface/flow cell treated similarly but omitting ligand was used as reference. To measure kinetics rates and affinities, recombinant human FRa (Sino Biological cat #11241-H08H) analyte sample has been injected in duplicates at 5 concentrations (0.5, 1, 2, 4, 8 nM) in series using single cycle kinetics strategy and at constant 70 μL/mL flow rate of running buffer (HBS-EP+, Cytiva cat #BR100669) with contact pulses of 300 sec. The dissociation phase was measured by injection of running buffer for 900 sec. Between duplicates, surfaces/flow cells were regenerated with 3M MgCl2 to remove both analyte and ligand, and fresh ligand capture were done using identical conditions. The data analysis was performed using the Biacore Evaluation software after subtraction of reference surface and analyte zero-concentration signals. Data were processed and fit to a 1:1 binding model to determine the binding kinetic rate constants, $k_a$ (on-rate) and $k_d$ (off-rate), and the $K_D$ (equilibrium dissociation constant, also referred to as "affinity"). Mean values and standard deviations over replicates are reported.

The results are shown in FIG. 5. No loss of recombinant human FRa binding was observed between native antibody and respective ADC construct. No loss of binding was observed between farletuzumab and farletuzumab-LALA and respective ADC constructs. Surprisingly, a ~10-fold reduced $K_D$ value (affinity constant) was observed for farletuzumab and farletuzumab-LALA-based constructs compared to mirvetuximab and mirvetuximab-based constructs. This was a consequence of an increased $k_d$ value (dissociation rate constant) for farletuzumab and farletuzumab-LALA-based constructs compared to mirvetuximab and mirvetuximab-based constructs (considering that association rate constant $k_a$ was similar). No human FRa binding events were detected for negative control IgG1 (Sino Biologicals cat #HG1K).

Example 9: Cell-Binding Affinity by Flow Cytometry

Antibody or ADC binding to extracellular human FRa expressed on cancerous cell lines was assessed by flow cytometry. Tested antibody or ADC was conjugated to APC fluorophore using LYNX Rapid APC Antibody Conjugation Kit according to the manufacturer's protocol (Bio-Rad, Cat #LNK032APC). Into 500 000 cells (suspended in 100 μL of PBS in flow cytometry plastic tubes) was added 5 μL of a 10 μg/mL solution of tested APC-labelled antibody or ADC. Cells were incubated 20 min in the dark, were washed with PBS 3 times by centrifugation and were re-suspended in 200 μL of PBS for analysis. Flow cytometry was performed using a BD Fortessa flow cytometer controlled by BD FACSDiva software (BD Biosciences) and data were analyzed using FlowJo software (BD Bioscience).

The results are shown in FIG. 6. Comparable human FRα cell binding was observed between farletuzumab and farletuzumab-LALA and respective ADC constructs. Native mirvetuximab and native farletuzumab binding affinity appeared identical. Surprisingly significant loss of binding was observed for ADC derivative of mirvetuximab (M-SORAV), compared to its parent antibody mirvetuximab. This could be explained by either (1) heterogeneous stochastic conjugation of sulfo-SPDB-DM4 drug-linker that could react with lysine aminoacids that are part of the antibody variable region, thus decreasing binding affinity; (2) a lower APC labelling efficiency of M-SORAV, as LYNX Rapid APC conjugation kit reacts with lysine aminoacids like sulfo-SPDB-DM4 or (3) a combination of (1) and (2). No binding was observed on FRa-negative control cell line BT-474 for all tested compounds.

Example 10: Ex-Vivo ADC Human Plasma Stability

F-VA-EXA and F-LALA-VA-EXA ADC samples (>6 mg/mL solutions in PBS) were diluted with pure sterile Human plasma (GeneTex Cat #GTX73265) in centrifuge tubes with screw cap to yield a final ADC concentration of 200 μg/mL (residual PBS volume below 5% v/v). Samples were incubated at 37° C. and aliquots were taken at time points of 5 min, 6 hours, 1 day, 2 days, 3 days, and 7 days (aliquots were kept frozen at −80° C. until analysis). ADCs were isolated from plasma by immunocapture using Dynabeads™ M-280 Streptavidin (Thermo Scientific) magnetic beads, previously coated with biotinylated human folate receptor alpha recombinant protein (Sino Biologicals cat #11241-H08H). Briefly, 600 μL of commercial bead solution were washed twice with HBS-EP buffer (Cytiva, catalog #BR100188) and re-suspended in 1.2 mL of HBS-EP buffer. 65 μL (48 μg protein amount) of biotinylated recombinant FRa solution was added and solution was agitated for 2 hours at room temperature. Beads were then washed 3 times with HBS-EP buffer and re-suspended in 1.2 mL of HBS-EP buffer. For one immunocapture, 100 μL of previous bead solution was added onto 100 μL of HBS-EP in a microcentrifuge tube. 10 μL of ADC solution in plasma (theoretical 2 μg ADC amount) was added and solution was agitated 2 hours at room temperature. After incubation, the beads-ADC complex was washed twice with HBS-EP buffer, resuspended with 200 μL of HBS-EP buffer and deglycosylated by adding 2 μL/1000 U of PNGase F (New England Biolabs cat #P0705L) overnight at 37° C. with gentle agitation. Beads were then washed twice with HBS-EP buffer, twice with distilled water and once with 10% acetonitrile in water (v/v). The beads were incubated for 30 min with gentle agitation at room temp with 50 μL of a 30% acetonitrile in water (v/v) containing 0.1% (v/v) of formic acid. The eluted samples containing the deglycosylated ADC were then analyzed by denaturing reversed phase chromatography-mass spectrometry using a Thermo UltiMate 3000 UHPLC system equipped with a Bruker Impact II™ Q-TOF mass spectrometer. Mobile phase A was water+0.1% formic acid and mobile phase B was acetonitrile+0.1% formic acid.

Column was an Agilent PEEK PLRP-S 1000 Å 2.1×100 mm 5 μm (80° C.). Linear gradient was 20% B to 50% B in 25 min. Flow rate was 0.4 mL/min. UV detection was monitored at 280 nm. The Q-ToF mass spectrometer was used in the m/z range 500-5000 ($ESI^+$). Data were deconvoluted using the MaxEnt algorithm included in the Bruker Compass® software. For stability data analysis, the deconvolution of the raw spectrum within selected light-chain (LC) and heavy-chain (HC) elution time windows was implemented. The drug-linker loss or modifications were identified according to the corresponding mass shifts from the starting ADC material. The relative ratios of ADC with different DAR were calculated by dividing the intensity of the specific ADC sub-species with the intensity from the total ADC species. Final DAR value was calculated as described in Xu et al., Anal. Biochem., 2011, 412 (1), 56-66.

Figure 7:
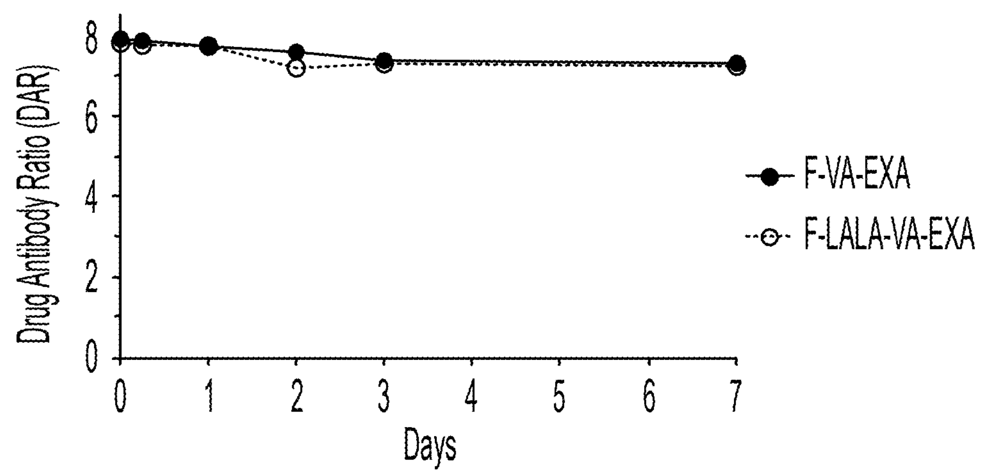
FIG. 7 represents ex-vivo human plasma stability of conjugates, according to example 10.

The results are shown in FIG. 7. >90% drug-linker human plasma stability was observed for both F-VA-EXA and F-LALA-VA-EXA ADCs. No drug-linker mass shift was observed during this study (no premature exatecan release or metabolization), excepted the +18 Da (+$H_2O$) mass shift from self-stabilizing hydrolysis of the maleimide group (which was complete after 48-72 h ADC incubation time). Only observed instability was caused by retro-michael maleimide deconjugation of the entire drug-linker on the heavy chain of the ADC (no deconjugation was observed on the light chain).

Example 11: In Vitro Cytotoxicity Experiments on FRa Negative Cell Line

To assess unspecific (off-target) cytotoxicity of ADCs, in vitro cytotoxicity assays were realized in BT-474 (FRa negative) cancer cell line. Cells were plated in 96-well plates at an appropriate density depending on the cell line (between 1000 and 10 000 cells/well in 100 μL of appropriate culture media) and incubated at 37° C. for 24 hours. Serial dilutions of the tested compound previously dissolved in culture media (50 μL) were added, and incubation was carried at 37° C. out for 144 hours. MTT (5 mg/mL, 20 μL, Sigma-Aldrich) was added into the wells, and incubation was continued for 1 to 2 hours at 37° C. Culture media was then carefully removed, and well content was homogeneously dissolved with acidified isopropanol. Absorbance values were measured on a Multiskan™ Sky microplate reader (Thermo Scientific) using a wavelength of 570 nm (with a reference wavelength of 690 nm). The IC50 concentration values compared to untreated control cells were determined using inhibition dose response curve fitting (GraphPad Prism 9).

Figure 8:
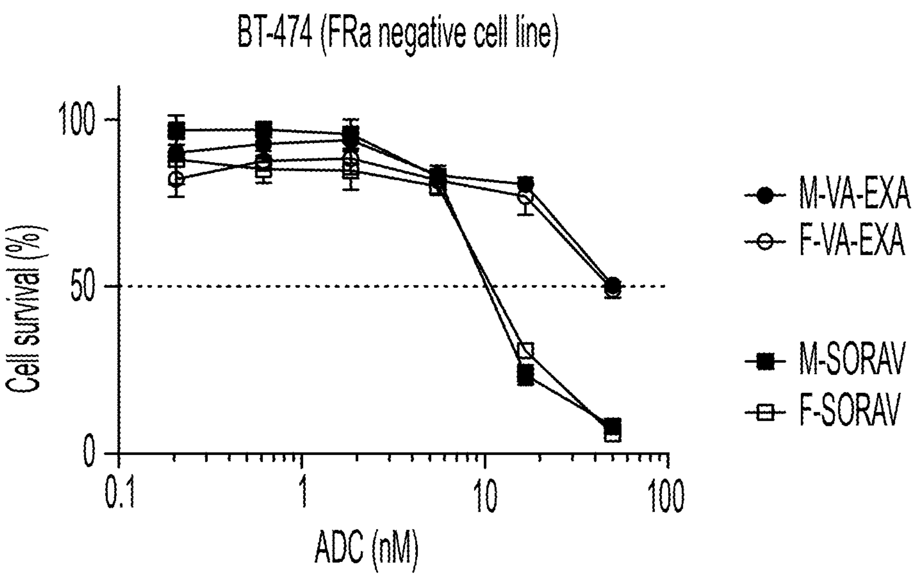
FIG. 8 represents in vitro cytotoxicity assay of conjugates on a folate receptor alpha negative breast cancer cell line BT-474, according to example 11.

The results are shown in FIG. 8. Soravtansine (sulfo-SPDB-DM4)-based ADCs exhibited a higher level of off-target (non-FRa-mediated) cell killing potencies compared to VA-EXA (LNK4-S drug-linker)-based ADCs. This has been observed for both mirvetuximab- and farletuzumab-based ADCs. VA-EXA drug-linker component yields less off-target toxicity compared to soravtansine drug-linker, which is a good prerequisite to increase the tolerability of the ADC in a clinical setup.

TABLE 8

| ADC | Drug-linker component | Off-target toxicity in a BT-474 FRa negative breast cancer model |
|---|---|---|
| M-VA-EXA | LNK4-S | + |
| F-VA-EXA | LNK4-S | + |
| M-SORAV | Sulfo-SPDB-DM4 | +++ |
| F-SORAV | Sulfo-SPDB-DM4 | +++ |

Example 12: In Vivo Efficacy Xenograft Models

Four to five-week-old female CB-17 severe combined immunodeficient (SCID) mice were obtained from Janvier labs (Le Genest-Saint-Isle, France) and quarantined for 7 days prior to study initiation. Mice were inoculated subcutaneously with cells (5-10×$10^6$ cells per mouse) resuspended in PBS (OV-90, SW-620, KB, BT-474 cell lines) or 50% BD Matrigel (Corning®) in PBS (PA-1, IGROV-1, OVCAR-3, NCI-H2110 cell lines). When average tumor volume reached about 120-150 $mm^3$ mice were randomized (typically 7 mice per group) and treated by a single (unless stated otherwise) intravenous injection of PBS (negative control) or investigated antibody-drug conjugate. Tumor volumes were measured every 3-5 days using a caliper device (length×width) and calculated using the following formula $V=4/3\times TT\times R_3$, where R represents the radius. Mice were sacrificed when the tumor volume exceeded 1500 mm3 or in case of ulceration of the tumor.

In the IGROV-1 tumor model, a tumor reimplantation challenge was performed at day 94 of the study. Mice treated with F-LALA-VA-EXA (12 mg/kg IV once) were re-implanted with IGROV-1 cells using the same procedure that was used at the beginning of the study (other flank for the animals). A control group of 5 new SCID animals were also re-implanted following the exact same procedure.

Figure 9:
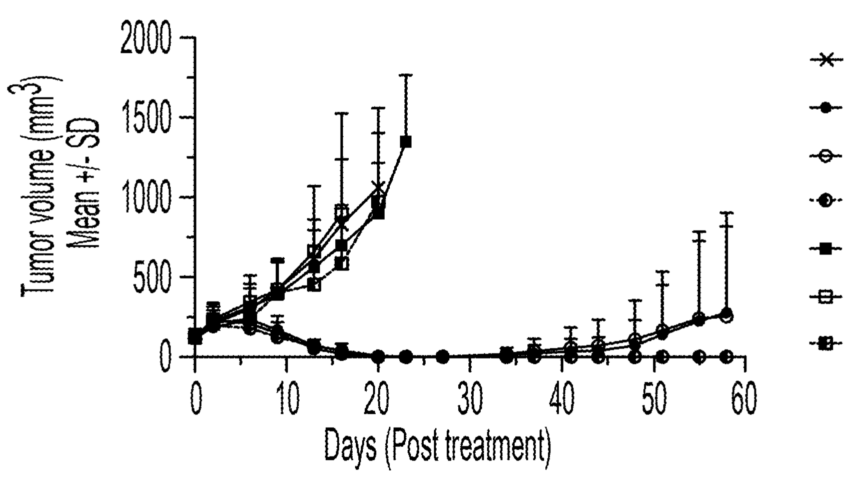
FIG. 9 represents in vivo efficacy assessment of conjugates in a folate receptor alpha positive SW-620 xenograft cancer model, according to example 12.

In FIG. 9 is presented a tumor xenograft experiment in the SW-620 cancer model. F-VA-EXA and M-SORAV conjugates were injected IV once at 5, 10 or 15 mg/kg. F-VA-EXA was highly active at a dose of 5 mg/kg and above, whereas comparator M-SORAV was inactive even when dosed at 15 mg/kg.

Figure 10:
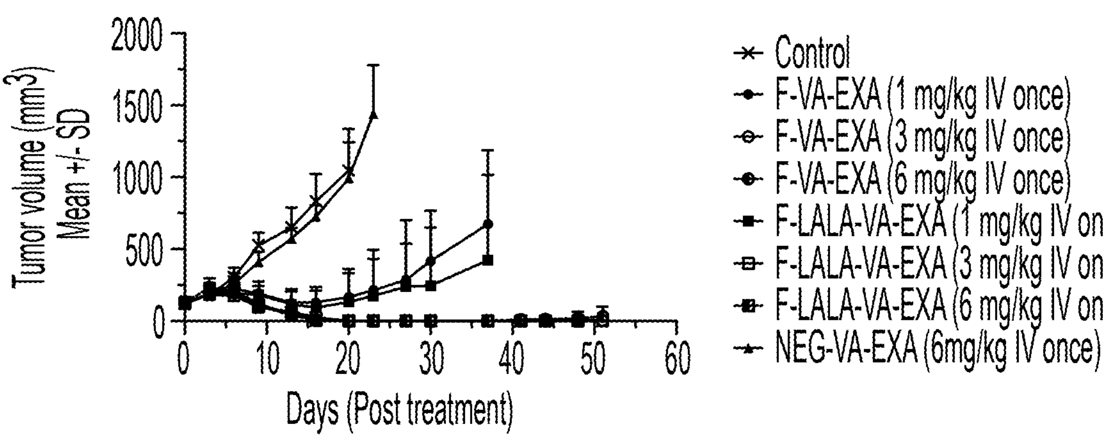
FIG. 10 represents in vivo efficacy assessment of conjugates in a second folate receptor alpha positive SW-620 xenograft cancer model, according to example 12.

In FIG. 10 is presented a tumor xenograft experiment in the SW-620 cancer model. F-VA-EXA and F-LALA-VA-EXA were injected IV once at 1, 3 and 6 mg/kg. Non-targeting isotype-matched negative control ADC NEG-VA-EXA was injected IV once at 6 mg/kg. F-VA-EXA and F-LALA-VA-EXA were equally highly active at a dose of 1 mg/kg and above. Non-targeting conjugate NEG-VA-EXA was inactive at the highest tested dose of 6 mg/kg, demonstrating that antitumor activity of conjugates is target-selective.

Figure 11:
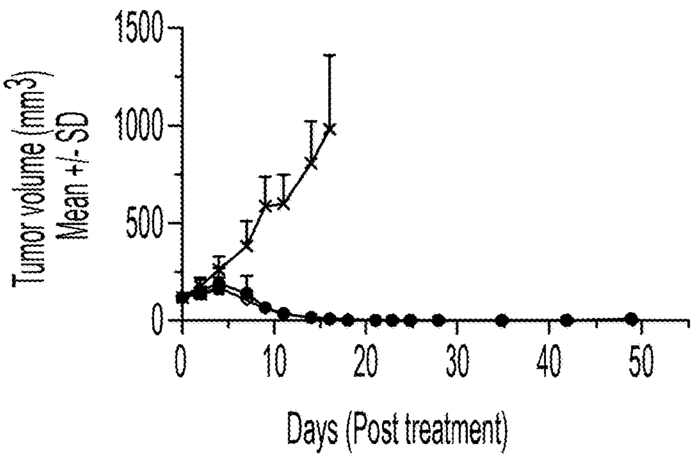
FIG. 11 represents in vivo efficacy assessment of conjugates in a folate receptor alpha positive OV-90 xenograft cancer model, according to example 12.

In FIG. 11 is presented a tumor xenograft experiment in the OV-90 cancer model. F-VA-EXA, F-LALA-VA-EXA and M-SORAV conjugates were injected IV once at 30 mg/kg. All conjugates were highly active, with 100% remission rate in all groups. However, significant toxicities were observed with the M-SORAV conjugate: 6 out of 6 mice showed unkempt appearances (dull and matted haircoat), 3 out of 6 mice presented signs of prostration and 2 out of 6 mice had diarrhea. No toxicities were observed with F-VA-EXA and F-LALA-VA-EXA conjugates. These data suggest better preclinical therapeutic window for the F-VA-EXA and F-LALA-VA-EXA constructs compared to M-SORAV.

Figure 12:
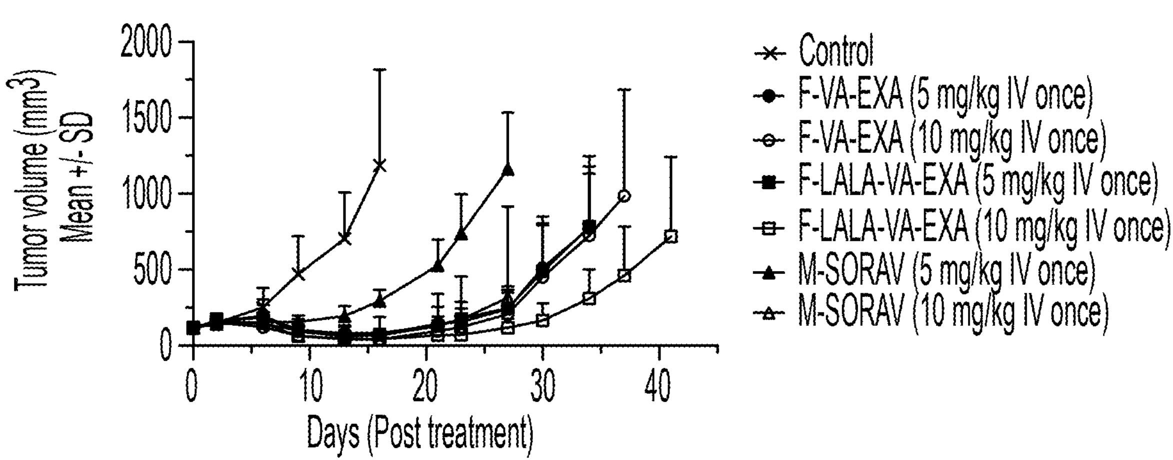
FIG. 12 represents in vivo efficacy assessment of conjugates in a second folate receptor alpha positive OV-90 xenograft cancer model, according to example 12.

In FIG. 12 is presented a tumor xenograft experiment in the OV-90 cancer model. F-VA-EXA, F-LALA-VA-EXA and M-SORAV conjugates were injected IV once at sub-curative 5 and 10 mg/kg dose. At 5 mg/kg, F-VA-EXA and F-LALA-VA-EXA showed similar efficacy and improved efficacy when compared to M-SORAV. At 10 mg/kg, F-VA-EXA and M-SORAV showed similar efficacy (although more heterogeneity was observed within the M-SORAV group). At 10 mg/kg, F-LALA-VA-EXA outperformed both F-VA-EXA and M-SORAV.

Figure 13:
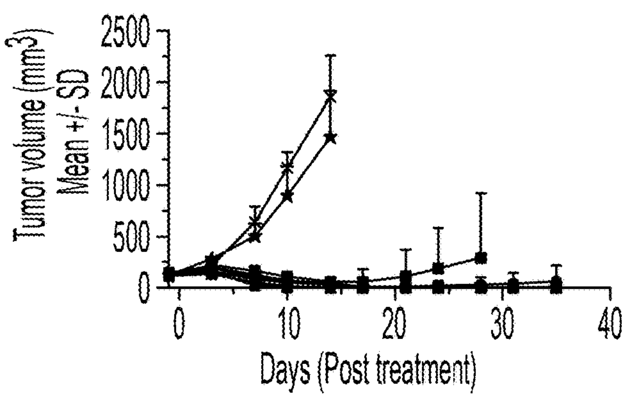
FIG. 13 represents in vivo efficacy assessment of conjugates in a folate receptor alpha positive KB xenograft cancer model, according to example 12.

In FIG. 13 is presented a tumor xenograft experiment in the KB cancer model. F-VA-EXA, F-LALA-VA-EXA and M-SORAV conjugates were injected IV once at 3, 6 and 12 mg/kg. Non-targeting isotype-matched negative control ADC NEG-VA-EXA was injected IV once at 12 mg/kg. F-VA-EXA, F-LALA-VA-EXA and M-SORAV were equally active at a dose of 3 mg/kg and above. Non-targeting conjugate NEG-VA-EXA was inactive at the highest tested dose of 12 mg/kg, demonstrating that antitumor activity of conjugates is target-selective.

Figure 14:
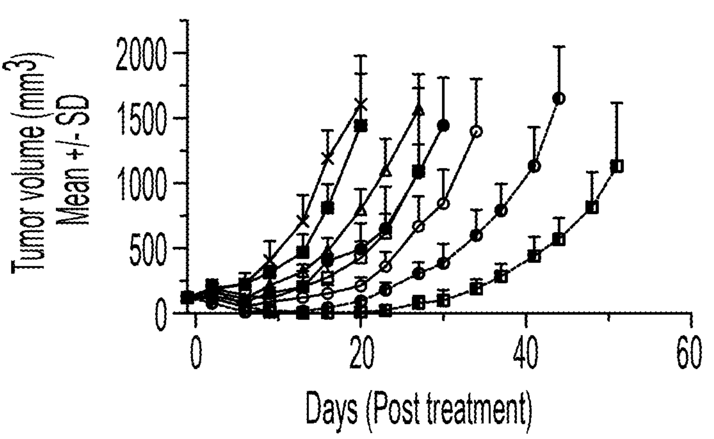
FIG. 14 represents in vivo efficacy assessment of conjugates in a folate receptor alpha positive PA-1 xenograft cancer model, according to example 12.

In FIG. 14 is presented a tumor xenograft experiment in the PA-1 cancer model. F-LALA-VA-EXA and M-SORAV conjugates were injected IV once at sub-curative 3, 6 and 12 mg/kg dose. Non-targeting isotype-matched negative control ADC NEG-VA-EXA was injected IV once at 12 mg/kg. At 3 mg/kg, F-LALA-VA-EXA outperformed M-SORAV. At 6 mg F-LALA-VA-EXA slightly outperformed M-SORAV. At 12 mg M-SORAV outperformed F-LALA-VA-EXA. Overall, both conjugates exhibited a similar level of efficacy. At the highest tested dose of 12 mg/kg, the non-targeting conjugate NEG-VA-EXA exhibited a slightly decreased tumor growth rate compared to the untreated control group.

Figure 15:
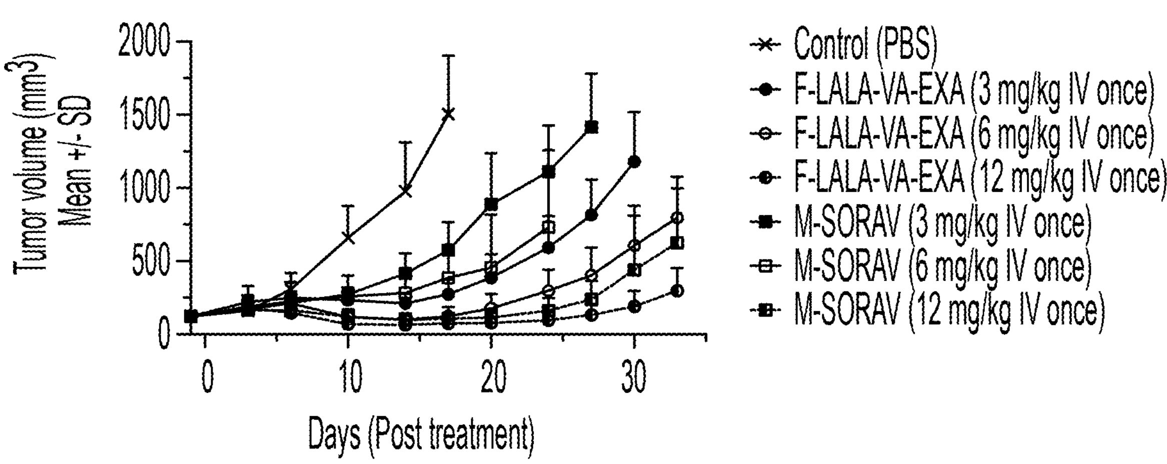
FIG. 15 represents in vivo efficacy assessment of conjugates in a third folate receptor alpha positive OV-90 xenograft cancer model, according to example 12.

In FIG. 15 is presented a tumor xenograft experiment in the OV-90 cancer model. F-LALA-VA-EXA and M-SORAV conjugates were injected IV once at 3, 6 and 12 mg/kg dose. At 3, 6 and 12 mg/kg, F-LALA-VA-EXA outperformed M-SORAV.

Figure 16:
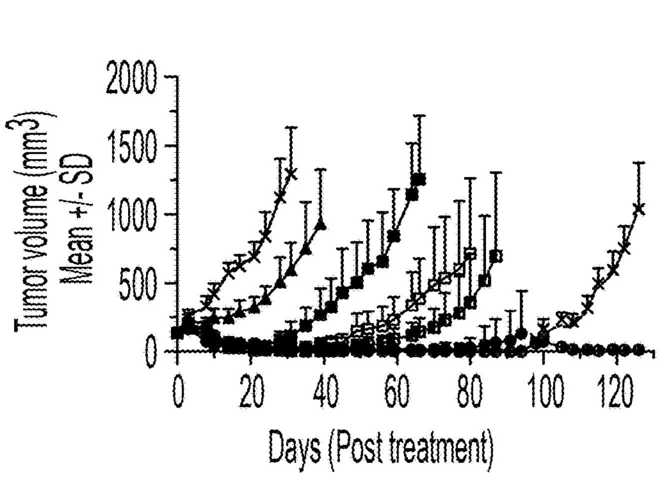
FIG. 16 represents in vivo efficacy assessment and tumor re-implantation challenge of conjugates in a folate receptor alpha positive IGROV-1 xenograft cancer model, according to example 12.

In FIG. 16 is presented a tumor xenograft experiment in the IGROV-1 cancer model. F-LALA-VA-EXA and M-SORAV conjugates were injected IV once at 3, 6 and 12 mg/kg dose. Non-targeting isotype-matched negative control ADC NEG-VA-EXA was injected IV once at 12 mg/kg. At 3, 6 and 12 mg/kg, F-LALA-VA-EXA and M-SORAV showed similar level of efficacy, with strong tumor regression. At the highest tested dose of 12 mg/kg, the non-targeting conjugate NEG-VA-EXA exhibited some level of efficacy, albeit less pronounced than other FRa-targeting ADCs of the study. The tumor regrowth rechallenge performed after day 94 of the study confirmed that F-LALA-VA-EXA is able to induce a protective immunologic memory response, as no tumor growth was observed after re-implantation of the groups treated with F-LALA-VA-EXA at 12 mg/kg IV once (a positive control group with new untreated SCID mice showed tumor growth after implantation).

Figure 17:
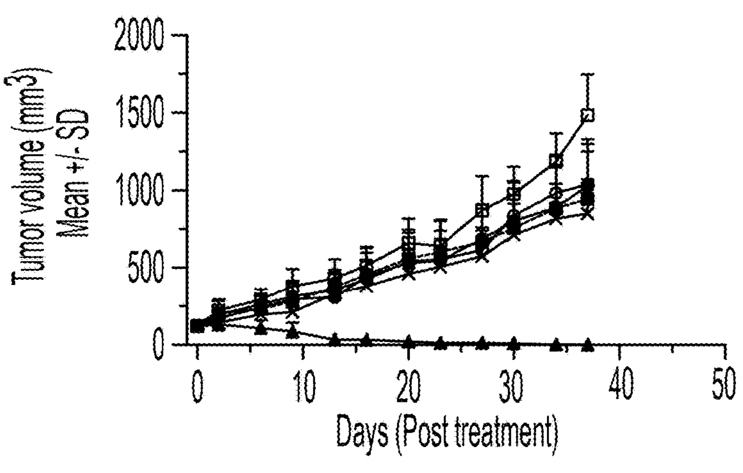
FIG. 17 represents in vivo efficacy assessment of conjugates in a folate receptor alpha negative BT-474 xenograft breast cancer model, according to example 12.

In FIG. 17 is presented a tumor xenograft experiment in the folate receptor alpha negative (FRa neg) BT-474 breast cancer model. F-LALA-VA-EXA and M-SORAV conjugates were injected IV once at 5 and 10 mg/kg dose. Enhertu® (HER2-targeting trastuzumab deruxtecan) was used as a positive control and was injected IV once at 10 mg/kg dose. No efficacy was observed for F-LALA-VA-EXA and M-SORAV at both doses, confirming that the efficacy of these conjugates is FRa selective. As expected and as observed before (Conilh et al., 2021, Pharmaceuticals, 14 (3), 247, doi: 10.3390/ph14030247), Enhertu® was efficacious in this HER2 positive BT-474 cancer model.

TABLE 9

| ADC | In vivo efficacy in SW-620 cancer model | In vivo efficacy in OV-90 cancer model | In vivo efficacy in KB cancer model | In vivo efficacy in PA-1 cancer model | In vivo efficacy in IGROV-1 cancer model | In vivo efficacy in BT-474 cancer model (FRa neg) |
|---|---|---|---|---|---|---|
| F-VA-EXA | +++ | ++ | +++ | ++ | +++ | − |
| F-LALA-VA-EXA | +++ | +++ | +++ | ++ | +++ | − |
| M-SORAV | − | ++ | +++ | ++ | +++ | − |

Example 13: Mice Tolerability Experiment

To assess mice preclinical therapeutic index, mouse tolerability experiments were performed with F-VA-EXA, F-LALA-VA-EXA and M-SORAV conjugates. Female SCID mice (n=5 mice per group) were treated with a single intraperitoneal dose of F-VA-EXA (200 mg/kg), F-LALA-VA-EXA (200 mg/kg) or M-SORAV (100 mg/kg). Mice were carefully monitored for weight loss or apparent signs of toxicity over the course of 21 days.

The same experiment was also performed in female CD-1 mice, treated with either 0, 50, 100, 150 or 200 mg/kg IV once of F-LALA-VA-EXA.

Figure 18:
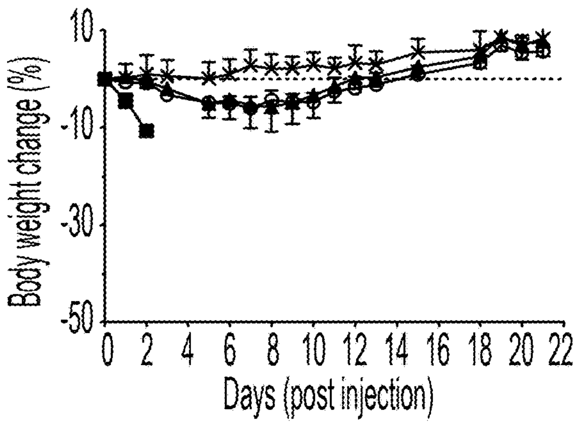
FIG. 18 represents in vivo SCID and CD-1 mice tolerability assessment of conjugates at high doses, according to example 13.

The results are shown below and in FIG. 18 (for the SCID mice experiment). F-VA-EXA and F-LALA-VA-EXA were well tolerated with no apparent signs of toxicity at a dose of 200 mg/kg. On the contrary, all mice treated with M-SORAV at a dose of 100 m/kg exhibited significant signs of toxicity (unkempt appearance with fuzzy fur, diarrhea, prostration, closed eyes, subdued behavior) and were found dead or had to be euthanized at day 2-3. These results, alongside above-mentioned xenograft efficacy data, show the superior preclinical therapeutic index of the F-VA-EXA and F-LALA-VA-EXA constructs, compared to comparator M-SORAV.

In female CD-1 mice, MBK-103 did not cause any dose dependent adverse systemic or local effects at every dose levels investigated (up to 200 mg/kg IV once). No weight loss or change in behavior were observed. The only notable observation was a slight decrease in the weight of the thymus and spleen in all groups compared to the control group during the final necropsy.

TABLE 10

| ADC | Effective dose (ED) range based on in vivo xenografts experiments (SCID mice) | Maximum Tolerated Dose in SCID mice (MTD) | Preclinical rodenttherapeutic index (MTD divided by ED) |
|---|---|---|---|
| F-VA-EXA | 1-10 mg/kg | Above 200 mg/kg | 40-200 |
| F-LALA-VA-EXA | 1-10 mg/kg | Above 200 mg/kg | 40-200 |
| M-SORAV | 1-10 mg/kg | Below 100 mg/kg | 10-100 |

Example 14: Sprague-Dawley Rat Pharmacokinetic Study

F-VA-EXA and F-LALA-VA-EXA conjugates were injected at 5 mg/kg in female Sprague-Dawley rats (4-6 weeks old-Charles River) via the tail vein (6 animals per group, randomly assigned). Blood was drawn into citrate tubes via retro-orbital bleeding at 5 min, 4 h, 1 day, 2 days, 4 days, 7 days, 14 days, and 21 days; processed to plasma; and stored at −80° C. until analysis.

Total mAb concentration was assessed by ELISA, using a goat polyclonal anti-human IgG (H+L) primary antibody (Jackson Immunoresearch) as capture reagent and a mouse polyclonal anti-human IgG (H+L) HRP conjugate (Jackson Immunoresearch) as secondary detection antibody. Total ADC concentration was assessed by ELISA, using a rabbit polyclonal anti-exatecan antibody (ref #6294/00000920, custom-made at Biotem, Apprieu, France) as capture reagent, and a mouse polyclonal anti-human IgG (H+L) HRP conjugate (Jackson Immunoresearch) as secondary detection antibody. Standard curves of ADC were used for quantification.

Pharmacokinetic parameters (clearance, half-life, Vss and AUC) were calculated by two-compartmental analysis using Microsoft Excel software incorporating PK functions (add-in developed by Usansky et al., Department of Pharmacokinetics and Drug Metabolism, Allergan, Irvine, CA, USA).

Free exatecan concentration was assessed using a LC/MS-MS method, using an Agilent 1100 HPLC system and a Sciex API 4000 MS/MS system. Rat plasma samples were protein-precipitated using an organic solution composed of 80:20 (v/v) acetonitrile/methanol+1% formic acid+d5-exatecan (20 ng/ml) as internal standard. Samples were analyzed using gradient elution mode onto a Phenomenex Kinetex® C8 2.1×30 mm 2.6 μm 100A column maintained at 45° C. (Phenomenex cat #00D-4497-AN). Mobile phase A was water+0.15% formic acid and mobile phase B was acetonitrile/isopropanol 80:20 (v/v)+0.15% formic acid. Flow rate was 0.8 mL/min. For detection, MRM scanning was used in the positive ion mode. The calibration curve was plotted using peak area ratios analyte/deuterated internal standard versus nominal analyte concentration, using linear least squares regression employing 1/x weighting. Calibration curve ranged from 0.2 (LLOQ) to 500 ng/mL.

Figure 19:
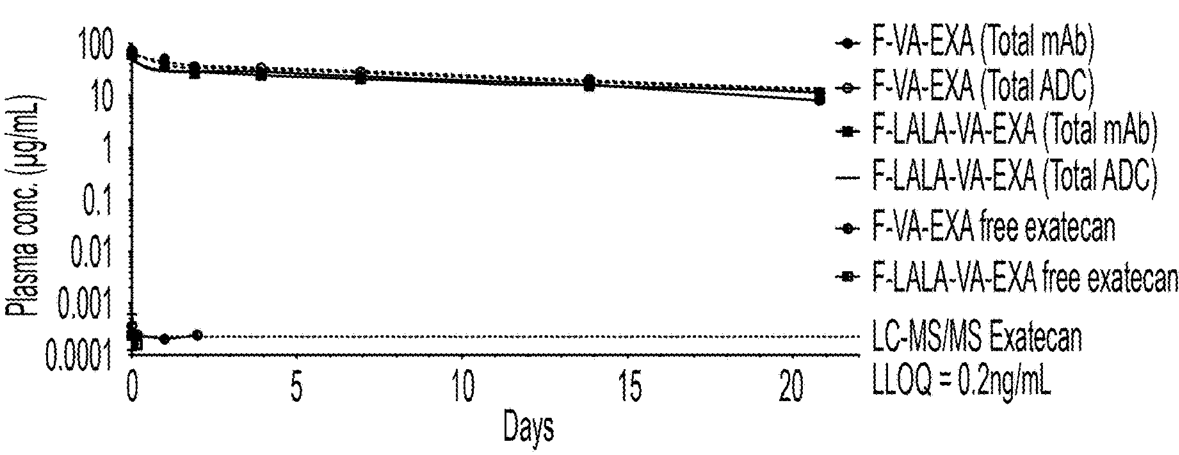
FIG. 19 represents in vivo rat pharmacokinetic assessment of total mAb, total ADC and free exatecan subcomponents of conjugates, according to example 14.

The results are shown in FIG. 19. F-VA-EXA and F-LALA-VA-EXA exhibited a biphasic PK profile in circulation (fast distribution phase followed by a slower elimination phase), with similar distribution volumes, slow clearance rates and half-life in the 13-15 days range. Total mAb and total ADC curves were similar in intensity, slope, and shape, suggesting good ADC stability (no major payload deconjugation over time). Free exatecan payload was only detected during the 0-48 h period of the experiment ($10^6$ times less concentrated than the parent ADC component), suggesting good ADC stability and no premature deconjugation of exatecan.

Example 15: Pulmonary Inflammatory and Toxicity Evaluation in Mice

Bleomycin has been widely used in rodents to model pulmonary fibrosis for the study of mechanisms involved in fibrogenesis and for evaluation of potential therapies. To assess ADC pulmonary toxicity, bleomycin-induced pulmonary fibrosis was induced in mice following known procedures as described by Walter and Kleeberger, Mouse Models of Bleomycin-Induced Pulmonary Fibrosis, 2008, Curr. Protoc. Pharmacol. 40:5.46.1-5.46.17. At day 0, 4 and 8, female C57/BL6 mice (Janvier Labs, Le Genest-Saint-Isle, France) were lightly anesthetized with isoflurane and intranasally administered with 20 μL of 1 mg/kg bleomycin PBS solution (Bleomycine Bellon, 15 mg for injection) or PBS (negative control mice). Non-bleomycin-conditioned mice were included as a negative control group. At day 11, mice (n=6 animals per group) were treated with tested conjugates (10 mg/kg i.p.) and were monitored for apparent signs of toxicity and weight loss during the duration of the experiment. A positive control group was included, treated with clinically approved conjugate Enhertu® (10 mg/kg i.p.), which is known to induce interstitial lung diseases and pneumonitis preclinically and in a small percentage of patients. At day 25 all mice were sacrificed, broncho-alveolar supernatant was obtained (by broncho-alveolar lavage) and lungs organs were harvested, weighted, and fixed in 0.1% (w/v) formaldehyde in PBS. After fixation, lungs were rinsed with a 0.02% (w/v) sodium azide in PBS solution and embedded in paraffin for histological staining. Slides were stained with anti-CD45 antibody (Abcam cat #ab10558, 1:500) to quantify level of leucocyte infiltration in the lungs. Secondary biotinylated goat anti-rabbit antibody (Vector Laboratories cat #BA-1000, 1:300) and Avidin-HRP (Vector Laboratories cat #A-2004) were used for detection. Histological experiments and imaging were outsourced at the Centre d'Imagerie Quantitative Lyon-Est (CiQLE) platform (Lyon, France). Random sections of IHC images (30% zoomed) were processed using native functionalities of the Fiji software (developed and maintained by the Laboratory for Optical and Computational Instrumentation of the University of Wisconsin-Madison, USA) to count CD45 positive cells within slides (1 slide per lung) and assess level of leucocyte infiltration. Monitoring of total counts of lymphocytes (CD3/CD4), eosinophils (CCR3/SiglecF), neutrophils (Ly6g/Ly6C) and macrophages (F4/80) in broncho-alveolar supernatants obtained from non-bleomycin-conditioned mice was done by flow cytometry. Inflammatory cytokines levels in broncho-alveolar supernatants obtained from non-bleomycin-conditioned mice were quantified by ELISA. IL-2, IL-4, IL-5, IL-6, IL-9, IL-10, IL-13 were quantified using Bio-Plex Pro™ Mouse Cytokine Th2 Panel (Bio-Rad cat #L60000UKVT), following manufacturer's instructions. TGF-β and IL-17 were quantified using Mouse TGF-beta 1 DuoSet and Mouse IL-17 DuoSet ELISA kits respectively (R&D systems cat #DY1679 and DY421), following manufacturer's instructions.

Statistical significance was evaluated using one-way ANOVA (Tukey method) using GraphPad Prism 9 software. p-values are represented as * ($p<0.033$),  ($p<0.002$), * ($p<0.0002$), and **** ($p<0.0001$) and "ns" stands for non-significant ($p>0.123$).

Figure 20:
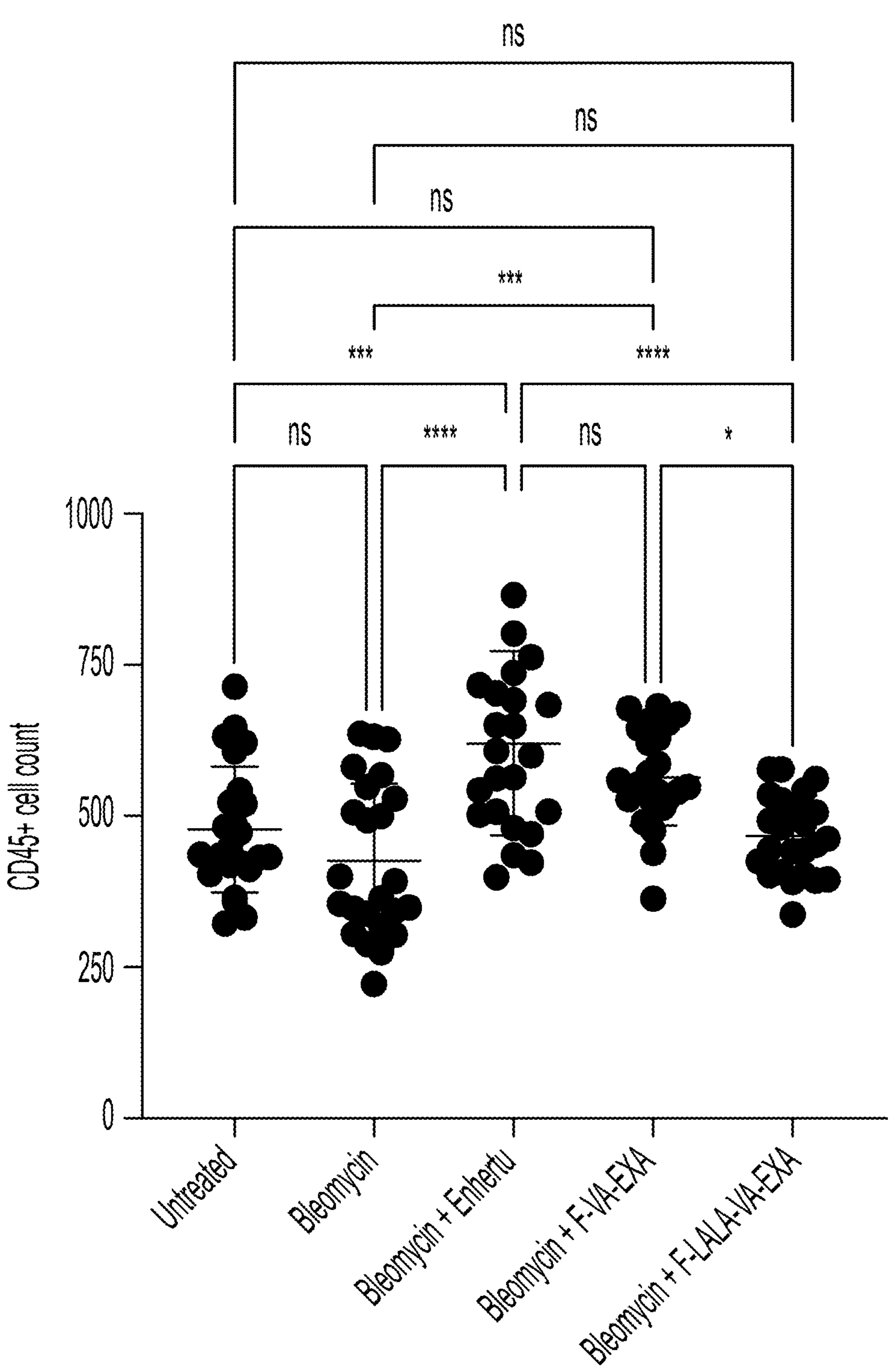
FIGS. 20 and 21 represents in vivo mice pulmonary inflammatory evaluation of conjugates, according to example 15.

IHC CD45 quantification results are shown in FIG. 20. Positive control Enhertu® ADC caused a significant increase in leucocyte inflammatory infiltration when compared to both untreated (*) and bleomycin-conditioned () negative control groups. F-VA-EXA ADC caused no significant increase in leucocyte inflammatory infiltration when compared to untreated group and caused a significant increase when compared to bleomycin-conditioned (*) control group. F-LALA-VA-EXA caused no significant increase in leucocyte inflammatory infiltration when compared to both untreated and bleomycin-conditioned negative control groups. Based on these preclinical results it can be hypothesized that F-VA-EXA and especially F-LALA-VA-EXA (Fc-silent variant) will induce less or no interstitial lung diseases or pneumonitis in a clinical setting.

Figure 21:
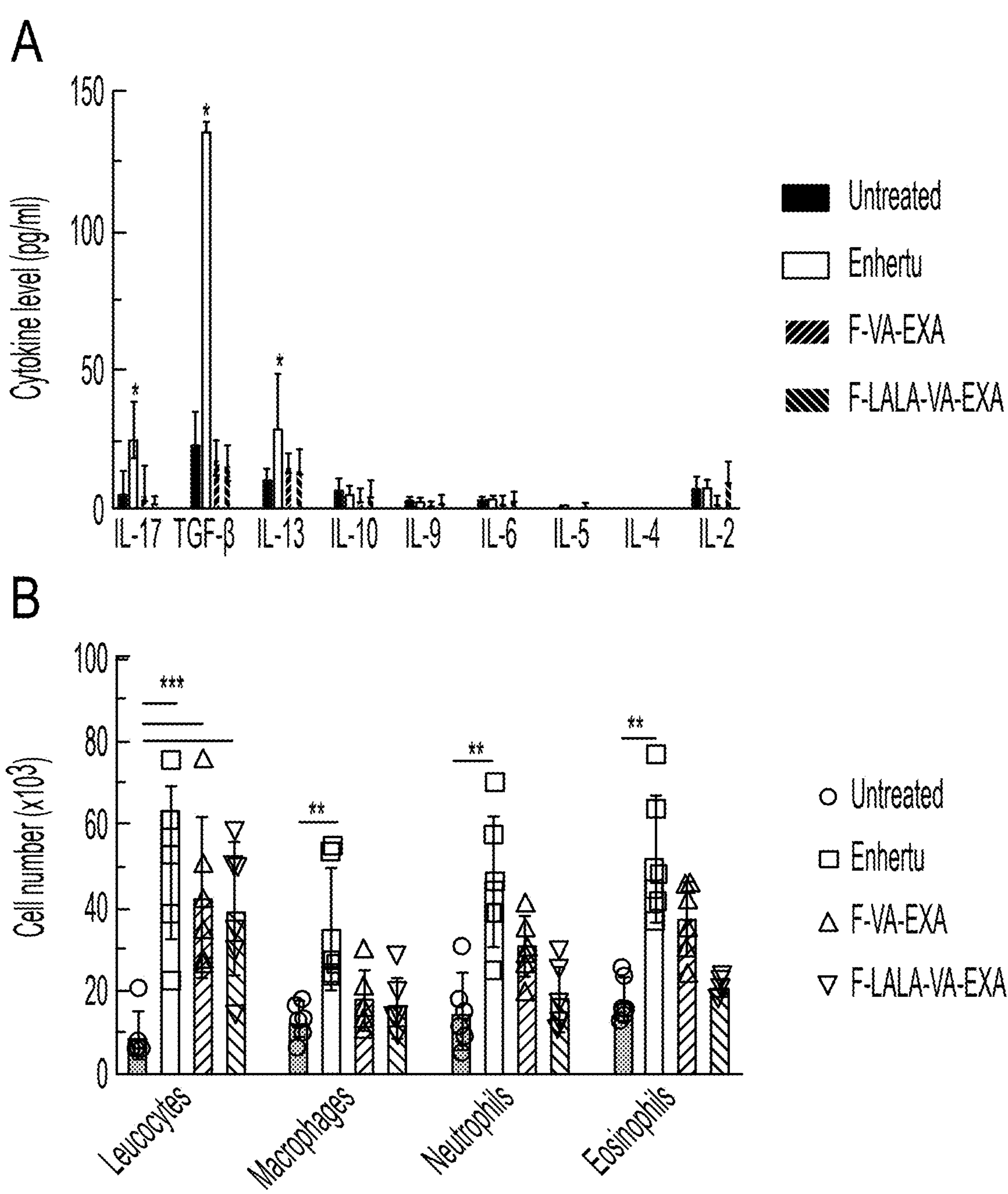

Inflammatory cytokines levels in broncho-alveolar supernatants are shown in FIG. 21A. Positive control Enhertu® ADC caused a significant increase in IL-13, IL-17 and TGF-β cytokine levels compared to untreated group. F-VA-EXA and F-LALA-VA-EXA ADC caused no significant increase in cytokine levels when compared to untreated group.

Total counts of lymphocytes, eosinophils, neutrophils and macrophages in broncho-alveolar supernatants are shown in FIG. 21B. Positive control Enhertu® caused a significant increase in lymphocytes, macrophages, neutrophils and eosinophils counts compared to untreated control group. F-VA-EXA and F-LALA-VA-EXA showed significant increase in lymphocyte counts compared to untreated control group, but no statistically significant increase in macrophages, neutrophils and eosinophils compared to untreated control group.

TABLE 11

| ADC | ENHERTU ® | F-VA-EXA | F-LALA-VA-EXA |
| --- | --- | --- | --- |
| Lung inflammatory level by CD45 expression (leucocyte infiltration) | +++ | ++ | +/− |
| Lung inflammatory level by cytokine expression in broncho-alveolar supernatant | ++ | None | None |
| Lymphocyte counts in broncho-alveolar supernatant by flow cytometry | +++ | ++ | ++ |
| Macrophages counts in broncho-alveolar supernatant by flow cytometry | ++ | − | − |
| Neutrophils counts in broncho-alveolar supernatant by flow cytometry | +++ | ++ | + |
| Eosinophils counts in broncho-alveolar supernatant by flow cytometry | +++ | ++ | + |

Example 16: Dose-Range-Finding Toxicology Study in Cynomolgus Monkeys

A nonhuman primate dose-range-finding toxicology study was conducted using purpose-bred native female cynomolgus monkeys (*Macaca fascicularis*) of Vietnam origin. The study was performed at Cynbiose SAS (Marcy-l'Étoile, France). The study protocol was approved by the testing facility Institutional Animal Care and Use Committee. F-LALA-VA-EXA ADC was intravenously administered (5 ml/kg/h, over a 30 min injection period) at a three-week interval (total of 3 doses) at dose levels of 30, 40, 50 or 60 mg/kg. Two female monkeys/group were used in the study (total of 8 animals). Following terminal sacrifice 5 days after the last administration, gross necropsy, measurement of organ weights and histopathologic examinations were conducted. Parameters evaluated during the study included mortality, clinical signs (including estimation of food consumption), body weights, ophthalmology examinations, body temperature, hematology, coagulation, clinical chemistry, urinalysis, organ weights, and macroscopic and microscopic examinations of an extensive list of tissues. ADC formulation buffer was 20 mM histidine pH 6.0, 4% (w/v) sucrose and 75 mM NaCl. Vehicle was saline 0.9%.

Results are shown in FIG. 22. F-LALA-VA-EXA ADC was well tolerated, with an estimated highest non-severely toxic dose (HNSTD) of 50 mg/kg thrice. Dosing at 60 mg/kg was not tolerated because of acute kidney failure in one of the two animals (probably target-related, as folate receptor alpha is endogenously expressed in kidneys). Preclinical therapeutic window of F-LALA-VA-EXA appears favourable, as cynomolgus HNSTD is well above efficacious therapeutic doses in rodent cancer models (after allometric scaling of doses).

The invention claimed is:

1. An antibody-drug conjugate of formula (I):

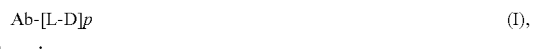

wherein:

Ab is an anti-folate receptor alpha (FRα) antibody which binds specifically to the folate receptor alpha of SEQ ID NO:12, L is a cleavable linker moiety of formula (VI):

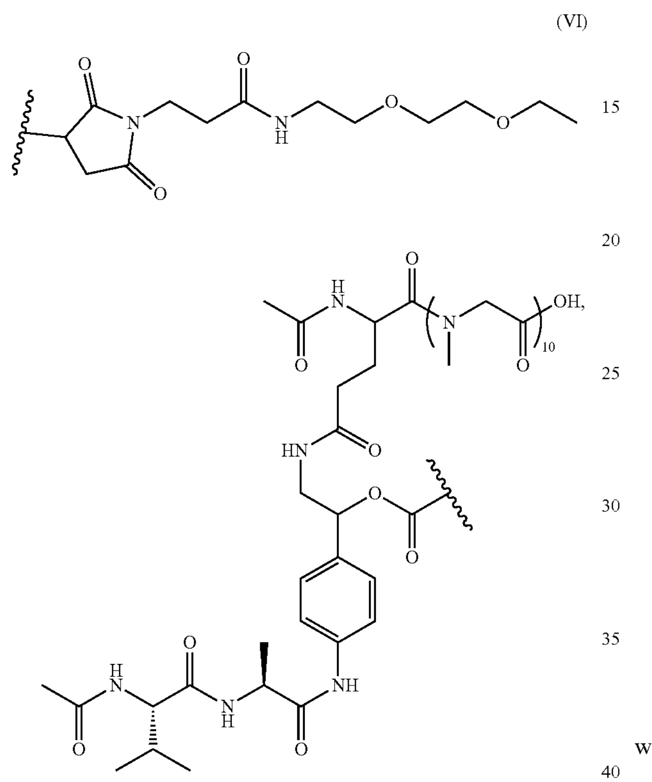

and L is covalently bonded to one or more thiol residues of said antibody,

D is the drug moiety of exatecan of formula (II) bonded to L,

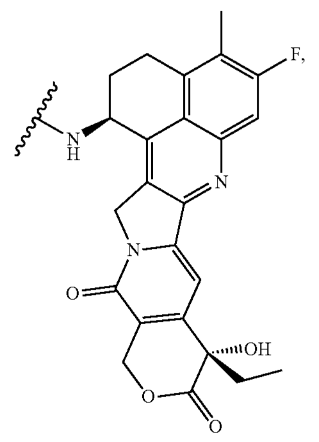

and p is from 1 to 8.

2. The antibody-drug conjugate according to claim 1, wherein p is from 6 to 8.

3. The antibody-drug conjugate according to claim 1, wherein the antibody-drug conjugate is of formula (VII)

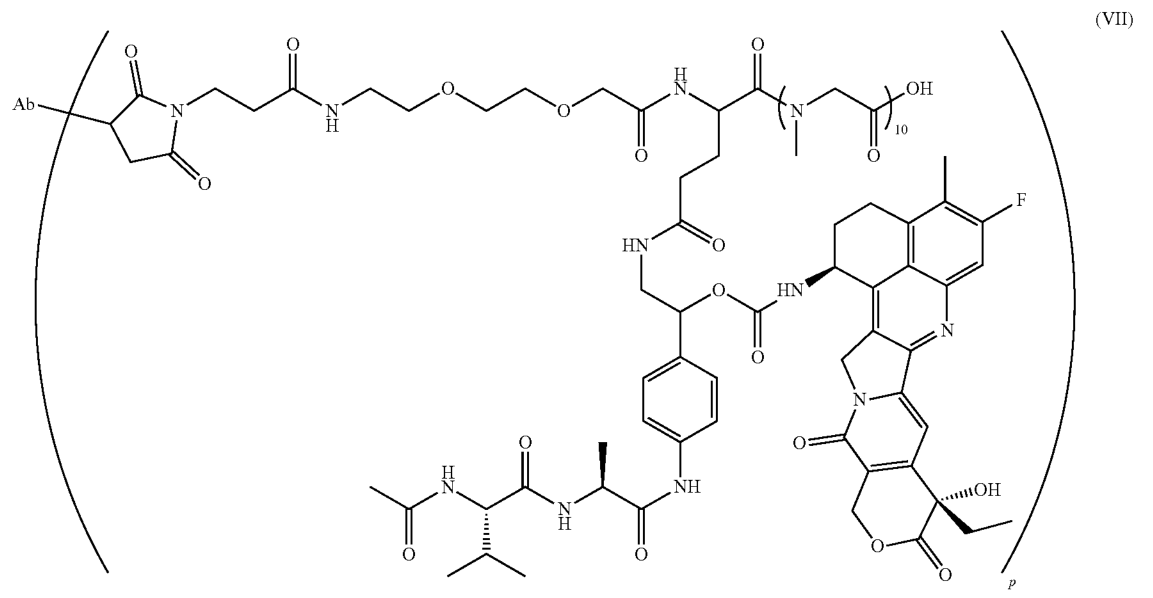

wherein Ab is an anti-FRα antibody, or its silent IgG1 variants, comprising alanine substitutions in Leucine 234 and Leucine 235 of lgG1 Fc constant region, and p is from 4 to 8.

4. The antibody-drug conjugate according to claim 3, wherein Ab is an anti-FRα antibody which comprises either:

(i) a variable heavy chain polypeptide comprising HCDR1 of SEQ ID NO:1, HCDR2 of SEQ ID NO:2, and HCDR3 of SEQ ID NO:3 and a variable light chain polypeptide comprising LCDR1 of SEQ ID NO:4, LCDR2 of SEQ ID NO:5 and LCDR3 of SEQ ID NO:6; or (ii) a variable heavy chain polypeptide comprising VH of SEQ ID NO:7 and a variable light chain polypeptide comprising VL of SEQ ID NO:8.

5. An antibody-drug conjugate of formula (VII):

(VII)

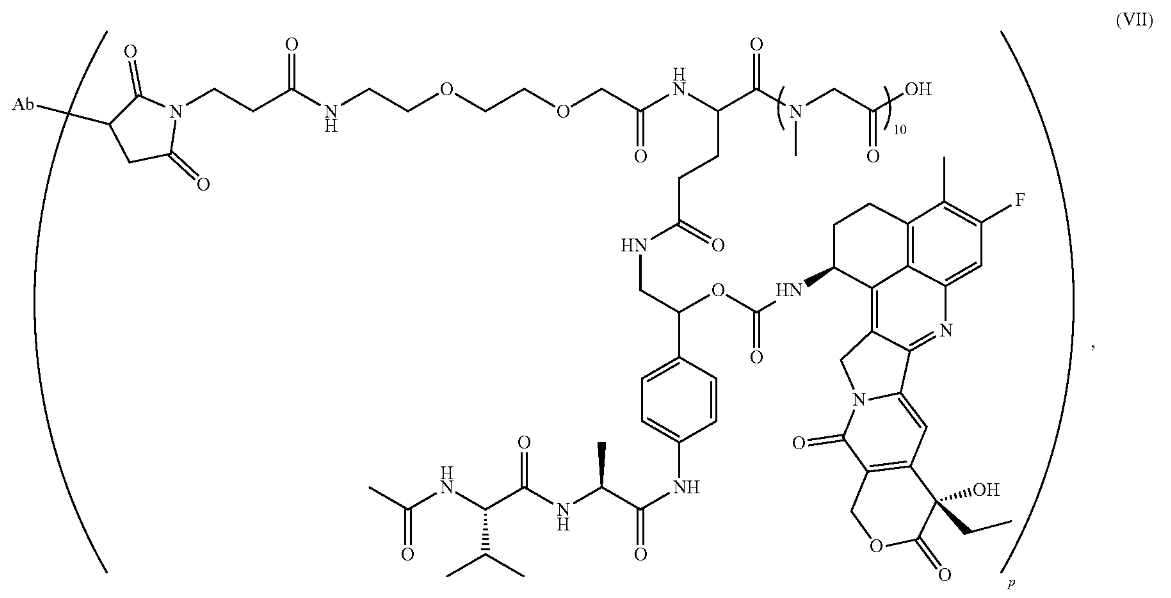

, wherein Ab is an anti-FRα antibody which comprises a variable heavy chain polypeptide comprising VH of SEQ ID NO:7 and a variable light chain polypeptide comprising VL of SEQ ID NO:8, and wherein the IgG1 Fc constant region comprises alanine substitutions in Leucine 234 and Leucine 235, and p is 8.

6. The antibody-drug conjugate according to claim 5, wherein the Ab is an anti-FRα antibody comprising a heavy chain polypeptide of SEQ ID NO:9 and a light chain polypeptide of SEQ ID NO:10.

7. A pharmaceutical composition comprising the antibody-drug conjugate according to claim 5, in combination with one or more pharmaceutically acceptable excipient, diluent or carrier.

8. A method of treating cancer in a subject in need thereof comprising administering the pharmaceutical composition of claim 7.

9. The method of claim 8, wherein the cancer is selected from the group consisting of ovarian cancer, triple negative breast cancer, non-small cell lung cancer or mesothelioma.

* * * * *

SEQUENCE LISTING

```
Sequence total quantity: 17
SEQ ID NO: 1            moltype = AA  length = 5
FEATURE                 Location/Qualifiers
REGION                  1..5
                        note = Antibody
source                  1..5
                        mol_type = protein
                        organism = synthetic construct
SEQUENCE: 1
GYGLS                                                                    5

SEQ ID NO: 2            moltype = AA  length = 17
FEATURE                 Location/Qualifiers
REGION                  1..17
                        note = Antibody
source                  1..17
                        mol_type = protein
                        organism = synthetic construct
SEQUENCE: 2
MISSGGSYTY YADSVKG                                                       17

SEQ ID NO: 3            moltype = AA  length = 10
FEATURE                 Location/Qualifiers
```

-continued

```
REGION                 1..10
                       note = Antibody
source                 1..10
                       mol_type = protein
                       organism = synthetic construct
SEQUENCE: 3
HGDDPAWFAY                                                      10

SEQ ID NO: 4           moltype = AA  length = 12
FEATURE                Location/Qualifiers
REGION                 1..12
                       note = Antibody
source                 1..12
                       mol_type = protein
                       organism = synthetic construct
SEQUENCE: 4
SVSSSISSNN LH                                                   12

SEQ ID NO: 5           moltype = AA  length = 7
FEATURE                Location/Qualifiers
REGION                 1..7
                       note = Antibody
source                 1..7
                       mol_type = protein
                       organism = synthetic construct
SEQUENCE: 5
GTSNLAS                                                         7

SEQ ID NO: 6           moltype = AA  length = 11
FEATURE                Location/Qualifiers
REGION                 1..11
                       note = Antibody
source                 1..11
                       mol_type = protein
                       organism = synthetic construct
SEQUENCE: 6
QQWSSYPYMY T                                                    11

SEQ ID NO: 7           moltype = AA  length = 119
FEATURE                Location/Qualifiers
REGION                 1..119
                       note = Antibody
source                 1..119
                       mol_type = protein
                       organism = synthetic construct
SEQUENCE: 7
EVQLVESGGG VVQPGRSLRL SCSASGFTFS GYGLSWVRQA PGKGLEWVAM ISSGGSYTYY  60
ADSVKGRFAI SRDNAKNTLF LQMDSLRPED TGVYFCARHG DDPAWFAYWG QGTPVTVSS   119

SEQ ID NO: 8           moltype = AA  length = 110
FEATURE                Location/Qualifiers
REGION                 1..110
                       note = Antibody
source                 1..110
                       mol_type = protein
                       organism = synthetic construct
SEQUENCE: 8
DIQLTQSPSS LSASVGDRVT ITCSVSSSIS SNNLHWYQQK PGKAPKPWIY GTSNLASGVP  60
SRFSGSGSGT DYTFTISSLQ PEDIATYYCQ QWSSYPYMYT FGQGTKVEIK             110

SEQ ID NO: 9           moltype = AA  length = 449
FEATURE                Location/Qualifiers
REGION                 1..449
                       note = Antibody
source                 1..449
                       mol_type = protein
                       organism = synthetic construct
SEQUENCE: 9
EVQLVESGGG VVQPGRSLRL SCSASGFTFS GYGLSWVRQA PGKGLEWVAM ISSGGSYTYY  60
ADSVKGRFAI SRDNAKNTLF LQMDSLRPED TGVYFCARHG DDPAWFAYWG QGTPVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEAAGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                 449

SEQ ID NO: 10          moltype = AA  length = 217
FEATURE                Location/Qualifiers
```

REGION 1..217
note = Antibody
source 1..217
mol_type = protein
organism = synthetic construct
SEQUENCE: 10
DIQLTQSPSS LSASVGDRVT ITCSVSSSIS SNNLHWYQQK PGKAPKPWIY GTSNLASGVP 60
SRFSGSGSGT DYTFTISSLQ PEDIATYYCQ QWSSYPYMYT FGQGTKVEIK RTVAAPSVFI 120
FPPSDEQLKS GTASVVCLLN NFYPREAKVQ WKVDNALQSG NSQESVTEQD SKDSTYSLSS 180
TLTLSKADYE KHKVYACEVT HQGLSSPVTK SFNRGEC 217

SEQ ID NO: 11 moltype = AA length = 449
FEATURE Location/Qualifiers
REGION 1..449
note = Antibody
source 1..449
mol_type = protein
organism = synthetic construct
SEQUENCE: 11
EVQLVESGGG VVQPGRSLRL SCSASGFTFS GYGLSWVRQA PGKGLEWVAM ISSGGSYTYY 60
ADSVKGRFAI SRDNAKNTLF LQMDSLRPED TGVYFCARHG DDPAWFAYWG QGTPVTVSSA 120
STKGPSVFPL APSSKSTSGG TAALGCLVKD YFPEPVTVSW NSGALTSGVH TFPAVLQSSG 180
LYSLSSVVTV PSSSLGTQTY ICNVNHKPSN TKVDKKVEPK SCDKTHTCPP CPAPELLGGP 240
SVFLFPPKPK DTLMISRTPE VTCVVVDVSH EDPEVKFNWY VDGVEVHNAK TKPREEQYNS 300
TYRVVSVLTV LHQDWLNGKE YKCKVSNKAL PAPIEKTISK AKGQPREPQV YTLPPSRDEL 360
TKNQVSLTCL VKGFYPSDIA VEWESNGQPE NNYKTTPPVL DSDGSFFLYS KLTVDKSRWQ 420
QGNVFSCSVM HEALHNHYTQ KSLSLSPGK 449

SEQ ID NO: 12 moltype = AA length = 257
FEATURE Location/Qualifiers
source 1..257
mol_type = protein
organism = Homo sapiens
SEQUENCE: 12
MAQRMTTQLL LLLVWVAVVG EAQTRIAWAR TELLNVCMNA KHHKEKPGPE DKLHEQCRPW 60
RKNACCSTNT SQEAHKDVSY LYRFNWNHCG EMAPACKRHF IQDTCLYECS PNLGPWIQQV 120
DQSWRKERVL NVPLCKEDCE QWWEDCRTSY TCKSNWHKGW NWTSGFNKCA VGAACQPFHF 180
YFPTPTVLCN EIWTHSYKVS NYSRGSGRCI QMWFDPAQGN PNEEVARFYA AAMSGAGPWA 240
AWPFLLSLAL MLLWLLS 257

SEQ ID NO: 13 moltype = DNA length = 1428
FEATURE Location/Qualifiers
misc_feature 1..1428
note = Antibody
source 1..1428
mol_type = other DNA
organism = synthetic construct
SEQUENCE: 13
gcggccgcca tgaattttgg actgaggctg attttcctgg tgctgaccct gaaaggcgtc 60
cagtgtgaag tccaattagt cgagagtggc ggggggggtcg tccaacccgg ccgttcatta 120
cggctctcct gctccgcctc tgggttcacc ttctcggggt acggcctatc atgggtccgt 180
caagctcctg gcaaaggcct ggaatgggtc gccatgatta gtagcggggg gagctatacc 240
tattacgccg acagtgtgaa ggggcgattc gccattagta gggacaatgc aaagaacacg 300
ctgtttctgc aaatggactc gttgagaccc gaggacacgg gtgtctactt ttgcgcacgt 360
cacggtgacg atccagcctg gttcgcatat tgggggcagg gtacccccgt tacggtctcg 420
agcgctagca caaagggccc tagtgtgttt cctctggctc cctcttccaa atccacttct 480
ggtggcactg ctgctctggg atgcctggtg aaggattact ttcctgaacc tgtgactgtc 540
tcatggaact ctggtgctct gacttctggt gtccacactt tccctgctgt gctgcagtct 600
agtggactgt actctctgtc atctgtggtc actgtgccct cttcatctct gggaacccag 660
acctacattt gtaatgtgaa ccacaaacca tccaacacta aagtggacaa aaaagtggaa 720
cccaaatcct gtgacaaaac ccacacctgc ccaccttgtc ctgcccctga agccgccgga 780
ggaccttctg tgtttctgtt ccccccccaaa ccaaaggata ccctgatgat ctctagaacc 840
cctgaggtga catgtgtggt ggtggatgtg tctcatgagg accctgaggt caaattcaac 900
tggtacgtgg atggagtgga agtccacaat gccaaaacca agcctagaga ggaacagtac 960
aattcaacct acagagtggt cagtgtgctg actgtgctgc atcaggattg gctgaatggc 1020
aaggaataca agtgtaaagt ctcaaacaag gccctgcctg ctccaattga gaaaacaatc 1080
tcaaaggcca agggacagcc tagggaaccc caggtctaca ccctgccacc ttcaagagac 1140
gaactgacca aaaaccaggt gtccctgaca tgcctggtca aaggcttcta cccttctgac 1200
attgctgtgg agtgggagtc aaatggacag cctgagaaca actacaaaac aaccccccct 1260
gtgctggatt ctgatggctc tttctttctg tactccaaac tgactgtgga caagtctaga 1320
tggcagcagg ggaatgtctt ttcttgctct gtcatgcatg aggctctgca taaccactac 1380
actcagaaat ccctgtctct gtctcccggg aaatgatagt aaaagctt 1428

SEQ ID NO: 14 moltype = DNA length = 732
FEATURE Location/Qualifiers
misc_feature 1..732
note = Antibody
source 1..732
mol_type = other DNA

```
                         organism = synthetic construct
SEQUENCE: 14
gcggccgcca tgaattttgg actgaggctg attttcctgg tgctgaccct gaaaggcgtc  60
cagtgtgaca tccagctgac acagagccca agttccctgt ctgcatccgt gggggatagg  120
gttacaatca cttgtagtgt aagcagctcg atcagcagca ataacctgca ctggtatcaa  180
cagaaaccgg gtaaggcacc aaagccttgg atttacggca ccagtaatct ggcctccggg  240
gtgccgtctc gcttttctgg gtccggcagc ggtactgact acacatttac aatcagcagc  300
ctacagcctg aggacattgc gacctattac tgccagcagt ggtccagcta cccatatatg  360
tatacgttcg ggcagggtac caaggtcgag atcaagcgta cggtcgcggc gccttctgtg  420
ttcattttcc ccccatctga tgaacagctg aaatctggca ctgcttctgt ggtctgtctg  480
ctgaacaact tctaccctag agaggccaaa gtccagtgga aagtggacaa tgctctgcag  540
agtgggaatt cccaggaatc tgtcactgag caggactcta aggatagcac atactccctg  600
tcctctactc tgacactgag caaggctgat tacgagaaac acaaagtgta cgcctgtgaa  660
gtcacacatc aggggctgtc tagtcctgtg accaaatcct tcaatagggg agagtgctga  720
tagtaaaagc tt                                                     732

SEQ ID NO: 15            moltype = DNA  length = 1428
FEATURE                  Location/Qualifiers
misc_feature             1..1428
                         note = Antibody
source                   1..1428
                         mol_type = other DNA
                         organism = synthetic construct
SEQUENCE: 15
gcggccgcca tgaattttgg actgaggctg attttcctgg tgctgaccct gaaaggcgtc  60
cagtgtgaag tccaattagt cgagagtggc ggggggggtcg tccaacccgg ccgttcatta  120
cggctctcct gctccgcctc tgggttcacc ttctcggggt acggcctatc atgggtccgt  180
caagctcctg gcaaaggcct ggaatgggtc gccatgatta gtagcggggg gagctatacc  240
tattacgccg acagtgtgaa ggggcgattc gccattagta gggacaatgc aaagaacacg  300
ctgtttctgc aaatggactc gttgagaccc gaggacacgg gtgtctactt ttgcgcacgt  360
cacggtgacg atccagcctg gttcgcatat tgggggcagg gtacccccgt tacggtctcg  420
agcgctagca caaagggccc tagtgtgttt cctctggctc cctcttccaa atccacttct  480
ggtggcactg ctgctctggg atgcctggtg aaggattact ttcctgaacc tgtgactgtc  540
tcatggaact ctggtgctct gacttctggt gtccacactt tccctgctgt gctgcagtct  600
agtggactgt actctctgtc atctgtggtc actgtgccct cttcatctct gggaacccag  660
acctacattt gtaatgtgaa ccacaaacca tccaacacta aagtggacaa aaaagtggaa  720
cccaaatcct gtgacaaaac ccacacctgc ccaccttgtc ctgcccctga actgctggga  780
ggaccttctg tgtttctgtt ccccccccaaa ccaaaggata ccctgatgat ctctagaacc  840
cctgaggtga catgtgtggt ggtggatgtg tctcatgagg accctgaggt caaattcaac  900
tggtacgtgg atggagtgga agtccacaat gccaaaacca agcctagaga ggaacagtac  960
aattcaacct acagagtggt cagtgtgctg actgtgctgc atcaggattg gctgaatggc  1020
aaggaataca agtgtaaagt ctcaaacaag gccctgcctg ctccaattga gaaaacaatc  1080
tcaaaggcca agggacagcc tagggaaccc caggtctaca ccctgccacc ttcaagagac  1140
gaactgacca aaaaccaggt gtccctgaca tgcctggtca aaggcttcta cccttctgac  1200
attgctgtgg agtgggagtc aaatggacag cctgagaaca actacaaaac aacccccccct  1260
gtgctggatt ctgatggctc tttctttctg tactccaaac tgactgtgga caagtctaga  1320
tggcagcagg ggaatgtctt ttcttgctct gtcatgcatg aggctctgca taaccactac  1380
actcagaaat ccctgtctct gtctcccggg aaatgatagt aaaagctt              1428

SEQ ID NO: 16            moltype = AA  length = 447
FEATURE                  Location/Qualifiers
REGION                   1..447
                         note = Antibody
source                   1..447
                         mol_type = protein
                         organism = synthetic construct
SEQUENCE: 16
QVQLVQSGAE VVKPGASVKI SCKASGYTFT GYFMNWVKQS PGQSLEWIGR IHPYDGDTFY  60
NQKFQGKATL TVDKSSNTAH MELLSLTSED FAVYYCTRYD GSRAMDYWGQ GTTVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPG                                     447

SEQ ID NO: 17            moltype = AA  length = 218
FEATURE                  Location/Qualifiers
REGION                   1..218
                         note = Antibody
source                   1..218
                         mol_type = protein
                         organism = synthetic construct
SEQUENCE: 17
DIVLTQSPLS LAVSLGQPAI ISCKASQSVS FAGTSLMHWY HQKPGQQPRL LIYRASNLEA  60
GVPDRFSGSG SKTDFTLTIS PVEAEDAATY YCQQSREYPY TFGGGTKLEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218
```